(12) United States Patent
Hoelzl et al.

(10) Patent No.: US 10,259,931 B2
(45) Date of Patent: Apr. 16, 2019

(54) 3-PHENYL-BENZOFURAN-2-ONE DERIVATIVES CONTAINING PHOSPHORUS AS STABILIZERS

(71) Applicant: BASF SE, Ludwigshafen (DE)

(72) Inventors: Werner Hoelzl, Eschentzwiller (FR);
Bruno Rotzinger, Delemont (CH);
Kai-Uwe Schoening, Oberwil (CH);
Roswell Easton King, Pleasantville, NY (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/920,877

(22) Filed: Mar. 14, 2018

(65) Prior Publication Data

US 2018/0201760 A1    Jul. 19, 2018

Related U.S. Application Data

(63) Continuation of application No. 15/119,317, filed as application No. PCT/EP2015/053153 on Feb. 13, 2015, now Pat. No. 9,951,207.

(30) Foreign Application Priority Data

Feb. 17, 2014    (EP) .................................... 14155326

(51) Int. Cl.
| | |
|---|---|
| *C08K 5/29* | (2006.01) |
| *C08K 5/529* | (2006.01) |
| *C08K 5/523* | (2006.01) |
| *C07F 9/655* | (2006.01) |
| *C07F 9/6574* | (2006.01) |
| *C08K 5/04* | (2006.01) |
| *C08K 5/5377* | (2006.01) |
| *C08K 5/098* | (2006.01) |

(52) U.S. Cl.
CPC .......... *C08K 5/529* (2013.01); *C07F 9/65517* (2013.01); *C07F 9/65744* (2013.01); *C08K 5/04* (2013.01); *C08K 5/523* (2013.01); *C08K 5/5377* (2013.01); *C08K 5/098* (2013.01)

(58) Field of Classification Search
None
See application file for complete search history.

(56) References Cited

U.S. PATENT DOCUMENTS 4,325,863 A    4/1982 Hinsken et al.
4,338,244 A    7/1982 Hinsken et al.
(Continued)

FOREIGN PATENT DOCUMENTS

DE    43 16 611 A1    11/1993
DE    43 16 622 A1    11/1993
(Continued)

OTHER PUBLICATIONS

International Search Report dated Apr. 23, 2015 in PCT/EP2015/053153 filed Feb. 13, 2015.
(Continued)

*Primary Examiner* — Robert T Butcher
(74) *Attorney, Agent, or Firm* — Oblon, McClelland, Maier & Neustadt, L.L.P.

(57) ABSTRACT

The invention relates to a composition comprising an organic material susceptible to oxidative, thermal or light-induced degradation and a compound of formula I-P, I-O or I-M

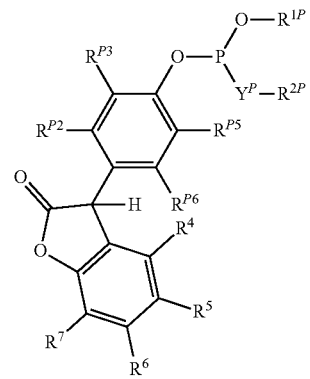
(I-P)

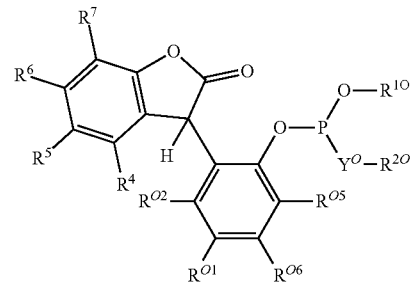

(I-O)

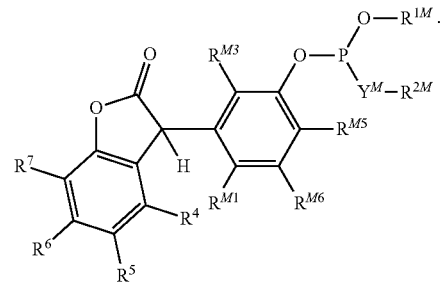

(I-M)

Further embodiments are a compound of formula I-P, I-O or I-M, a process for protection of the organic material by the compound, the use of the compound for stabilizing the organic material, an additive composition comprising the compound, a process for manufacturing the compound and intermediates involved therein.

34 Claims, No Drawings

(56) References Cited

U.S. PATENT DOCUMENTS

| | | | |
|---|---|---|---|
| 5,175,312 | A | 12/1992 | Dubs et al. |
| 5,216,052 | A | 6/1993 | Nesvadba et al. |
| 5,252,643 | A | 10/1993 | Nesvadba |
| 5,428,162 | A | 6/1995 | Nesvadba |
| 5,858,905 | A | 1/1999 | Smith et al. |
| 6,224,791 | B1 | 5/2001 | Stevenson et al. |
| 2006/0020061 | A1 | 1/2006 | Knoll et al. |
| 2008/0023881 | A1 | 1/2008 | Kubo |
| 2012/0238677 | A1 | 9/2012 | Chiu et al. |

FOREIGN PATENT DOCUMENTS

| | | |
|---|---|---|
| DE | 43 16 876 A1 | 11/1993 |
| EP | 0 589 839 A1 | 3/1994 |
| EP | 0 591 102 A1 | 4/1994 |
| EP | 0 648 765 A1 | 4/1995 |
| EP | 2 500 341 A1 | 9/2012 |
| WO | 80/01566 A1 | 8/1980 |

OTHER PUBLICATIONS

European Search Report dated Sep. 2, 2014 in Application No. EP 14 15 5326.
International Preliminary Report on Patentability and Written Opinion dated Aug. 23, 2016 in PCT/EP2015/053153.
Extended European Search Report dated Dec. 17, 2018, in European Patent Application No. 18178040.4, filed Feb. 13, 2015.

3-PHENYL-BENZOFURAN-2-ONE DERIVATIVES CONTAINING PHOSPHORUS AS STABILIZERS

This application is a Continuation of U.S. application Ser. No. 15/119,371, which was filed on Aug. 16, 2016. U.S. application Ser. No. 15/119,371 is a National Stage of PCT/EP2015/053153, which was filed on Feb. 13, 2015. This application is based upon and claims the benefit of priority to European Application No. 14155326.3, which was filed on Feb. 17, 2014.

The current invention relates to a composition comprising an organic material to be stabilized and a specific group of 3-phenyl-benzofuran-2-one derivatives containing phosphorus as stabilizer. A process for protection of the organic material by the specific group of 3-phenyl-benzofuran-2-one derivatives, the use of the latter one for stabilizing, the specific group of 3-phenyl-benzofuran-2-one derivatives, an additive composition comprising the latter one, a process for manufacturing the latter one and intermediates involved therein are further embodiments.

WO 80/01566 A discloses benzofuran-2-one or indolin-2-one derivatives as stabilizers.

U.S. Pat. No. 5,428,162 discloses as a stabilizer inter alia a 3-phenyl-3H-benzofuran-2-one derivative, which is substituted by a di($C_1$-$C_6$-alkyl)phosphonate group, e.g. compound No. 120 (=2-[4-(5-methyl-2-oxo-3H-benzofuran-3-yl)phenoxy]ethyl 2-diethoxyphosphorylacetate) as depicted:

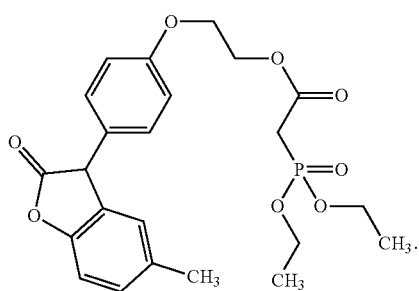 [SMILES: CCOP(=O)(CC(=O)OCCOc1ccc(C2C(=O)Oc3ccc(C)cc32)cc1)OCC]

EP 2500341 A discloses as a stabilizer inter alia a 3-phenyl-3H-benzofuran-2-one derivative, which is substituted by an oxocarbonylphenyl or an oxocarbonyl group containing inter alia phenolic groups, e.g. compounds CT-500, CT-501 or CT-502 as depicted:

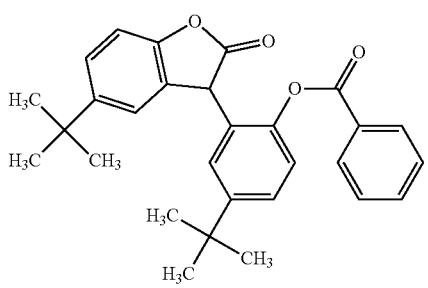

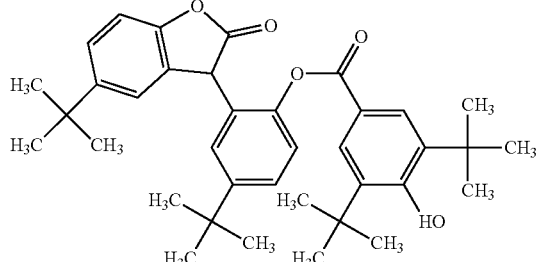

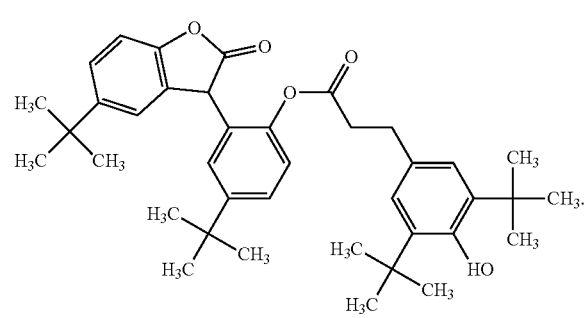

It has now been found that a specific group of phosphorus-containing benzofuran-2-one derivatives is suitable for stabilization of an organic material against degradation by heat, light and/or oxidation.

The present invention relates to a composition, which comprises
a) an organic material susceptible to oxidative, thermal or light-induced degradation, and
b) a compound of formula I-P, I-O or I-M

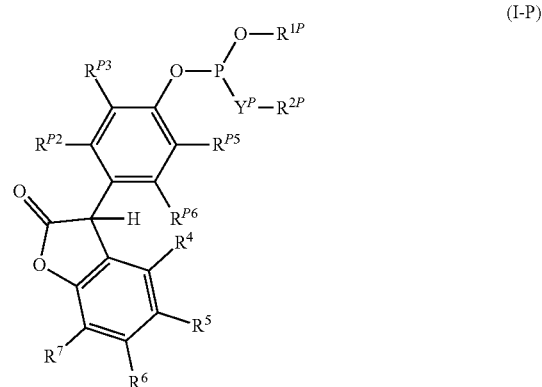

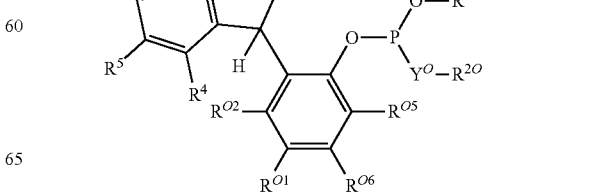

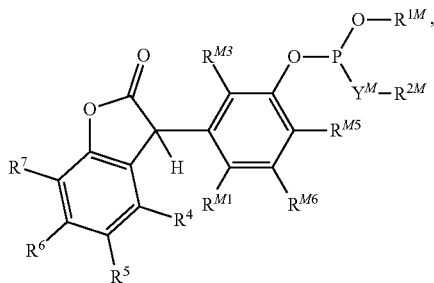
(I-M)

wherein
$Y^P$, $Y^O$ and $Y^M$ are oxygen or represent a covalent bond;
when $Y^P$, $Y^O$ and $Y^M$ are oxygen,
$R^{1P}$ represents one of the subformulae II-P, II-O or II-M

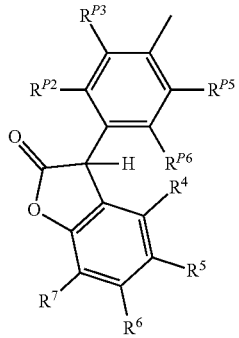
(II-P)

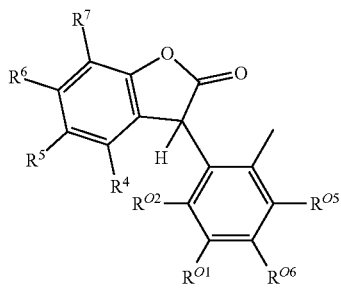
(II-O)

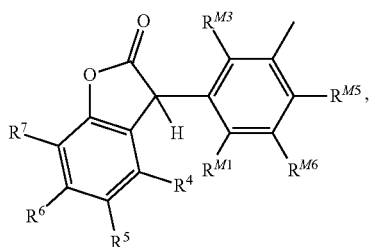
(II-M)

$R^{1O}$ represents one of the subformulae II-O or II-M,
$R^{1M}$ represents the subformula II-M, or
$R^{1P}$ together with $R^{2P}$, $R^{1O}$ together with $R^{2O}$ and $R^{1M}$ together with $R^{2M}$ represent one of the subformulae III, IV or V

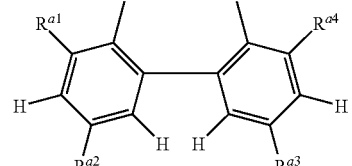
(III)

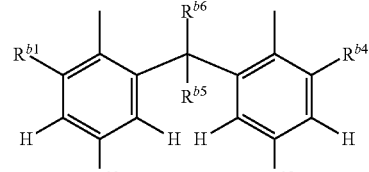
(IV)

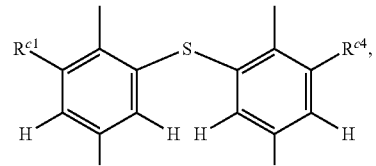
(V)

or
$R^{1P}$, $R^{1O}$ and $R^{1M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom,
$R^{2P}$ represents one of subformulae II-P, II-O or II-M,
$R^{2O}$ represents one of subformulae II-O or II-M,
$R^{2M}$ represents subformula II-M, or
$R^{2P}$ together with $R^{1P}$, $R^{2O}$ together with $R^{1O}$ and $R^{2M}$ together with $R^{1M}$ represent one of the subformulae III, IV or V, or
$R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;
when $Y^P$, $Y^O$ and $Y^M$ represent a covalent bond,
$R^{1P}$ represents one of the subformulae II-P, II-O or II-M,
$R^{1O}$ represents one of the subformulae II-O or II-M,
$R^{1M}$ represents the subformula II-M, or
$R^{1P}$, $R^{1O}$ and $R^{1M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom,
$R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, or halogen;
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{O1}$, $R^{O2}$, $R^{O5}$ and $R^{O6}$ are independently from each other hydrogen or $C_1$-$C_8$-alkyl,
$R^{M1}$, $R^{M3}$, $R^{M5}$ and $R^{M6}$ are independently from each other hydrogen or $C_1$-$C_8$-alkyl, $R^{a1}$, $R^{a2}$, $R^{a3}$ and $R^{a4}$ are independently from each other hydrogen or $C_1$-$C_8$-alkyl,
$R^{b1}$, $R^{b2}$, $R^{b3}$, $R^{b4}$, $R^{b5}$ and $R^{b6}$ are independently from each other hydrogen or $C_1$-$C_8$-alkyl, and
$R^{c1}$, $R^{c2}$, $R^{c3}$ and $R^{c4}$ are independently from each other hydrogen or $C_1$-$C_8$-alkyl.

The one point of attachment at subformulae II-P, II-O or II-M is denoted by the end of the line, which does not carry a character and is blank. The two points of attachment at subformulae III, IV or V are denoted each by the end of the respective line, which does not carry a character and is blank.

Once $R^{1P}$ together with $R^{2P}$, $R^{1O}$ together with $R^{2O}$ and $R^{1M}$ together with $R^{2M}$ represent one of the subformulae III, IV or V, then $R^{2P}$ together with $R^{1P}$, $R^{2O}$ together with $R^{1O}$ and $R^{2M}$ together with $R^{1M}$ represent the same subformula.

A compound of formula I-P, I-O or I-M possesses at least one asymmetric carbon atom, i.e. a carbon atom at the 3-position of the benzofuran-2-one structural unit. Further asymmetric carbon atoms can be present in alkyl substituents with at least four carbon atoms. A phosphorus atom, which is substituted with three different substituents, can show a hindered inversion, which can lead dependent on temperature to an asymmetric phosphorus atom. The invention relates to any one of these enantiomers, resulting diastereomers or mixtures thereof.

$C_6$-$C_{10}$-aryl, which is unsubstituted or substituted by $C_1$-$C_8$-alkyl, $C_1$-$C_8$-alkoxy, halogen or one phenyl, is for example phenyl, 2-methyl-phenyl, 3-methyl-phenyl, 4-methyl-phenyl, 2,4-dimethyl-phenyl, 3,5-dimethyl-phenyl, 4-(1,1-dimethylethyl)-phenyl, 4-(1,1,3,3-tetramethylpentyl)-phenyl, naphthalen-1-yl, naphthalen-2-yl, 6-methylnaphthalen-2-yl, 4-phenyl-phenyl, 2-methoxy-phenyl, 3-methoxy-phenyl, 4-methoxy-phenyl, 2-ethoxyphenyl, 3-ethoxy-phenyl, 3-(n-propoxy)-phenyl, 4-(1,1-dimethylethoxy)phenyl, 2-chloro-phenyl, 3-chlorophenyl, 4-chlorophenyl, 2-chloro-4-methylphenyl. Preferred is $C_6$-$C_{10}$-aryl, which is unsubstituted or substituted by $C_1$-$C_8$-alkyl or $C_1$-$C_8$-alkoxy. Especially preferred is phenyl, which is unsubstituted or substituted by $C_1$-$C_8$-alkyl. Particularly preferred is phenyl.

$C_1$-$C_8$-alkyl is linear or branched and for example methyl, ethyl, n-propyl, 1-methyl-ethyl, n-butyl, 1-methyl-propyl, 2-methyl-propyl, 1,1-dimethyl-ethyl, n-pentyl, 1-methyl-butyl, 3-methyl-butyl, n-hexyl, 1-methyl-pentyl, 2-methyl-pentyl, 4-methyl-pentyl, 2-ethyl-butyl, n-heptyl, 1-methylhexyl, n-octyl, 1-methyl-heptyl, 2-ethyl-hexyl, 5,5-dimethyl-hexyl or 1,1,3,3-tetramethyl-butyl. Preferred is $C_1$-$C_4$-alkyl or $C_8$-alkyl, in particular methyl, ethyl, 1-methyl-ethyl, 1-methyl-propyl 1,1-dimethyl-ethyl or 1,1,3,3-tetramethyl-butyl. Preferred is $C_1$-$C_4$-alkyl, in particular methyl, ethyl, 1-methyl-ethyl, 1-methyl-propyl 1,1-dimethyl-ethyl and very particular methyl, 1-methyl-propyl or 1,1-dimethyl-ethyl.

$C_1$-$C_8$-alkoxy is linear or branched and for example methoxy, ethoxy, n-propoxy, 1-methyl-ethoxy, n-butoxy, 1-methyl-propoxy, 1,1-dimethyl-ethoxy, n-pentoxy, 2-methylpentoxy, 2-ethyl-butoxy, 1-methyl-hexoxy, n-octoxy, 1-methyl-heptoxy, 2-ethyl-hexoxy, 1,1,3,3-tetramethyl-butoxy. Preferred is $C_1$-$C_4$-alkoxy and in particular methoxy.

Halogen is for example a fluorine atom (=fluoro), chlorine atom (=chloro), a bromine atom (=bromo) or a iodine atom (=iodo). Preferred is a chlorine atom or a fluorine atom, in particular a fluorine atom.

$C_1$-$C_{18}$-alkyl is linear or branched and for example methyl, ethyl, n-propyl, 1-methyl-ethyl, n-butyl, 1-methyl-propyl, 2-methyl-propyl, 1,1-dimethyl-ethyl, n-pentyl, 1-methyl-butyl, 3-methyl-butyl, n-hexyl, 1-methyl-pentyl, 2-methyl-pentyl, 4-methyl-pentyl, 2-ethyl-butyl, n-heptyl, 1-methyl-hexyl, n-octyl, 1-methyl-heptyl, 2-ethyl-hexyl, 5,5-dimethyl-hexyl, 1,1,3,3-tetramethyl-butyl, n-nonyl, 2-ethyl-heptyl, n-decyl, undecyl, n-dodecyl, tridecyl, tetradecyl, pentadecyl, n-hexadecyl or n-octadecyl. Preferred is $C_1$-$C_{18}$-alkyl and in particular $C_1$-$C_{12}$-alkyl.

$C_3$-$C_{16}$-cycloalkyl is unsubstituted or substituted by $C_1$-$C_4$-alkyl and is for example cyclobutyl, cyclopentyl, 3,4-dimethyl-cyclopentyl, cyclohexyl, 4-methyl-cyclohexyl, 4-(1-methylethyl)-cyclohexyl, 4-(1,1-dimethylethyl)-cyclohexyl, 3,5-dimethyl-cyclohexyl, 5-methyl-2-(1-methyl-ethyl)-cyclohexyl, cycloheptyl, cyclooctyl or cyclododecyl. Preferred is $C_5$-$C_7$-cycloalkyl and in particular cyclohexyl.

$C_7$-$C_{13}$-aralkyl is for example benzyl, 4-methyl-benzyl, 2-phenyl-ethyl, 3,5-dimethylbenzyl, 1-phenyl-1,1-dimethylmethyl, 3-phenyl-propyl, 3-phenyl-2-methyl-propyl, 3,5-ditert-butyl-benzyl or 4-phenyl-phenyl-methyl. Preferred is benzyl.

$C_2$-$C_{18}$-alkenyl is linear or branched and for example vinyl, allyl, Z- or E-but-2-ene-yl, Z or E-but-3-ene-yl, Z- or E-pent-2-ene-yl, pent-4-ene-yl, Z- or E-2-methyl-but-2-ene-yl, Z- or E-3-methyl-but-3-ene-yl, Z- or E-hex-1-ene-yl, Z- or E-hexadec-9-ene-yl or Z- or E-octadec-9-ene-yl, (9Z, 12Z)-octadeca-9,12-diene-yl or (9Z,12Z,15Z)-octadeca-9,12,15-triene-yl. Preferred is allyl.

$C_2$-$C_{30}$-alkyl, which is interrupted by one or more oxygen atoms, is linear or branched and for example methoxymethyl, 2-methoxy-ethyl, 2-ethoxy-ethyl, 2-(2-methoxyethoxy)-ethyl, 2-n-butoxy-ethyl, 2-[2-(2-methoxy-ethoxy)-ethoxy]-ethyl, 2-[2-[2-(2-methoxy-ethoxy)-ethoxy]-ethoxy]-ethyl, 2-(2-methoxy-1-methyl-ethoxy)-1-methyl-ethyl, 3-(n-propoxy)-propyl, 2-[2-[2-(2-n-butoxy-ethoxy)-ethoxy]-ethoxy]-ethyl, 2-[2-(2-n-butoxy-2-methyl-ethoxy)-2-methyl-ethoxy]-2-methyl-ethyl or 2-[(2-n-lauryl)-ethoxy]-ethyl. Preferred is 2-methoxy-ethyl or 2-ethoxy-ethyl.

$C_2$-$C_{16}$-alkyl, which is interrupted by one sulfur atom, is linear or branched and for example 2-(methyl-sulfanyl)-ethyl, 3-thiaundecyl or 3-thiapentadecyl.

An organic material susceptible to oxidative, thermal or light-induced degradation is for example a polymer, an oligohydroxy compound, a wax, a fat or a mineral oil.

A polymer can be natural, semi-synthetic or synthetic. A natural polymer is isolated from a natural source without further synthetic modifications. A synthetic polymer does not contain a polymer part isolated from a natural source. A semi-synthetic polymer contains at least one natural polymer part, wherein the natural polymer part can be synthetically modified and/or reacted with monomers to form the semi-synthetic polymer.

A polymer can be thermoplastic, i.e. it can be shaped into a new form at an elevated temperature, for example at a temperature in the range from 135° C. to 350° C., especially from 150° C. to 340° C.

A copolymer is a polymer, wherein at least two different monomers are co-polymerized. Preferred are copolymers, wherein the weight content of one monomer is above 50% based on the weight of all monomers.

Preferably, a polymer is a substance consisting of molecules characterized by the sequence of one or more types of monomer units and comprising a simple weight majority of molecules containing at least three monomer units which are covalently bound to at least one other monomer unit or other reactant and consists of less than a simple weight majority of molecules of the same molecular weight. Such molecules must be distributed over a range of molecular weights wherein differences in the molecular weight are primarily attributable to differences in the number of monomer units. In the context of this definition a monomer unit means the reacted form of a monomer in a polymer.

Examples of a polymer are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPEHMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).
  b) catalytic polymerisation using a catalyst that normally contains one or more than one metal of groups IVb, Vb, VIb (for example chromium) or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylenepropylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

A special copolymer of two monoolefins is a pipe grade polypropylene random copolymer, which is obtainable from the polymerization of more than 90% by weight of propylene and of less than 10% by weight, typically between 2 and 6% by weight, of ethylene.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where isotactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes, for example polyurethanes synthesized from a polyol and an aliphatic or aromatic polyisocyanate such as polyurethanes derived from hydroxyl-terminated polyethers, polyesters or polybutadienes on the one hand and aliphatic or aromatic polyisocyanates on the other, as well as precursors thereof.

Hydroxyl-terminated polyethers are known and are prepared, for example, by polymerizing epoxides such as ethylene oxide, propylene oxide, butylene oxide, tetrahydrofuran, styrene oxide or epichlorohydrin with themselves, for example in the presence of $BF_3$, or by addition reaction of these epoxides, alone or as a mixture or in succession, with starting components containing reactive hydrogen atoms, such as water, alcohols, ammonia or amines, for example ethylene glycol, propylene 1,3- and 1,2-glycol, trimethylolpropane, 4,4'-dihydroxydiphenylpropane, aniline, ethanolamine or ethylenediamine. Sucrose polyethers are also suitable in accordance with the invention. In many cases preference is given to those polyethers which predominantly (up to 90% by weight, based on all the OH groups present in the polyether) contain primary OH groups. Furthermore, polyethers modified by vinyl polymers, as are formed, for example, by polymerizing styrene and acrylonitrile in the presence of polyethers, are suitable, as are polybutadienes containing OH groups.

In particular, a polyol compound has a molecular weight of 400-10000, especially 800 to 10000, and is a compound containing several hydroxyl groups, especially containing from 2 to 8 hydroxyl groups, especially from 2 to 4.

Suitable polyisocyanates are aliphatic or aromatic, for example ethylene diisocyanate, 1,4-tetramethylene diisocyanate, 1,6-hexamethylene diisocyanate, 1,12-dodecane diisocyanate, cyclobutane 1,3-diisocyanate, cyclohexane 1,3- and -1,4-diisocyanate and also any desired mixtures of these isomers, 1-isocyanato-3,3,5-trimethyl-5-isocyanatomethylcyclohexane, 2,4- and 2,6-hexahydrotolylene diisocyanate and also any desired mixtures of these isomers, hexahydro-1,3- and/or-1,4-phenylene diisocyanate, perhydro-2,4'- and/or-4,4'-diphenylmethanediisocyanate, 1,3- and 1,4-phenylene diisocyanate, 2,4- and 2,6-tolylene diisocyanate, and also any desired mixtures of these isomers, diphenylmethane 2,4'- and/or-4,4'-diisocyanate, naphthylene 1,5-diisocyanate, triphenylmethane 4,4',4''-triisocyanate, polyphenyl-polymethylene polyisocyanates as are obtained by aniline-formaldehyde condensation followed by phosgenization, m- and p-isocyanatophenylsulfonyl isocyanates, perchlorinated aryl polyisocyanates, polyisocyanates containing carbodiimide groups, polyisocyanates containing allophanate groups, polyisocyanates containing isocyanurate groups, polyisocyanates containing urethane groups, polyisocyanates containing acylated urea groups, polyisocyanates containing biuret groups, polyisocyanates containing ester groups, reaction products of the abovementioned isocyanates with acetals, and polyisocyanates containing polymeric fatty acid radicals.

It is also possible to employ the isocyanate group-containing distillation residues, as they are or dissolved in one or more of the abovementioned polyisocyanates, which are obtained in the course of the industrial preparation of isocyanates. It is additionally possible to use any desired mixtures of the abovementioned polyisocyanates.

Preferred are 2,4- or 2,6-tolylene diisocyanate and any desired mixtures of these isomers ("TDI"), polyphenyl-polymethylene-polyisocyanates as prepared by aniline-formaldehyde condensation followed by phosgenization ("crude MDI") or polyisocyanates containing carbodiimide, urethane, allophanate, isocyanurate, urea or biuret groups ("modified polyisocyanates").

The polyurethanes can be homogeneous polyurethanes or cellular.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxyvaleric acid, 5-hydroxy-valeric acid, 6-hydroxycaproic acid and cyclic forms thereof; the terms "lactic acid" or "lactide" include L-lactic acid, D-lactic acid, mixtures and dimers thereof, i.e. L-lactide, D-lactide, meso-lactide and any mixtures thereof.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

31. Aqueous emulsions of natural or synthetic rubber, e.g. natural latex or latices of carboxylated styrene/butadiene copolymers.

An oligohydroxy compound possesses two or more hydroxyl groups, but is not a polymer according to the definition for polymers of the Organization for Economic Cooperation and Development. Examples for oligohydroxy compounds are ethylene glycol, propylene glycol, butane-1,2-diol, butane-1,4-diol, hexane-1,2-diol, hexane-1,6-diol, cyclohexane-1,2-diol, glycerol, pentaerythritol, D-fructose, D-glucitol, mannitol or saccharose.

A wax is for example an ester of wax acids with alcohols, for example $C_{22}$-$C_{34}$-monocarboxylic acids esterified with $C_{15}$-$C_{36}$-monoalcohols, triterpene alcohols or steriod alcohol. Such esters are for example contained in carnauba wax, beeswax or jojo-baoil. A further type of wax is for example a Fischer-Tropsch-wax, which is based on $C_1$-chemistry.

A fat is an ester of glycerol and an aliphatic saturated or unsaturated carboxylic acid, for example a monoacyl glycerol, a diacyl glycerol or a triacyl glycerol. Preferably, the carboxylic acid is linear. Preferably, the carboxylic acid is a $C_8$-$C_{22}$-carboxylic acid.

A mineral oil is an aliphatic liquid saturated hydrocarbon, which is obtained by distillation from crude oil, coal tar, bituminous tar, wood or peat. The mineral oil can be liquid, semi-solid or solid. In the latter case, it is called mineral fat. Examples for mineral oils are benzine, diesel oil, fuel oil, bitumen or kerosine. Preferred mineral oils are saturated $C_8$-$C_{22}$-hydrocarbons, which are linear or branched. Especially preferred are saturated $C_8$-$C_{14}$-hydrocarbons.

Preferred is a composition, which comprises
a) an organic material susceptible to oxidative, thermal or light-induced degradation, wherein the organic material is a polymer, an oligohydroxy compound, a wax, a fat or a mineral oil, and
b) a compound of formula I-P, I-O or I-M.

Preferred is a composition, which comprises
a) an organic material susceptible to oxidative, thermal or light-induced degradation, wherein the organic material is a polymer, in particular a synthetic or semisynthetic polymer and very particular a synthetic or semisynthetic thermoplastic polymer, and
b) a compound of formula I-P, I-O or I-M.

Preferred is a composition, which comprises
a) an organic material susceptible to oxidative, thermal or light-induced degradation, wherein the organic material is a polymer, which is a polyolefin or a copolymer thereof, a polystyrene or a copolymer thereof, a polyurethane or a copolymer thereof, a polyether, which is obtainable by the polymerization of an epoxide, an oxetane or tetrahydrofuran, or a copolymer thereof, a polyester or a copolymer thereof, a polycarbonate or a copolymer thereof, a poly(vinyl chloride) or a copolymer thereof, a poly(vinylidene chloride) or a copolymer thereof, a polysulfone or a copolymer thereof, a polybutadiene or a copolymer thereof, a poly(vinyl acetate) or a copolymer thereof, a poly(vinyl alcohol) or a copolymer thereof, a poly(vinyl acetal) or a copolymer thereof, or a polyamide or a copolymer thereof, and b) a compound of formula I-P, I-O or I-M.

Preferred is a composition, which comprises
a) an organic material susceptible to oxidative, thermal or light-induced degradation, wherein the organic material is a polyolefin or a copolymer thereof, a polystyrene or a copolymer thereof, or a polyurethane or a copolymer thereof, in particular wherein the organic material is a polyolefin or a copolymer thereof, a polystyrene or a copolymer thereof, or a polyurethane or a copolymer thereof, and very particular wherein the organic material is a polyolefin or a copolymer thereof, or a polystyrene or a copolymer thereof, and
b) a compound of formula I-P, I-O or I-M.

Preferred is a composition, which comprises
a) an organic material susceptible to oxidative, thermal or light-induced degradation, wherein the organic material is a polyolefin or a copolymer thereof, and
b) a compound of formula I-P, I-O or I-M.

Preferences for a compound of formula I-P, I-O or I-M in the aforementioned compositions are as following:

Preferred is a compound of formula I-P, I-O or I-M, wherein
$R^4$ and $R^6$ are hydrogen, and
$R^5$ and $R^7$ are independently from each other hydrogen or $C_1$-$C_8$-alkyl, in particular hydrogen or $C_1$-$C_4$-alkyl.

Preferred is a compound of formula I-P, I-O or I-M, wherein
$R^4$, $R^6$ and $R^7$ are hydrogen and $R^5$ is hydrogen or $C_1$-$C_8$-alkyl, in particular hydrogen or $C_1$-$C_4$-alkyl.

Preferred is a compound of formula I-P, I-O or I-M, wherein
$R^{P2}$ and $R^{P6}$ are independently from each other hydrogen or $C_1$-alkyl, $R^{P3}$ and $R^{P5}$ are independently from each other hydrogen or $C_1$-$C_4$-alkyl,
$R^{O1}$ and $R^{O6}$ are independently from each other hydrogen or $C_1$-$C_8$-alkyl, $R^{O2}$ is hydrogen or C-alkyl and $R^{O5}$ is hydrogen or $C_1$-$C_4$-alkyl,
$R^{M1}$ is hydrogen or $C_1$-alkyl, $R^{M3}$ and $R^{M5}$ are independently from each other hydrogen or $C_1$-$C_4$-alkyl, and $R^{M6}$ is hydrogen or $C_1$-$C_8$-alkyl.

Preferred is a compound of formula I-P, I-O or I-M, wherein
$R^{P2}$ and $R^{P6}$ are hydrogen and $R^{P3}$ and $R^{P5}$ are independently from each other hydrogen or $C_1$-$C_4$-alkyl,
$R^{O1}$ is hydrogen or $C_1$-$C_8$-alkyl, $R^{O2}$ is hydrogen, $R^{O5}$ and $R^{O6}$ are independently from each other hydrogen or $C_1$-$C_4$-alkyl,
$R^{M1}$ and $R^{M3}$ are hydrogen or $C_1$-alkyl, $R^{M5}$ is hydrogen or $C_1$-$C_4$-alkyl, and $R^{M6}$ is hydrogen or $C_1$-$C_8$-alkyl.

Preferred is a compound of formula I-P, I-O or I-M, wherein
$R^{P2}$ and $R^{P6}$ are hydrogen and $R^{P3}$ and $R^{P5}$ are independently from each other hydrogen or $C_1$-$C_4$-alkyl, wherein one of $R^{P3}$ and $R^{P5}$ is not $C_4$-alkyl,
$R^{O1}$ is hydrogen or $C_1$-$C_8$-alkyl, $R^{O2}$ is hydrogen, $R^{O5}$ is hydrogen or $C_1$-$C_3$-alkyl, and $R^{O6}$ is hydrogen or $C_1$-$C_4$-alkyl, and
$R^{M1}$ and $R^{M3}$ are hydrogen or $C_1$-alkyl, $R^{M5}$ is hydrogen or $C_1$-$C_3$-alkyl, and $R^{M6}$ is hydrogen or $C_1$-$C_8$-alkyl.

Preferred is a compound of formula I-P, I-O or I-M, wherein
$R^{P2}$ and $R^{P6}$ are hydrogen and one of $R^{P3}$ and $R^{P5}$ is hydrogen, whereas the other one is hydrogen or $C_1$-$C_4$-alkyl,
$R^{O1}$ is hydrogen or $C_1$-$C_8$-alkyl, $R^{O2}$ is hydrogen, $R^{O5}$ is hydrogen or $C_1$-alkyl, and $R^{O6}$ is hydrogen or $C_1$-$C_4$-alkyl, and
$R^{M1}$, $R^{M3}$ and $R^{M5}$ are hydrogen, and $R^{M6}$ is hydrogen or $C_1$-$C_8$-alkyl.

Preferred is a compound of formula I-P, I-O or I-M, wherein
$R^{a1}$, $R^{a2}$, $R^{a3}$ and $R^{a4}$ are independently from each other hydrogen or $C_1$-$C_4$-alkyl,
$R^{b1}$, $R^{b2}$, $R^{b3}$, $R^{b4}$, $R^{b5}$ and $R^{b6}$ are independently from each other hydrogen or $C_1$-$C_4$-alkyl, and
$R^{c1}$, $R^{c2}$, $R^{c3}$ and $R^{c4}$ are independently from each other hydrogen or $C_1$-$C_4$-alkyl.

Preferred is a compound of formula I-P, I-O or I-M, wherein
$R^{a1}$, $R^{a2}$, $R^{a3}$ and $R^{a4}$ are independently from each other hydrogen or $C_1$-$C_4$-alkyl,
$R^{b1}$, $R^{b2}$, $R^{b3}$, $R^{b4}$ are independently from each other hydrogen or $C_1$-$C_4$-alkyl, and one of $R^{b5}$ and $R^{b6}$ is $C_1$-$C_4$-alkyl, whereas the other one is hydrogen, and
$R^{c1}$, $R^{c2}$, $R^{c3}$ and $R^{c4}$ are independently from each other hydrogen or $C_1$-$C_4$-alkyl.

Preferred is a compound of formula I-P, I-O or I-M, wherein
$Y^P$, $Y^O$ and $Y^M$ are oxygen or represent a covalent bond;
when $Y^P$, $Y^O$ and $Y^M$ are oxygen,
  $R^{1P}$ represents one of the subformulae II-P, II-O or II-M,
  $R^{1O}$ represents one of the subformulae II-O or II-M,
  $R^{1M}$ represents the subformula II-M, or
  $R^{1P}$ together with $R^{2P}$, $R^{1O}$ together with $R^{2O}$ and $R^{1M}$ together with $R^{2M}$ represent one of the subformulae III, IV or V, or
  $R^{1P}$, $R^{1O}$ and $R^{1M}$ are $C_6$-$C_{10}$-aryl, which is unsubstituted or substituted by $C_1$-$C_8$-alkyl, $C_1$-$C_{18}$-alkyl, $C_3$-$C_{16}$-cycloalkyl or $C_2$-$C_{18}$-alkenyl, and
  $R^{2P}$ represents one of the subformulae II-P, II-O or II-M,
  $R^{2O}$ represents one of the subformulae II-O or II-M,
  $R^{2M}$ represents the subformula II-M, or
  $R^{2P}$ together with $R^{1P}$, $R^{2O}$ together with $R^{1O}$ and $R^{2M}$ together with $R^{1M}$ represent one of the subformulae III, IV or V, or
  $R^{2P}$, $R^{2O}$ and $R^{2M}$ are $C_6$-$C_{10}$-aryl, which is unsubstituted or substituted by $C_1$-$C_8$-alkyl, $C_1$-$C_{18}$-alkyl, $C_3$-$C_{16}$-cycloalkyl or $C_2$-$C_{18}$-alkenyl;
when $Y^P$, $Y^O$ and $Y^M$ represent a covalent bond,
  $R^{1P}$ represents one of the subformulae II-P, II-O or II-M,
  $R^{1O}$ represents one of the subformulae II-O or II-M,
  $R^{1M}$ represents the subformula II-M, or
  $R^{1P}$, $R^{1O}$ and $R^{1M}$ are $C_6$-$C_{12}$-aryl, which is unsubstituted or substituted by $C_1$-$C_8$-alkyl, $C_1$-$C_{18}$-alkyl, $C_3$-$C_{16}$-cycloalkyl or $C_2$-$C_{18}$-alkenyl, and
  $R^{2P}$, $R^{2O}$ and $R^{2M}$ are $C_6$-$C_{10}$-aryl, which is unsubstituted or substituted by $C_1$-$C_8$-alkyl, or halogen, which is chloro or fluoro.

Preferred is a compound of formula I-P, I-O or I-M, wherein
$Y^P$, $Y^O$ and $Y^M$ are oxygen or represent a covalent bond;
when $Y^P$, $Y^O$ and $Y^M$ are oxygen,
  $R^{1P}$ represents the subformula II-P,
  $R^{1O}$ represents the formulae II-O,
  $R^{1M}$ represents the subformula II-M, or R$^{1P}$ together with R$^{2P}$, R$^{1O}$ together with R$^{2O}$ and R$^{1M}$ together with R$^{2M}$ represent one of the subformulae III, IV or V, or R$^{1P}$, R$^{1O}$ and R$^{1M}$ are C$_6$-C$_{10}$-aryl, which is unsubstituted or substituted by C$_1$-C$_8$-alkyl, C$_1$-C$_{18}$-alkyl, C$_3$-C$_{16}$-cycloalkyl or C$_2$-C$_{18}$-alkenyl, and R$^{2P}$ represents the subformula II-P, R$^{2O}$ represents the subformula II-O, R$^{2M}$ represents the subformula II-M, or R$^{2P}$ together with R$^{1P}$, R$^{2O}$ together with R$^{1O}$ and R$^{2M}$ together with R$^{1M}$ represent one of the subformulae III, IV or V, or R$^{2P}$, R$^{2O}$ and R$^{2M}$ are C$_6$-C$_{10}$-aryl, which is unsubstituted or substituted by C$_1$-C$_8$-alkyl, C$_1$-C$_{18}$-alkyl, C$_3$-C$_{16}$-cycloalkyl or C$_2$-C$_{18}$-alkenyl;

when Y$^P$, Y$^O$ and Y$^M$ represent a covalent bond,

R$^{1P}$ represents the subformula II-P,

R$^{1O}$ represents the subformulae II-O,

R$^{1M}$ represents the subformula II-M, or

R$^{1P}$, R$^{1O}$ and R$^{1M}$ are C$_6$-C$_{10}$-aryl, which is unsubstituted or substituted by C$_1$-C$_8$-alkyl, C$_1$-C$_{18}$-alkyl, C$_3$-C$_{16}$-cycloalkyl or C$_2$-C$_{18}$-alkenyl, and R$^{2P}$, R$^{2O}$ and R$^{2M}$ are C$_6$-C$_{10}$-aryl, which is unsubstituted or substituted by C$_1$-C$_8$-alkyl, or halogen, which is chloro or fluoro.

Preferred is a compound of formula I-P, I-O or I-M, wherein

Y$^P$, Y$^O$ and Y$^M$ are oxygen or represent a covalent bond;

when Y$^P$, Y$^O$ and Y$^M$ are oxygen,

R$^{1P}$ represents the subformula II-P,

R$^{1O}$ represents the formulae II-O,

R$^{1M}$ represents the subformula II-M, or

R$^{1P}$ together with R$^{2P}$, R$^{1O}$ together with R$^{2O}$ and R$^{1M}$ together with R$^{2M}$ represent one of the subformulae III, IV or V, or R$^{1P}$, R$^{1O}$ and R$^{1M}$ are C$_6$-C$_{10}$-aryl, which is unsubstituted or substituted by C$_1$-C$_8$-alkyl, C$_1$-C$_{18}$-alkyl, C$_3$-C$_{16}$-cycloalkyl or C$_2$-C$_{18}$-alkenyl, and R$^{2P}$ is R$^{1P}$, R$^{2O}$ is R$^{1O}$, R$^{2M}$ is R$^{1M}$, or R$^{2P}$ together with R$^{1P}$, R$^{2O}$ together with R$^{1O}$ and R$^{2M}$ together with R$^{1M}$ represent one of the subformulae III, IV or V;

when Y$^P$, Y$^O$ and Y$^M$ represent a covalent bond,

R$^{1P}$ represents the subformula II-P,

R$^{1O}$ represents the subformulae II-O,

R$^{1M}$ represents the subformula II-M, and

R$^{2P}$, R$^{2O}$ and R$^{2M}$ are C$_6$-C$_{10}$-aryl, which is unsubstituted or substituted by C$_1$-C$_8$-alkyl, or halogen, which is chloro or fluoro.

Preferred is a compound of formula I-P, I-O or I-M, wherein

Y$^P$, Y$^O$ and Y$^M$ are oxygen or represent a covalent bond;

when Y$^P$, Y$^O$ and Y$^M$ are oxygen,

R$^{1P}$ represents one of the subformulae II-P, II-O or II-M,

R$^{1O}$ represents one of the subformulae II-O or II-M,

R$^{1M}$ represents the subformula II-M, or

R$^{1P}$ together with R$^{2P}$, R$^{1O}$ together with R$^{2O}$ and R$^{1M}$ together with R$^{2M}$ represent one of the subformulae III, IV or V, or R$^{1P}$, R$^{1O}$ and R$^{1M}$ are C$_6$-C$_{10}$-aryl, which is unsubstituted or substituted by C$_1$-C$_8$-alkyl, C$_1$-C$_{18}$-alkyl or C$_3$-C$_{16}$-cycloalkyl, and R$^{2P}$ represents one of the subformulae II-P, II-O or II-M, R$^{2O}$ represents one of the subformulae II-O or II-M, R$^{2M}$ represents the subformula II-M, or R$^{2P}$ together with R$^{1P}$, R$^{2O}$ together with R$^{1O}$ and R$^{2M}$ together with R$^{1M}$ represent one of the subformulae III, IV or V, or R$^{2P}$, R$^{2O}$ and R$^{2M}$ are C$_6$-C$_{10}$-aryl, which is unsubstituted or substituted by C$_1$-C$_8$-alkyl, C$_1$-C$_{18}$-alkyl or C$_3$-C$_{16}$-cycloalkyl;

when Y$^P$, Y$^O$ and Y$^M$ represent a covalent bond,

R$^{1P}$ represents one of the subformulae II-P, II-O or II-M,

R$^{1O}$ represents one of the subformulae II-O or II-M,

R$^{1M}$ represents the subformula II-M, or

R$^{1P}$, R$^{1O}$ and R$^{1M}$ are C$_6$-C$_{10}$-aryl, which is unsubstituted or substituted by C$_1$-C$_8$-alkyl, C$_1$-C$_{18}$-alkyl or C$_3$-C$_{16}$-cycloalkyl, and R$^{2P}$, R$^{2O}$ and R$^{2M}$ are C$_6$-C$_{10}$-aryl, which is unsubstituted or substituted by C$_1$-C$_8$-alkyl, or fluoro.

Preferred is a compound of formula I-P, I-O or I-M, wherein

Y$^P$, Y$^O$ and Y$^M$ are oxygen or represent a covalent bond;

when Y$^P$, Y$^O$ and Y$^M$ are oxygen,

R$^{1P}$ represents one of the subformulae II-P, II-O or II-M,

R$^{1O}$ represents one of the subformulae II-O or II-M,

R$^{1M}$ represents the subformula II-M, or

R$^{1P}$ together with R$^{2P}$, R$^{1O}$ together with R$^{2O}$ and R$^{1M}$ together with R$^{2M}$ represent the subformula III, or R$^{1P}$, R$^{1O}$ and R$^{1M}$ are C$_6$-C$_{10}$-aryl, which is unsubstituted or substituted by C$_1$-C$_8$-alkyl, or C$_1$-C$_{18}$-alkyl, and R$^{2P}$ represents one of the subformulae II-P, II-O or II-M, R$^{2O}$ represents one of the subformulae II-O or II-M, R$^{2M}$ represents the subformula II-M, or R$^{2P}$ together with R$^{1P}$, R$^{2O}$ together with R$^{1O}$ and R$^{2M}$ together with R$^{1M}$ represent the subformula III, or R$^{2P}$, R$^{2O}$ and R$^{2M}$ are C$_6$-C$_{10}$-aryl, which is unsubstituted or substituted by C$_1$-C$_8$-alkyl, or C$_1$-C$_{18}$-alkyl;

when Y$^P$, Y$^O$ and Y$^M$ represent a covalent bond,

R$^{1P}$ represents one of the subformulae II-P, II-O or II-M,

R$^{1O}$ represents one of the subformulae II-O or II-M,

R$^{1M}$ represent the subformula or II-M, or

R$^{1P}$, R$^{1O}$ and R$^{1M}$ are C$_6$-C$_{10}$-aryl, which is unsubstituted or substituted by C$_1$-C$_8$-alkyl, or C$_1$-C$_{18}$-alkyl, and R$^{2P}$, R$^{2O}$ and R$^{2M}$ are C$_6$-C$_{10}$-aryl, which is unsubstituted or substituted by C$_1$-C$_8$-alkyl, or fluoro.

Preferred is a compound of formula I-P, I-O or I-M, which is of formula I-P or I-O, wherein Y$^P$ and Y$^O$ are oxygen or represent a covalent bond;

when Y$^P$ and Y$^O$ are oxygen,

R$^{1P}$, R$^{2P}$, R$^{1O}$ or R$^{2O}$ does not represent the subformula III-M;

when Y$^P$ and Y$^O$ represent a covalent bond,

R$^{1P}$ or R$^{1O}$ does not represent the subformula II-M.

Preferred is a compound of formula I-P, I-O or I-M, which is of formula I-P, wherein Y$^P$ is oxygen or represents a covalent bond;

when Y$^P$ is oxygen,

R$^{1P}$ or R$^{2P}$ does not represent the subformulae II-O or II-M;

when Y$^P$ represents a covalent bond,

R$^{1P}$ does not represent the subformulae II-O or II-M.

Preferred is a compound of formula I-P, I-O or I-M, wherein

Y$^P$, Y$^O$ and Y$^M$ are oxygen or represent a covalent bond;

when Y$^P$, Y$^O$ and Y$^M$ are oxygen,

R$^{1P}$ represents one of the subformulae II-P, II-O or II-M,

R$^{1O}$ represents one of the subformulae II-O or II-M,

R$^{1M}$ represents the subformula II-M, or

R$^{1P}$, R$^{1O}$ and R$^{1M}$ are C$_6$-C$_{10}$-aryl, which is unsubstituted or substituted by C$_1$-C$_8$-alkyl, C$_1$-C$_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2P}$ represents one of the subformulae II-P, II-O or II-M, $R^{2O}$ represents one of the subformulae II-O or II-M, $R^{2M}$ represents the subformula II-M, or $R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;

when $Y^P$, $Y^O$ and $Y^M$ represent a covalent bond, $R^{1P}$ represents one of the subformulae II-P, II-O or II-M, $R^{1O}$ represents one of the subformulae II-O or II-M, $R^{1M}$ represents the subformula II-M, or $R^{1P}$, $R^{1O}$ and $R^{1M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, or halogen.

Preferred is a compound of formula I-P, I-O or I-M, wherein $Y^P$, $Y^O$ and $Y^M$ are oxygen.

Preferred is a compound of formula I-P, I-O or I-M, which is of formula I-P or I-O, wherein $Y^P$ and $Y^O$ are oxygen, and $R^{1P}$, $R^{2P}$, $R^{1O}$ or $R^{2O}$ does not represent the subformula II-M.

Preferred is a compound of formula I-P, I-O or I-M, wherein $Y^P$, $Y^O$ and $Y^M$ are oxygen, $R^{1P}$ together with $R^{2P}$, $R^{1O}$ together with $R^{2O}$ and $R^{1M}$ together with $R^{2M}$ represent one of the subformulae III, IV or V, and $R^{2P}$ together with $R^{1P}$, $R^{2O}$ together with $R^{1O}$ and $R^{2M}$ together with $R^{1M}$ represent one of the subformulae III, IV or V.

Preferred is a compound of formula I-P or I-O, wherein $Y^P$ and $Y^O$ are oxygen, $R^{1P}$ together with $R^{2P}$ and $R^{1O}$ together with $R^{2O}$ represent one of the subformulae III, IV or V, and $R^{2P}$ together with $R^{1P}$ and $R^{2O}$ together with $R^{1O}$ represent one of the subformulae III, IV or V.

Preferred is a compound of formula I-P, wherein $Y^P$ is oxygen, and $R^{1P}$ together with $R^{2P}$ represent one of the subformulae III, IV or V.

Preferred is a compound of formula I-P, wherein $Y^P$ is oxygen, and $R^{1P}$ together with $R^{2P}$ represent the subformula IV.

The above cited preferences for a compound of formula I-P, I-O or I-M refer individually to three structural units of formula I-P, I-O or I-M. These structural units comprise the benzofuran-2-one unit including $R^4$, $R^5$, $R^6$ and $R^7$, the linking phenylene unit including $R^{P2}$, $R^{P3}$, $R^{P5}$, $R^{P6}$, $R^{O1}$, $R^{O2}$, $R^{O5}$, $R^{O6}$, $R^{M1}$, $R^{M3}$, $R^{M5}$ and $R^{M6}$, and the other-close-to-phosphorus atom unit including $R^{1P}$, $R^{2P}$, $R^{1O}$, $R^{2O}$, $R^{1M}$ and $R^{2M}$ with substituents for subformulae III, IV or V, i.e. $R^{a1}$, $R^{a2}$, $R^{a3}$, $R^{a4}$, $R^{b1}$, $R^{b2}$, $R^{b3}$, $R^{b4}$, $R^{b5}$, $R^{b6}$, $R^{c1}$, $R^{c2}$, $R^{c3}$ and $R^{c4}$. The above cited preferences for the three structural units can be combined. Examples thereof are provided below.

Preferred is a compound of formula I-P, I-O or I-M, wherein $Y^P$, $Y^O$ and $Y^M$ are oxygen or represent a covalent bond;

when $Y^P$, $Y^O$ and $Y^M$ are oxygen, $R^{1P}$ represents one of the subformulae II-P, II-O or II-M, $R^{1O}$ represents one of the subformulae II-O or II-M, $R^{1M}$ represents the subformula II-M, or $R^{1P}$ together with $R^{2P}$, $R^{1O}$ together with $R^{2O}$ and $R^{1M}$ together with $R^{2M}$ represent one of the subformulae III, IV or V, or $R^{1P}$, $R^{1O}$ and $R^{1M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2P}$ represents one of the subformulae II-P, II-O or II-M, $R^{2O}$ represents one of the subformulae II-O or II-M, $R^{2M}$ represents the subformula II-M, or $R^{2P}$ together with $R^{1P}$, $R^{2O}$ together with $R^{1O}$ and $R^{2M}$ together with $R^{1M}$ represent one of the subformulae III, IV or V, or $R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;

when $Y^P$, $Y^O$ and $Y^M$ represent a covalent bond, $R^{1P}$ represents one of the subformulae II-P, II-O or II-M, $R^{1O}$ represents one of the subformulae II-O or II-M, $R^{1M}$ represents the subformula II-M, or $R^{1P}$, $R^{1O}$ and $R^{1M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2P}$, $R^{2O}$ and $R^{2M}$ are $C_6$-$C_{10}$-aryl, which is unsubstituted or substituted by $C_1$-$C_5$-alkyl, $C_1$-$C_8$-alkoxy, halogen or one phenyl, or halogen;

$R^4$ and $R^6$ are hydrogen, $R^5$ and $R^7$ are independently from each other hydrogen or $C_1$-$C_8$-alkyl, $R^{P2}$ and $R^{P6}$ are independently from each other hydrogen or $C_1$-alkyl, $R^{P3}$ and $R^{P5}$ are independently from each other hydrogen or $C_1$-$C_4$-alkyl, $R^{O1}$ and $R^{O6}$ are independently from each other hydrogen or $C_1$-$C_8$-alkyl, $R^{O2}$ is hydrogen or $C_1$-alkyl, $R^{O5}$ is hydrogen or $C_1$-$C_4$-alkyl, $R^{M1}$ is hydrogen or $C_1$-alkyl, $R^{M3}$ and $R^{M5}$ are independently from each other hydrogen or $C_1$-$C_4$-alkyl, $R^{M6}$ is hydrogen or $C_1$-$C_8$-alkyl, $R^{a1}$, $R^{a2}$, $R^{a3}$ and $R^{a4}$ are independently from each other hydrogen or $C_1$-$C_4$-alkyl, $R^{b1}$, $R^{b2}$, $R^{b3}$, $R^{b4}$, $R^{b5}$ and $R^{b6}$ are independently from each other hydrogen or $C_1$-$C_4$-alkyl, and $R^{c1}$, $R^{c2}$, $R^{c3}$ and $R^{c4}$ are independently from each other hydrogen or $C_1$-$C_4$-alkyl.

Preferred is a compound of formula I-P, I-O or I-M, wherein
$Y^P$, $Y^O$ and $Y^M$ are oxygen or represent a covalent bond;
when $Y^P$, $Y^O$ and $Y^M$ are oxygen,
$R^{1P}$ represents one of the subformulae II-P, II-O or II-M,
$R^{1O}$ represents one of the subformulae II-O or II-M,
$R^{1M}$ represent the subformula II-M, or
$R^{1P}$ together with $R^{2P}$, $R^{1O}$ together with $R^{2O}$ and $R^{1M}$ together with $R^{2M}$ represent one of the subformulae III, IV or V, or
$R^{1P}$, $R^{1O}$ and $R^{1M}$ are $C_6$-$C_{10}$-aryl, which is unsubstituted or substituted by $C_1$-$C_8$-alkyl, $C_1$-$C_{18}$-alkyl, or $C_3$-$C_{16}$-cycloalkyl, and
$R^{2P}$ represents one of the subformulae II-P, 11-0 or II-M,
$R^{2O}$ represents one of the subformulae II-O or II-M,
$R^{2M}$ represents the subformula II-M, or
$R^{2P}$ together with $R^{1P}$, $R^{2O}$ together with $R^{1O}$ and $R^{2M}$ together with $R^{1M}$ represent one of the subformulae III, IV or V, or
$R^{2P}$, $R^{2O}$ and $R^{2M}$ are $C_6$-$C_{10}$-aryl, which is unsubstituted or substituted by $C_1$-$C_8$-alkyl, $C_1$-$C_{18}$-alkyl or $C_3$-$C_{16}$-cycloalkyl;
when $Y^P$, $Y^O$ and $Y^M$ represent a covalent bond,
$R^{1P}$ represents one of the subformulae II-P, II-O or II-M,
$R^{1O}$ represents one of the subformulae II-O or II-M,
$R^{1M}$ represents the subformula II-M, or
$R^{1P}$, $R^{1O}$ and $R^{1M}$ are $C_6$-$C_{10}$-aryl, which is unsubstituted or substituted by $C_1$-$C_8$-alkyl, $C_1$-$C_{18}$-alkyl or $C_3$-$C_{16}$-cycloalkyl, and
$R^{2P}$, $R^{2O}$ and $R^{2M}$ are $C_6$-$C_{10}$-aryl, which is unsubstituted or substituted by $C_1$-$C_8$-alkyl, or fluoro;
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{O1}$, $R^{O2}$, $R^{O5}$ and $R^{O6}$ are independently from each other hydrogen or $C_1$-$C_8$-alkyl,
$R^{M1}$, $R^{M3}$, $R^{M5}$ and $R^{M6}$ are independently from each other hydrogen or $C_1$-$C_8$-alkyl,
$R^{a1}$, $R^{a2}$, $R^{a3}$ and $R^{a4}$ are independently from each other hydrogen or $C_1$-$C_8$-alkyl,
$R^{b1}$, $R^{b2}$, $R^{b3}$, $R^{b4}$, $R^{b5}$ and $R^{b6}$ are independently from each other hydrogen or $C_1$-$C_8$-alkyl, and
$R^{c1}$, $R^{c2}$, $R^{c3}$ and $R^{c4}$ are independently from each other hydrogen or $C_1$-$C_8$-alkyl.

Preferred is a compound of formula I-P, I-O or I-M, which is of formula I-P or I-O, wherein
$Y^P$ and $Y^O$ are oxygen or represent a covalent bond;
when $Y^P$ and $Y^O$ are oxygen,
$R^{1P}$ represents one of the subformulae II-P or II-O,
$R^{1O}$ represents the subformulae II-O, or
$R^{1P}$ together with $R^{2P}$ and $R^{1O}$ together with $R^{2O}$ represent one of the subformulae III, IV or V, or
$R^{1P}$ and $R^{1O}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom,
$R^{2P}$ represents one of the subformulae II-P or II-O,
$R^{2O}$ represents the subformulae II-O, or
$R^{2P}$ together with $R^{1P}$ and $R^{2O}$ together with $R^{1O}$ represent one of the subformulae III, IV or V, or
$R^{2P}$ and $R^{2O}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;
when $Y^P$ and $Y^O$ represent a covalent bond,
$R^{1P}$ represents one of the subformulae II-P or II-O,
$R^{1O}$ represents the subformula II-O, or
$R^{1P}$ and $R^{1O}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom,
$R^{2P}$ and $R^{2O}$ are $C_6$-$C_{10}$-aryl, which is unsubstituted or substituted by $C_1$-$C_8$-alkyl, $C_1$-$C_8$-alkoxy, halogen or one phenyl, or halogen;
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{O1}$, $R^{O2}$, $R^{O5}$ and $R^6$ are independently from each other hydrogen or $C_1$-$C_8$-alkyl,
$R^{a1}$, $R^{a2}$, $R^{a3}$ and $R^{a4}$ are independently from each other hydrogen or $C_1$-$C_8$-alkyl,
$R^{b1}$, $R^{b2}$, $R^{b3}$, $R^{b4}$, $R^{b5}$ and $R^{b6}$ are independently from each other hydrogen or $C_1$-$C_8$-alkyl, and
$R^{c1}$, $R^{c2}$, $R^{c3}$ and $R^{c4}$ are independently from each other hydrogen or $C_1$-$C_8$-alkyl.

Preferred is a compound of formula I-P, I-O or I-M, which is of formula I-P or I-O, wherein
$Y^P$ and $Y^O$ are oxygen or represent a covalent bond;
when $Y^P$ and $Y^O$ are oxygen,
$R^{1P}$ represents one of the subformulae II-P or II-O,
$R^{1O}$ represents the subformula II-O, or
$R^{1P}$ together with $R^{2P}$ and $R^{1O}$ together with $R^{2O}$ represent the subformula III, or
$R^{1P}$ and $R^{1O}$ are $C_6$-$C_{10}$-aryl, which is unsubstituted or substituted by $C_1$-$C_8$-alkyl, or $C_1$-$C_{18}$-alkyl,
$R^{2P}$ represents one of the subformulae II-P or II-O,
$R^{2O}$ represents the subformula II-O, or
$R^{2P}$ together with $R^{1P}$ and $R^{2O}$ together with $R^{1O}$ represent the subformula III, or
$R^{2P}$ and $R^{2O}$ are $C_6$-$C_{10}$-aryl, which is unsubstituted or substituted by $C_1$-$C_8$-alkyl, or $C_1$-$C_{18}$-alkyl;
when $Y^P$ and $Y^O$ represent a covalent bond,
$R^{1P}$ represents one of the subformulae II-P or II-O,
$R^{1O}$ represents the subformula II-O, or
$R^{1P}$ and $R^{o1}$ are $C_6$-$C_{10}$-aryl, which is unsubstituted or substituted by $C_1$-$C_8$-alkyl, or $C_1$-$C_{18}$-alkyl,
$R^{2P}$ and $R^{2O}$ are $C_6$-$C_{10}$-aryl, which is unsubstituted or substituted by $C_1$-$C_8$-alkyl, or fluoro;
$R^4$ and $R^6$ are hydrogen,
$R^5$ and $R^7$ are independently from each other hydrogen or $C_1$-$C_8$-alkyl,
$R^{P2}$ and $R^{P6}$ are hydrogen,
$R^{P3}$ and $R^{P5}$ are independently from each other hydrogen or $C_1$-$C_4$-alkyl, wherein one of
$R^{P3}$ and $R^{P5}$ is not $C_4$-alkyl,
$R^{O1}$ is hydrogen or $C_1$-$C_8$-alkyl,
$R^{O2}$ is hydrogen,
$R^{O5}$ is hydrogen or $C_1$-$C_3$-alkyl,
$R^{O6}$ is hydrogen or $C_1$-$C_4$-alkyl,
$R^{a1}$, $R^{a2}$, $R^{a3}$ and $R^{a4}$ are independently from each other hydrogen or $C_1$-$C_4$-alkyl,
$R^{b1}$, $R^{b2}$, $R^{b3}$, $R^{b4}$, $R^{b5}$ and $R^{b6}$ are independently from each other hydrogen or $C_1$-$C_4$-alkyl, and
$R^{c1}$, $R^{c2}$, $R^{c3}$ and $R^{c4}$ are independently from each other hydrogen or $C_1$-$C_4$-alkyl.

Preferred is a compound of formula I-P, I-O or I-M, wherein
$Y^P$, $Y^O$ and $Y^M$ are oxygen or represent a covalent bond;
when $Y^P$, $Y^O$ and $Y^M$ are oxygen,
$R^{1P}$ represents one of the subformulae II-P, II-O or II-M
$R^{1O}$ represents one of the subformulae II-O or II-M,
$R^{1M}$ represents the subformula II-M, or
$R^{1P}$, $R^{1O}$ and $R^{1M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom,
$R^{2P}$ represents one of the subformulae II-P, II-O or III-M,
$R^{2O}$ represents one of the subformulae II-O or II-M,
$R^{2M}$ represents the subformula II-M, or
$R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;
when $Y^P$, $Y^O$ and $Y^M$ represent a covalent bond,
$R^{1P}$ represents one of the subformulae III-P, II-O or II-M,
$R^{1O}$ represents one of the subformulae II-O or II-M,
$R^{1M}$ represents the subformula II-M, or
$R^{1P}$, $R^{1O}$ and RIM are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom,
$R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, or halogen;
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{O1}$, $R^{O2}$, $R^{O5}$ and $R^{O6}$ are independently from each other hydrogen or $C_1$-$C_8$-alkyl, and
$R^{M1}$, $R^{M3}$, $R^{M5}$ and $R^{M6}$ are independently from each other hydrogen or $C_1$-$C_8$-alkyl.

Preferred is a compound of formula I-P, I-O or I-M, wherein
$Y^P$, $Y^O$ and $Y^M$ are oxygen,
$R^{1P}$ together with $R^{2P}$, $R^{1O}$ together with $R^{2O}$ and $R^{1M}$ together with $R^{2M}$ represent one of the subformulae III, IV or V,
$R^{2P}$ together with $R^{1P}$, $R^{2O}$ together with $R^{1O}$ and $R^{2M}$ together with $R^{1M}$ represent one of the subformulae III, IV or V,
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{O1}$, $R^{O2}$, $R^{O5}$ and $R^{O6}$ are independently from each other hydrogen or $C_1$-$C_8$-alkyl,
$R^{M1}$, $R^{M3}$, $R^{M5}$ and $R^{M6}$ are independently from each other hydrogen or $C_1$-$C_8$-alkyl,
$R^{a1}$, $R^{a2}$, $R^{a3}$ and $R^{a4}$ are independently from each other hydrogen or $C_1$-$C_8$-alkyl,
$R^{b1}$, $R^{b2}$, $R^{b3}$, $R^{b4}$, $R^{b5}$ and $R^{b6}$ are independently from each other hydrogen or $C_1$-$C_8$-alkyl, and
$R^{c1}$, $R^{c2}$, $R^{c3}$ and $R^{c4}$ are independently from each other hydrogen or $C_1$-$C_8$-alkyl.

Preferred is a compound of formula I-P or I-O, wherein
$Y^P$ and $Y^O$ are oxygen,
$R^{1P}$ together with $R^{2P}$ and $R^{1O}$ together with $R^{2O}$ represent one of the subformulae III, IV or V,
$R^{2P}$ together with $R^{1P}$ and $R^{2O}$ together with $R^{1O}$ represent one of the subformulae III, IV or V,
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{O1}$, $R^{O2}$, $R^{O5}$ and $R^{O6}$ are independently from each other hydrogen or $C_1$-$C_8$-alkyl,
$R^{a1}$, $R^{a2}$, $R^{a3}$ and $R^{a4}$ are independently from each other hydrogen or $C_1$-$C_8$-alkyl,
$R^{b1}$, $R^{b2}$, $R^{b3}$, $R^{b4}$, $R^{b5}$ and $R^{b6}$ are independently from each other hydrogen or $C_1$-$C_8$-alkyl, and
$R^{c1}$, $R^{c2}$, $R^{c3}$ and $R^{c4}$ are independently from each other hydrogen or $C_1$-$C_8$-alkyl.

Preferred is a compound of formula I-P, wherein
$Y^P$ is oxygen,
$R^{1P}$ together with $R^{2P}$ represent one of the subformulae III, IV or V,
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{a1}$, $R^{a2}$, $R^{a3}$ and $R^{a4}$ are independently from each other hydrogen or $C_1$-$C_8$-alkyl,
$R^{b1}$, $R^{b2}$, $R^{b3}$, $R^{b4}$, $R^{b5}$ and $R^{b6}$ are independently from each other hydrogen or $C_1$-$C_8$-alkyl, and
$R^{c1}$, $R^{c2}$, $R^{c3}$ and $R^{c4}$ are independently from each other hydrogen or $C_1$-$C_8$-alkyl.

Preferred is a compound of formula I-P, wherein
$Y^P$ is oxygen,
$R^{1P}$ together with $R^{2P}$ represent the subformula IV,
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl, and
$R^{b1}$, $R^{b2}$, $R^{b3}$, $R^{b4}$, $R^{b5}$ and $R^{b6}$ are independently from each other hydrogen or $C_1$-$C_8$-alkyl.

Preferred is a compound of formula I-P, which is compound (103), (104), (105), (107), (108) or (109), or a compound of formula I-O, which is compound (101), (102) or (106). The structures of these compounds are depicted in the respective synthetic examples S-1 to S-9.

The employed amount of component b), i.e. a compound of formula I-P, I-O or I-M, in regard to component a), i.e. an organic material susceptible to oxidative, thermal or light-induced degradation, varies with the particular organic material susceptible to oxidative, thermal or light-induced degradation and the desired degree of protection.

Preferred is a composition, which comprises an organic material susceptible to oxidative, thermal or light-induced degradation as component a) and a compound of formula I-P, I-O or I-M as component b), wherein component b) is contained in an amount of 0.0005% to 10%, in particular from 0.001% to 2%, especially from 0.005% to 1%, based on the weight of component a).

Optionally, a composition comprising an organic material as component a) and a compound of formula I-P, I-O or I-M as component b) contains a further additive as component c).

A further additive can be selected from the following list:
1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclo-hexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol, 2,4-dimethyl-6-(1'-methyl-1'-tetradecyl-methyl)-phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-di methylbenzyl mercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, for example with methanol, ethanol, n-octanol, i-octanol, a mixture of linear and branched $C_7$-$C_9$-alkanol, octadecanol, a mixture of linear and branched $C_{13}$-$C_{15}$-alkanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxylethyl)isocyanurate, N,N'-bis-(hydroxyl-ethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, for example with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl) propionic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.16. Esters of 3,5-di-tert-butyl-4-hydroxyphenyl acetic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, for example N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]-propionyloxy)ethyl]oxamide (Naugard XL-1 ®, supplied by Uniroyal).

1.18. Ascorbic acid (vitamin C)

1.19. Aminic antioxidants, for example N,N'-di-isopropyl-p-phenylenediamine, N,N'-disec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N, N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N, N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

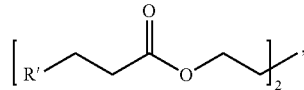

where R'=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline and neopentyl tetra(α-cyano-β,β-diphenylacrylate).

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2, 2,6,6-tetramethyl-4-piperidyl)-1,2,3,4-butanetetracarboxylate, 1,1'-(1,2-ethanediyl)-bis(3,3,5,5-tetra-methylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperid-4-yl) sebacate, bis(1-octyloxy-2,2,6,6-tetramethylpiperid-4-yl) succinate, bis-[2,2,6,6-tetramethyl-1-(undecyloxy) piperidin-4-yl] carbonate, linear or cyclic condensates of N,N'-bis(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268 64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5] decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, a mixture of oligomeric compounds which are the formal condensation products of N,N'-bis-(2,2,6,6-tetramethyl-1-propoxy-piperidin-4-yl)-hexane-1,6-diamine and 2,4-dichloro-6-{n-butyl (2,2,6,6-tetramethyl-1-propoxy-piperidin-4-yl)-amino}-[1,3,5]triazine end-capped with 2-chloro-4,6-bis-(di-n-butylamino)-[1,3,5]triazine, a mixture of oligomeric compounds which are the formal condensation products of N,N'-bis-(2,2,6,6-tetramethyl-piperidin-4-yl)-hexane-1,6-diamine and 2,4-dichloro-6-{n-butyl-(2,2,6,6-tetramethyl-piperidin-4-yl)amino}-[1,3,5]triazine end-capped with 2-chloro-4,6-bis-(di-n-butylamino)[1,3,5]triazine, 2,4-bis [N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)-oxymethyl-3,3,5-trimethyl-2-morpholinone, the reaction product of 2,4-bis-[(1-cyclo-hexyloxy-2,2,6,6-piperidine-4-yl)butylamino]-6-chloro-s-triazine with N,N'bis-(3-amino-propyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy) phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethyl-phenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]-phenyl}-4,6-bis¬(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis (benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, which are different to a compound of formula I-P, 1-0 or I-M, for example triphenyl phosphite, diphenylalkyl phosphites, phenyldialkyl phosphites, tris(nonylphenyl) phosphite, trilauryl phosphite, trioctadecyl phosphite, dis-tearylpentaerythritol diphosphite, tris (2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tertbutylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-ditert-butyl-6-methylphenyl)ethyl phosphite, 6-fluoro-2,4,8,10-tetratert-butyl-12-methyl-dibenz[d,g]-1,3,2-dioxaphosphocin, 2,2',2''-nitrilo[triethyltris(3,3',5,5'-tetra-tert-butyl-1,1'-biphenyl-2,2'-diyl)phosphite], 2-ethylhexyl-(3,3',5,5'-tetra-tert-butyl-1,1'-biphenyl-2,2'-diyl)phosphite, 5-butyl-5-ethyl-2-(2,4,6-tritert-butylphenoxy)-1,3,2-dioxaphosphirane.

The following phosphites are especially preferred:

Tris(2,4-di-tert-butylphenyl) phosphite (Irgafos 168, RTM BASF), tris(nonylphenyl) phosphite,

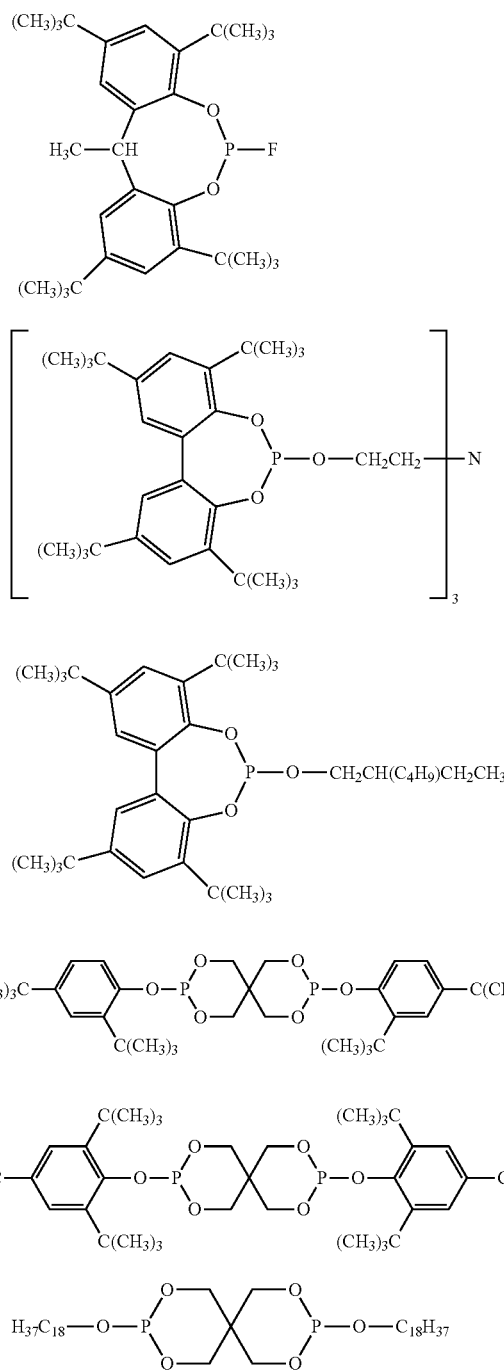

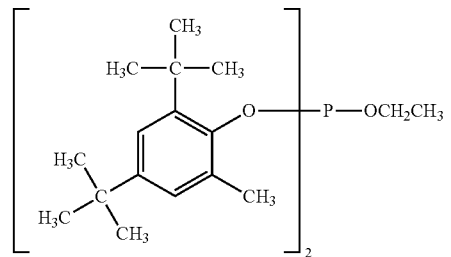

5. Hydroxylamines and amine N-oxides, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine, N,N-bis(hydrogenated rape-oil alkyl)-N-methyl-amine N-oxide or trialkylamine N-oxide.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, Nhexadecyl-alpha-heptadecylnitrone, N-octadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate and pentaerythritol tetrakis-[3-(n-lauryl)-propionic acid ester].

8. Peroxide scavengers, for example esters of α-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Acid scavengers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate and zinc pyrocatecholate.

11. Benzofuranones and indolinones, which are different to a compound of formula I-P, I-O or I-M, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tertbutylbenzofuran-2-one and 3-(2-acetoxy-4-(1,1,3,3-tetramethyl-butyl)-phenyl)-5-(1,1,3,3-tetramethyl-butyl)benzofuran-2-one.

12. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers), Irgaclear XT 386 (RTM BASF), 1,3:2,4-bis(3',4'-dimethylbenzylidene)-sorbitol, 1,3:2,4-di(paramethyldibenzylidene)-sorbitol, and 1,3:2,4-di(benzylidene)sorbitol.

13. Fillers and reinforcing agents, for example calcium carbonate, silicates, glass fibres, glass beads, asbestos, talc, kaolin, bentonite, mica, hydrotalcite, barium sulfate, metal oxides and hydroxides, carbon black, graphite, wood flour and flours or fibers of other natural products, synthetic fibers.

14. Other additives, for example plasticisers, lubricants, rheology additives, catalysts, flow-control agents, optical brighteners, flameproofing agents, antistatic agents and blowing agents.

It has also been surprisingly found that many compounds of formula I-P, I-O or I-M, in combination with a further additive are very effective for stabilization of an organic material against degradation by heat, light and/or oxidation, in particular in combination with a phenolic antioxidant or a phosphite or phosphonite, which is different to a compound of formula I-P, I-O or I-M, as a further additive. It often turns out that the presence of compounds of formula I-P, I-O or I-M allows to reduce the amount of the further additive in excess of a mere 1 to 1 substitution based on weight of the further additive.

Preferred is a composition, which comprises an organic material susceptible to oxidative, thermal or light-induced degradation as component a), a compound of formula I-P, I-O or I-M as component b) and a further additive as component c).

Preferred is a composition, wherein the weight ratio of component b) to component c) is from 10:1 to 1:30, in particular from 4:1 to 1:20, especially from 2:1 to 1:10.

Preferred is a composition, wherein the weight ratio of component b) to component c) is from 10:1 to 1:30, in particular from 4:1 to 1:20, especially from 2:1 to 1:10, and wherein the overall amount of component b) and component c) is below 80%, especially 50%, by weight of component a).

Preferred is a composition, wherein the weight ratio of component b) to component c) is from 10:1 to 1:30, in particular from 4:1 to 1:20, especially from 2:1 to 1:10, and wherein the overall amount of component b) and component c) is between 0.005% and 79%, especially between 0.005% and 49%, by weight of component a).

Preferred is a composition, wherein the weight ratio of component b) to component c) is from 4:1 to 1:20 and the overall amount of component b) and component c) is below 80%, in particular between 0.005% and 49%, based on the weight of component a).

Preferred is a composition, which comprises as component c) a further additive, which is an antioxidant, an UV absorber, a hindered amine light stabilizer, a nickel compound, a metal deactivator, a phosphite or phosphonite, which is different to a compound of formula I-P, I-O or I-M, a hydroxylamine or amine N-oxide, a thiosynergist, a peroxide scavenger, a nucleating agent, a filler or reinforcing agent.

Preferred is a composition, which comprises as component c) a further additive, which is a phosphite or phosphonite, which is different to a compound of formula I-P, I-O or I-M, an acid scavenger, a phenolic antioxidant or an aminic antioxidant.

Preferred is a composition, which comprises
a) an organic material susceptible to oxidative, thermal or light-induced degradation,
b) a compound of formula I-P, I-O or I-M, and
c) a further additive, which is a phenolic antioxidant or a phosphite or phosphonite, which is different to a compound of formula I-P, I-O or I-M.

Preferred is a composition, which comprises as component c) a phenolic antioxidant.

Preferred is a composition, which comprises as component c) a phenolic antioxidant, which is an ester of β-(3,5-di-tert-butyl-4-hydroxyphenyl)propionic acid.

A phenolic antioxidant of special relevance is a compound as depicted

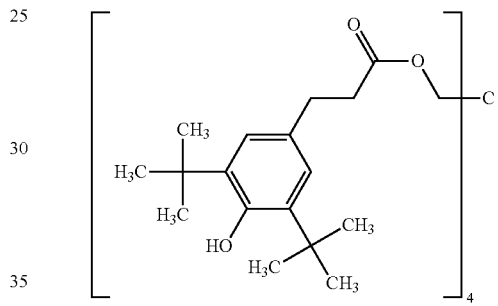

and for which one chemical name is tetrakis-[β-(3,5-di-tert-butyl-4-hydroxyphenyl)propionyloxymethyl]methane or alternatively tetrakis-[3-(3,5-di-tert-butyl-4-hydroxyphenyl)-propionyloxymethyl]methane. It is contained in the commercial product Irganox 1010 (RTM BASF).

Another phenolic antioxidant of special relevance is a compound as depicted

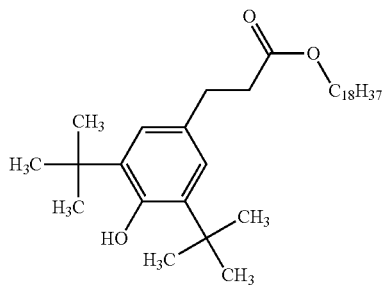

and for which one chemical name is stearyl β-(3,5-di-tert-butyl-4-hydroxyphenyl)propionate or alternatively stearyl 3-(3,5-di-tert-butyl-4-hydroxyphenyl)-propionate. It is contained in the commercial product Irganox 1076 (RTM BASF).

Preferred is a composition, which comprises as component c) a phenolic antioxidant, which is tetrakis-[β-(3,5-di-tert-butyl-4-hydroxyphenyl)-propionyloxymethyl]methane or stearyl β-(3,5-di-tert-butyl-4-hydroxyphenyl)-propionate.

Preferred is a composition, which comprises as component c) a phosphite or phosphonite, which is different to a compound of formula I-P, I-O or I-M.

A phosphite of special relevance is a compound as depicted

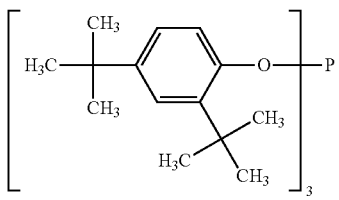

and for which one chemical name is tris-(2,4-di-tert-butylphenyl) phosphite. It is contained in the commercial product Irgafos 168 (RTM BASF).

Preferred is a composition, which comprises as component c) a phosphite, which is tris-(2,4-di-tert-butylphenyl) phosphite.

Optionally, a composition comprising an organic material susceptible to oxidative, thermal or light-induced degradation as component a), a compound of formula I-P, 1-O or I-M as component b) and a further additive as component c) contains a second further additive as component d).

Preferred is a composition, which comprises an organic material susceptible to oxidative, thermal or light-induced degradation as component a), a compound of formula I-P, I-O or I-M as component b), a further additive as component c) and a second further additive as component d).

Preferred is a composition, wherein the weight ratio of component b) to component d) is from 10:1 to 1:30, in particular from 4:1 to 1:20, especially from 2:1 to 1:10.

Preferred is a composition, wherein the weight ratio of component b) to component d) is from 10:1 to 1:30, in particular from 4:1 to 1:20, especially from 2:1 to 1:10, and wherein the overall amount of component b), component c) and component d) is below 50%, in particular between 0.01% and 49%, by weight of component a).

Preferred is a composition, which comprises a component a), a component b), as component c) a further additive, which is selected from the group consisting of a phosphite or phosphonite, which is different to a compound of formula I-P, I-O or I-M, an acid scavenger, a phenolic antioxidant and an aminic antioxidant, and as component d) a second further additive; with the proviso that component d) is a different substance than component c).

Preferred is a composition, which comprises a component a), a component b), a component c) and a component d), wherein component c) and component d) are independently from each other a phosphite or phosphonite, which is different to a compound of formula I-P, I-O or I-M, an acid scavenger, a phenolic antioxidant or an aminic antioxidant; with the proviso that component d) is a different substance than component c).

Preferred is a composition, which comprises a component a), a component b), as component c) a phenolic antioxidant and as component d) an aminic antioxidant.

Preferred is a composition, which comprises a component a), a component b), as component c) a phenolic antioxidant and as component d) a phosphite or phosphonite, which is different to a compound of formula I-P, I-O or I-M.

Preferred is a composition, which comprises
a) an organic material susceptible to oxidative, thermal or light-induced degradation,
b) a compound of formula I-P, I-O or I-M,
c) a further additive, which is a phenolic antioxidant, and
d) a second further additive, which is a phosphite or phosphonite, which is different to a compound of formula I-P, I-O or I-M.

Preferred is a composition, which comprises
a) an organic material susceptible to oxidative, thermal or light-induced degradation,
b) a compound of formula I-P, I-O or I-M,
c) a further additive, which is a phenolic antioxidant, which is tetrakis-[β-(3,5-di-tert-butyl-4-hydroxyphenyl)-propionyloxymethyl]methane or stearyl β-(3,5-di-tert-butyl-4-hydroxyphenyl)-propionate, and
d) a second further additive, which is a phosphite or phosphonite, which is different to a compound of formula I-P, I-O or I-M.

Preferred is a composition, which comprises
a) an organic material susceptible to oxidative, thermal or light-induced degradation,
b) a compound of formula I-P, I-O or I-M,
c) a further additive, which is a phenolic antioxidant, and
d) a second further additive, which is a phosphite, which is tris-(2,4-di-tert-butyl) phosphite.

Preferred is a composition, which comprises
a) an organic material susceptible to oxidative, thermal or light-induced degradation,
b) a compound of formula I-P, I-O or I-M,
c) a further additive, which is a phenolic antioxidant, which is tetrakis-[β-(3,5-di-tert-butyl-4-hydroxyphenyl)-propionyloxymethyl]methane or stearyl β-(3,5-di-tert-butyl-4-hydroxyphenyl)-propionate, and
d) a second further additive, which is a phosphite, which is tris-(2,4-di-tert-butyl) phosphite.

The above described preferences for an organic material susceptible to oxidative, thermal or light-induced degradation as component a) and for a compound of formula I-P, I-O or I-M as component b) are described for a composition. These preferences apply also to the further embodiments of the invention. At these further embodiments, the optional presence of a further additive as component c) and the optional presence of a second further additive as component d) are also included.

A further embodiment of the invention relates to a process for protection of an organic material susceptible to oxidative, thermal or light-induced degradation, i.e. component a), which comprises the steps of
providing the organic material, i.e. component a), and
incorporating into or application onto the provided organic material a compound of formula I-P, I-O or I-M, i.e. component b).

The incorporation or application of component b) can be carried out in a processing apparatus, in particular a heatable container equipped with a stirrer, which can preferably be closed. A heatable container equipped with a stirrer is for example a kneader, extruder, mixer or stirred vessel. Specific examples thereof are a single-screw extruder, contrarotating and corotating twin-screw extruder, planetary-gear extruder, ring extruder or co-kneader. It is also possible to use a processing apparatus, which contains at least one gas removal compartment to which a vacuum can be applied and/or which can be set under an atmosphere, wherein the oxygen content is low or oxygen is absent, for example under a nitrogen atmosphere. Component b) can be added directly into the processing apparatus.

Component b) can be incorporated or applied to at any stage of processing of component a). If component a) is a polymer, the stage is in particular prior to or during a shaping operation of component a) in the processing apparatus.

Component b) can be incorporated or applied in the form of a dry powder, in the form of a melt, in encapsulated form such as encapsulation in a wax or an auxiliary polymer or in the form of a wet mixture such as a solution, a dispersion or a suspension for example in an inert solvent, water or oil. A dispersing or suspension agent can be present in the case of a wet mixture of component b). A further form for incorporation is a granule, for example obtained by compacting a powder of component b).

Component b) can also be incorporated or applied by spraying onto component a).

In case that component a) is a polymer, a further possibility for incorporation or application of component b) to component a) is addition before, during or directly after the polymerization of the corresponding starting materials, e.g. monomers, of component a). For example, spraying during the deactivation of the polymerization catalysts is particularly advantageous. If crosslinking takes place during formation of component a), incorporation or application prior to crosslinking is preferred.

In case that component a) is a polymer, the process of incorporation or application is preferably a molding process, in particular an injection-molding, blow-molding, compression-molding, roto-molding, slush-molding or extrusion-molding.

Preferred is a process, wherein the organic material susceptible to oxidative, thermal or light-induced degradation is a polymer, and which comprises the steps of
　providing the organic material susceptible to oxidation, thermal or light-induced degradation, and
　incorporating of a compound of formula I-P, I-O or I-M into the provided organic material and wherein a part or the complete incorporation takes place at a temperature in the range from 135 to 350° C., preferably from 150° C. to 340° C., in particular from 180° C. 15 to 330° C. and very especially from 190° C. to 320° C.

Preferred is a process, wherein component b) is incorporated or applied to in an extruder during processing of component a), which is a polymer.

In case of a further additive and optionally a second further additive, i.e. component c) or components c) and d), component b) and the further additive or the second further additive can be incorporated into or applied onto component a) individually or mixed with one another. If desired, the individual components can be mixed with one another before incorporation into component a) for example by dry blending, compaction, melting, encapsulation by a wax or by an auxiliary polymer or as wet mixture in the form of solutions, dispersions or suspensions for example in an inert solvent, water or oil.

Component b) and a further additive and optionally a second further additive can also be added to component a) in the form of a masterbatch ('concentrate'), which contains the component b), a further additive, optionally a second further additive and a masterbatch polymer as an auxiliary polymer. The component b) and a further additive and optionally a second further additive are incorporated into the masterbatch in a concentration of, for example, from 1% to 40% and preferably 2% to 20% by weight of the masterbatch. The masterbatch polymer content is the difference towards 100% by weight of the masterbatch. The masterbatch polymer must not be necessarily the same polymer as component a) in case the latter one is a polymer.

A further embodiment of the invention relates to an article, which is made from a composition comprising
a) an organic material susceptible to oxidative, thermal or light-induced degradation, and
b) a compound of formula I-P, I-O or I-M.

The article, which is advantageously made from a composition comprising component a), which is a polymer, and a component b), can be a shaped article. Examples for a shaped article are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike, trucks) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded or co-extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, synthetic (such as Astro-Turf®), artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags. Non-woven fabrics such as medical fabrics and related apparel, industrial apparel, outdoor fabrics, in-home furnishing and construction fabrics.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Preferred is an article, which is a shaped article, which is a film, pipe, profile, bottle, tank, container or fiber.

Preferred is a shaped article, which is molded. In particular, the molding is effected by injection, blow, compression, roto-molding, slush-molding or extrusion.

A further embodiment to the invention relates to the use of a compound of formula I-P, I-O or I-M, i.e. component b), for stabilizing an organic material susceptible to oxidative, thermal or light-induced degradation, i.e. component a), against degradation by oxidation, heat or light.

Preferred is the use of component b) for stabilizing a polyurethane in the form of a foam against scorching.

Preferred is the use of a compound of formula I-P, I-O or I-M in combination with a further additive for stabilizing an organic material susceptible to oxidative, thermal or light-induced degradation against degradation by oxidation, heat or light.

Preferred is the use of a compound of formula I-P, I-O or I-M in combination with a further additive, which is a phenolic antioxidant or a phosphite or phosphonite, which is different to a compound of formula I-P, I-O or I-M, for stabilizing an organic material susceptible to oxidative, thermal or light-induced degradation against degradation by oxidation, heat or light.

Preferred is the use of a compound of formula I-P, I-O or I-M in combination with a further additive, which is a phenolic antioxidant, and a second further additive, which is a phosphite or phosphonite, which is different to a compound of formula I-P, I-O or I-M for stabilizing an organic material susceptible to oxidative, thermal or light-induced degradation against degradation by oxidation, heat or light.

Preferred is the use of a compound of formula I-P, I-O or I-M in combination with a further additive, which is a phenolic antioxidant, and a second further additive, which is a phosphite or phosphonite, which is different to a compound of formula I-P, I-O or I-M, for stabilizing an organic material susceptible to oxidative, thermal or light-induced degradation, which is a polyolefin or a copolymer thereof, against degradation by oxidation, heat or light.

Processing of a component a) is characterized as short-term exposure of the component a) to heat, for example to a temperature in the range of 135° C. to 350° C., in particular from 150° C. to 340° C., during the time of processing of component a). The time of processing is short in comparison to for example the possible time of usage, for example below 1 hour versus above 1 week. Usage takes typically place at a temperature, for example 0° C. to 50° C., which is below the temperature during processing.

Preferred is the use of component b) for stabilizing a component a) against oxidative or thermal degradation during processing.

A further embodiment of the invention relates to a compound of formula I-P, I-O or I-M

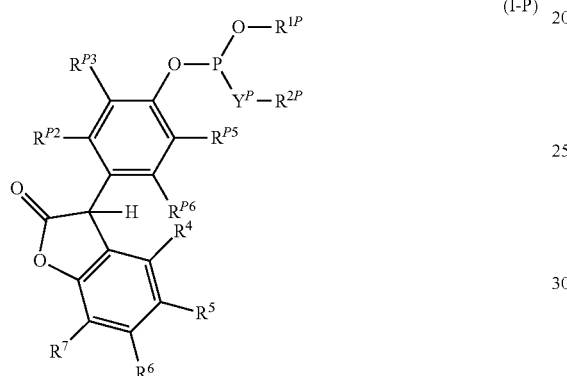
(I-P)

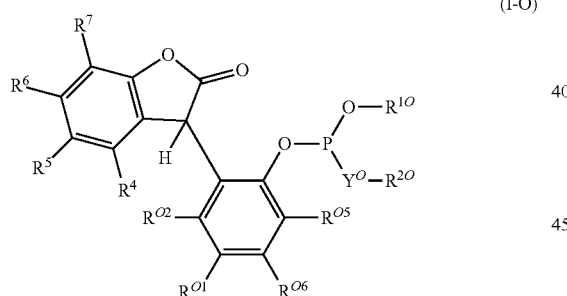
(I-O)

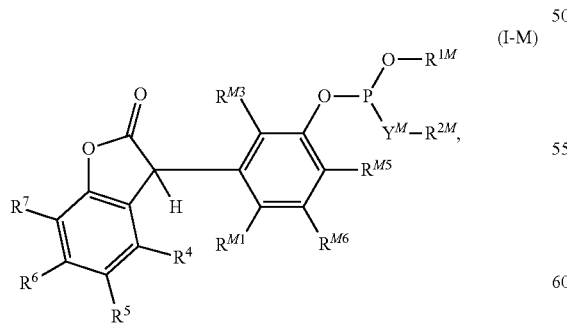
(I-M)

wherein $Y^P$, $Y^O$ and $Y^M$ are oxygen or represent a covalent bond;

when $Y^P$, $Y^O$ and $Y^M$ are oxygen, $R^{1P}$ represents one of the subformulae II-P, II-O or II-M

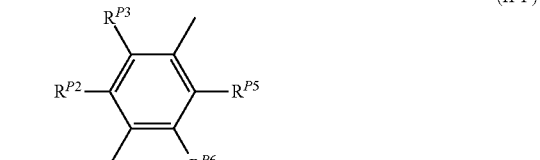
(II-P)

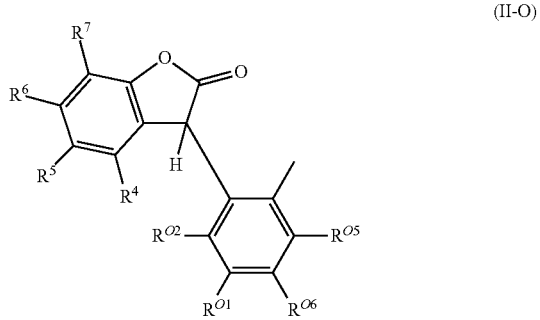
(II-O)

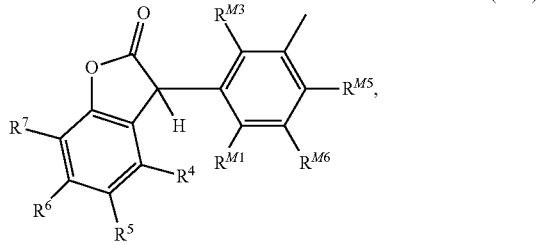
(II-M)

$R^{1O}$ represents one of the subformulae II-O or II-M, $R^{1M}$ represents the subformula II-M, or $R^{1P}$ together with $R^{2P}$, $R^{1O}$ together with $R^{2O}$ and $R^{1M}$ together with $R^{2M}$ represent one of the subformulae III, IV or V

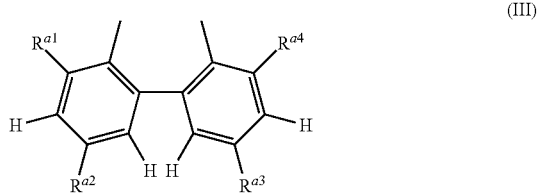
(III)

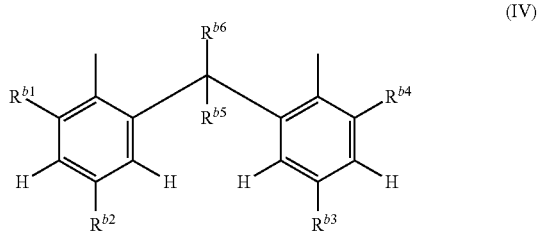
(IV)

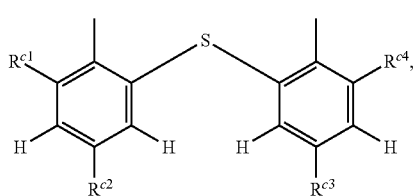
(V)

$R^{1P}$, $R^{1O}$ and $R^{1M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2P}$ represents one of the subformulae II-P, II-O or II-M,
$R^{2O}$ represents one of the subformulae II-O or II-M,
$R^{2M}$ represents the subformula II-M, or
$R^{2P}$ together with $R^{1P}$, $R^{2O}$ together with $R^{1O}$ and $R^{2M}$ together with $R^{1M}$ represent one of the subformulae III, IV or V, or $R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;

when $Y^P$, $Y^O$ and $Y^M$ represent a covalent bond,
$R^{1P}$ represents one of the subformulae II-P, II-O or II-M,
$R^{1O}$ represents one of the subformulae II-O or II-M,
$R^{1M}$ represents the subformula II-M, or
$R^{1P}$, $R^{1O}$ and $R^{1M}$ are $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2P}$, $R^{2O}$ and $R^{2M}$ are $C_6$-$C_{10}$-aryl, which is unsubstituted or substituted by $C_1$-$C_8$-alkyl, $C_1$-$C_8$-alkoxy, halogen or one phenyl, or halogen;

$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{O1}$, $R^{O2}$, $R^{O5}$ and $R^{O6}$ are independently from each other hydrogen or $C_1$-$C_8$-alkyl,
$R^{M1}$, $R^{M3}$, $R^{M5}$ and $R^{M6}$ are independently from each other hydrogen or $C_1$-$C_8$-alkyl,
$R^{a1}$, $R^{a2}$, $R^{a3}$ and $R^{a4}$ are independently from each other hydrogen or $C_1$-$C_8$-alkyl,
$R^{b1}$, $R^{b2}$, $R^{b3}$, $R^{b4}$, $R^{b5}$ and $R^{b6}$ are independently from each other hydrogen or $C_1$-$C_8$-alkyl, and
$R^{c1}$, $R^{c2}$, $R^{c3}$ and $R^{c4}$ are independently from each other hydrogen or $C_1$-$C_8$-alkyl.

A further embodiment of the invention relates to an additive composition, which comprises
b) a compound of formula I-P, I-O or I-M, and
c) a further additive selected from a group consisting of a phosphite or phosphonite, which is different to a compound of formula I-P, I-O or I-M, an acid scavenger, a phenolic antioxidant and an aminic antioxidant.

Preferred is a composition, wherein the weight ratio of component b) to component c) is from 10:1 to 1:30, in particular from 4:1 to 1:20, especially from 2:1 to 1:10.

Preferred is an additive composition, wherein the weight ratio of component b) to component c) is from 10:1 to 1:30, in particular from 4:1 to 1:20, especially from 2:1 to 1:10.

Preferred is an additive composition, which comprises
b) a compound of formula I-P, I-O or I-M, and
c) a further additive, which is a phenolic antioxidant or a phosphite or phosphonite, which is different to a compound of formula I-P, I-O or I-M.

Preferred is an additive composition, which comprises
b) a compound of formula I-P, I-O or I-M, and
c) a further additive, which is a phenolic antioxidant.

Preferred is an additive composition, which comprises
b) a compound of formula I-P, I-O or I-M, and
c) a further additive, which is a phosphite or phosphonite, which is different to a compound of formula I-P, I-O or I-M.

Preferred is an additive composition, which comprises
b) a compound of formula I-P, I-O or I-M, and
c) a further additive, which is tetrakis-[β-(3,5-di-tert-butyl-4-hydroxyphenyl)propionyloxymethyl]methane, stearyl β-(3,5-di-tert-butyl-4-hydroxyphenyl)-propionate or tris-(2,4-di-tert-butyl) phosphite.

Preferred is an additive composition, which comprises as component d) a second further additive.

Preferred is an additive composition, which comprises
b) a compound of formula I-P, I-O or I-M,
c) a further additive selected from a group consisting of a phosphite or phosphonite, which is different to a compound of formula I-P, I-O or I-M, an acid scavenger, a phenolic antioxidant and an aminic antioxidant, and
d) a second further additive selected from a group consisting of a phosphite or phosphonite, which is different to a compound of formula I-P, I-O or I-M, an acid scavenger, a phenolic antioxidant and an aminic antioxidant; with the proviso that component c) is a different substance than component d).

Preferred is a composition, wherein the weight ratio of component b) to component c) is from 10:1 to 1:30, in particular from 4:1 to 1:20, especially from 2:1 to 1:10, and wherein the weight ratio of component b) to component d) is from 10:1 to 1:30, in particular from 4:1 to 1:20, especially from 2:1 to 1:10.

Preferred is an additive composition, wherein the weight ratio of component b) to component c) is from 10:1 to 1:30, in particular from 4:1 to 1:20, especially from 2:1 to 1:10, and wherein the weight ratio of component b) to component d) is from 10:1 to 1:30, in particular from 4:1 to 1:20, especially from 2:1 to 1:10.

Preferred is an additive composition, which comprises
b) a compound of formula I-P, I-O or I-M,
c) a further additive, which is a phenolic antioxidant, and
d) a second further additive, which is a phosphite or phosphonite, which is different to a compound of formula I-P, I-O or I-M.

Preferred is an additive composition, which comprises
b) a compound of formula I,
c) a further additive, which is tetrakis-[β-(3,5-di-tert-butyl-4-hydroxyphenyl)propionyloxymethyl]methane or stearyl β-(3,5-di-tert-butyl-4-hydroxyphenyl)propionate, and
d) a second further additive, which is a phosphite or phosphonite, which is different to a compound of formula I-P, I-O or I-M.

Preferred is an additive composition, which comprises
b) a compound of formula I-P, I-O or I-M,
c) a further additive, which is a phenolic antioxidant, and
d) a second further additive, which is tris-(2,4-di-tert-butyl) phosphite.

Preferred is an additive composition, which comprises
b) a compound of formula I-P, I-O or I-M,
c) a further additive, which is tetrakis-[β-(3,5-di-tert-butyl-4-hydroxyphenyl)propionyloxymethyl]methane or stearyl β-(3,5-di-tert-butyl-4-hydroxyphenyl)propionate, and
d) a second further additive, which is tris-(2,4-di-tert-butyl) phosphite.

A further embodiment of this invention relates to a process for manufacturing a compound of formula I-P, I-O or I-M. The basic synthetic approach for manufacturing is the reaction of a suitable halogen-substituted phosphorus derivative with the respective hydroxy-substituted benzofuranone derivative in the presence of a base and optionally a solvent, especially an aprotic solvent.

Preferred is a process, wherein the base is pyridine, potassium carbonate or sodium carbonate.

An aprotic solvent is for example dichloroethane or toluene.

Preferred is a process for manufacturing a compound of formula I-P

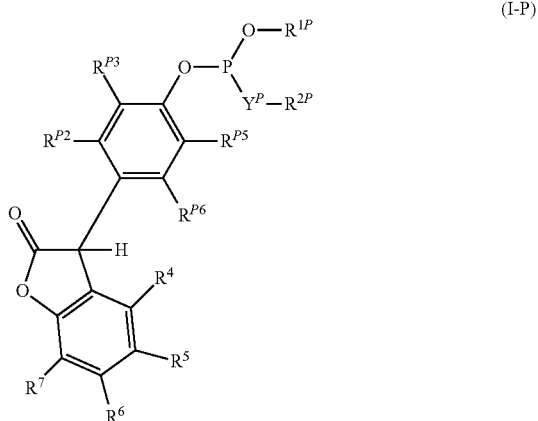
(I-P)

wherein
$Y^P$ is oxygen;
which comprises the steps of
reacting a compound of formula S-IN-P

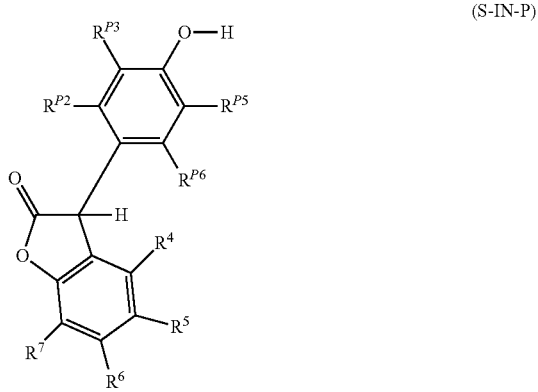
(S-IN-P)

with a compound of formula PS-IN-P

(PS-IN-P)

in the presence of a base and optionally an aprotic solvent to obtain a compound of formula IN-P

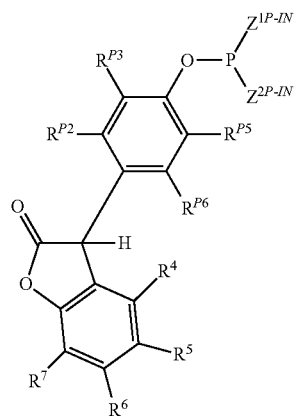
(IN-P)

reacting the compound of formula IN-P with a compound of formula S1-IN-P

HO—$R^{1P}$ (S1-IN-P)

and a compound of formula S2-IN-P

HO—$R^{2P}$ (S2-IN-P)

in the presence of a base and optionally an aprotic solvent to obtain the compound of formula I-P;
wherein
$R^{1P}$ represents one of the subformulae III-P, II-O or II-M,

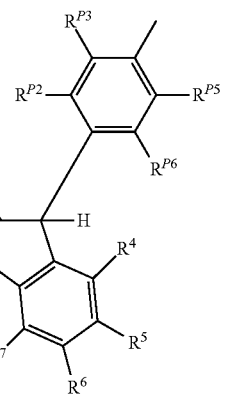
(II-P)

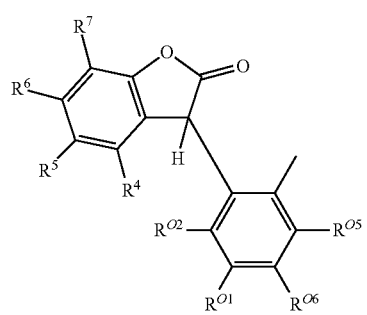
(II-O)

-continued

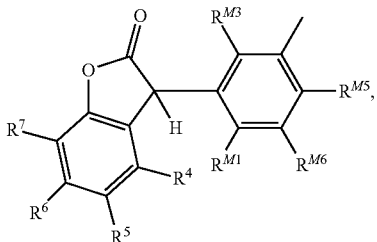

(II-M)

$R^{1P}$ is $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2P}$ represents one of subformulae II-P, II-O or II-M, or $R^{2P}$ is $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;

$R^4$, $R^5$, $R^6$ and $R^7$ are independently from each other hydrogen or $C_1$-$C_5$-alkyl, $R^{P2}$, $R^{P3}$, $R^{P5}$ and $R^{P6}$ are independently from each other hydrogen or $C_1$-$C_8$-alkyl, $R^{O1}$, $R^{O2}$, $R^{O5}$ and $R^{O6}$ are independently from each other hydrogen or $C_1$-$C_8$-alkyl, $R^{M1}$, $R^{M3}$, $R^{M5}$ and $R^{M6}$ are independently from each other hydrogen or $C_1$-$C_8$-alkyl, and $Z^{1P-IN}$, $Z^{2P-IN}$ and $Z^{3P-IN}$ are independently from each other halogen.

Preferred is a process for manufacturing a compound of formula I-O

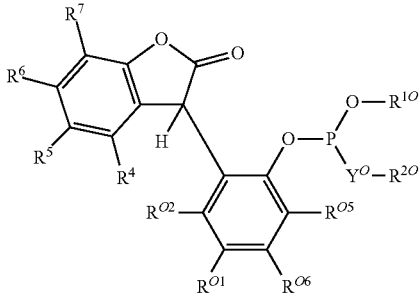

(I-O)

wherein
$Y^O$ is oxygen;
which comprises the steps of
reacting a compound of formula S-IN-O

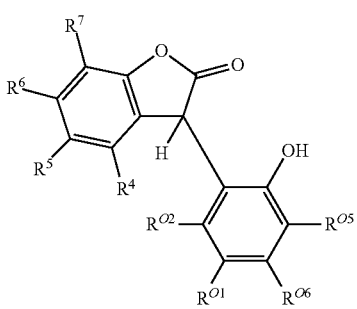

(S-IN-O)

with a compound of formula PS-IN-O

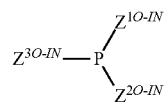

(PS-IN-O)

in the presence of a base and optionally an aprotic solvent to obtain a compound of formula IN-O

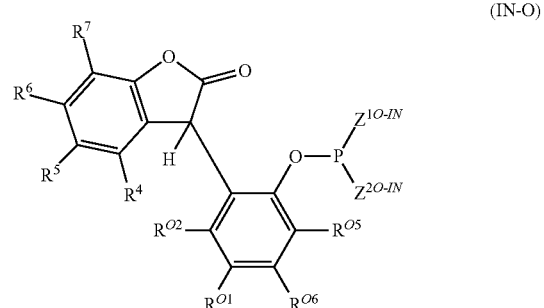

(IN-O)

reacting the compound of formula IN-O with a compound of formula S1-IN-O

HO—$R^{1O}$  (S1-IN-O)

and a compound of formula S2-IN-O

HO—$R^{2O}$  (S2-IN-O)

in the presence of a base and optionally an aprotic solvent to obtain the compound of formula I-O;
wherein
$R^{1O}$ represents one of the subformulae II-O or II-M,

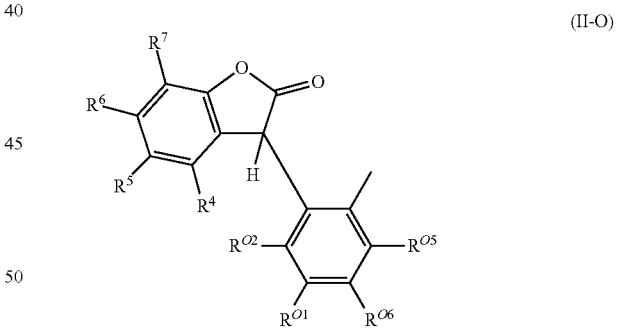

(II-O)

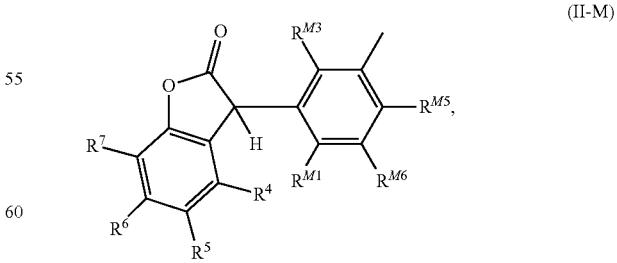

(II-M)

$R^{1O}$ is $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2O}$ represents one of the subformulae II-O or II-M, or $R^{2O}$ is $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;

$R^4$, $R^5$, $R^6$ and $R^7$ are independently from each other hydrogen or $C_1$-$C_8$-alkyl, $R^{O1}$, $R^{O2}$, $R^{O5}$ and $R^{O6}$ are independently from each other hydrogen or $C_1$-$C_8$-alkyl, $R^{M1}$, $R^{M3}$, $R^{M5}$ and $R^{M6}$ are independently from each other hydrogen or $C_1$-$C_8$-alkyl, and $Z^{1O-IN}$, $Z^{2O-IN}$ and $Z^{3O-IN}$ are independently from each other halogen.

Preferred is a process for manufacturing a compound of formula I-M

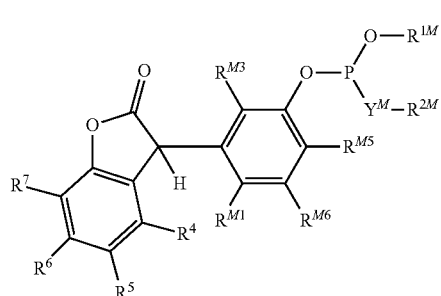
(I-M)

wherein
$Y^M$ is oxygen;
which comprises the steps of
reacting a compound of formula S-IN-M

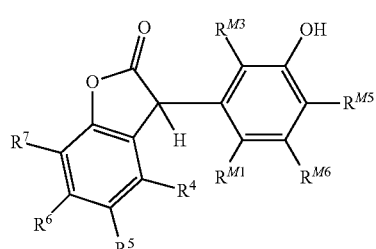
(S-IN-M)

with a compound of formula PS-IN-M

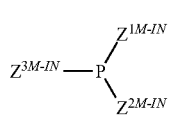
(PS-IN-M)

in the presence of a base and optionally an aprotic solvent to obtain a compound of formula IN-M

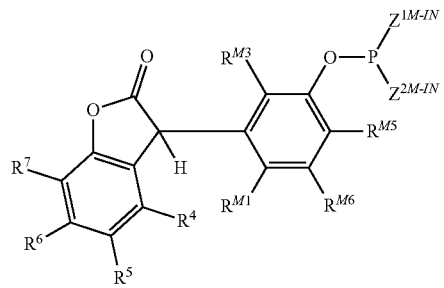
(IN-M)

reacting the compound of formula IN-M with a compound of formula S1-IN-M

HO—$R^{1M}$ (S1-IN-M)

and a compound of formula S2-IN-M

HO—$R^{2M}$ (S2-IN-M)

in the presence of a base and optionally an aprotic solvent to obtain the compound of formula I-M;
wherein
$R^{1M}$ represents the subformula II-M,

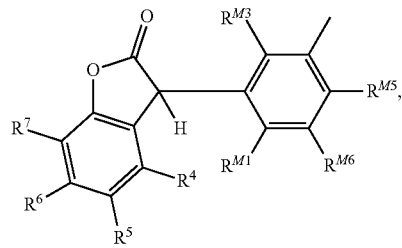
(II-M)

$R^{1M}$ is $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom, $R^{2M}$ represents the subformula II-M, or $R^{2M}$ is $C_6$-$C_{10}$-aryl, which is unsubstituted or substituted by $C_1$-$C_8$-alkyl, $C_1$-$C_8$-alkoxy, halogen or one phenyl, $C_1$-$C_{18}$-alkyl, $C_3$-$C_{16}$-cycloalkyl, $C_7$-$C_{13}$-aralkyl, $C_2$-$C_{18}$-alkenyl, $C_2$-$C_{30}$-alkyl, which is interrupted by one or more oxygen atoms, or $C_2$-$C_{16}$-alkyl, which is interrupted by one sulfur atom;

$R^4$, $R^5$, $R^6$ and $R^7$ are independently from each other hydrogen or $C_1$-$C_8$-alkyl, $R^{M1}$, $R^{M3}$, $R^{M5}$ and $R^{M6}$ are independently from each other hydrogen or $C_1$-$C_8$-alkyl, and $Z^{1M-IN}$, $Z^{2M-IN}$ and $Z^{3M-IN}$ are independently from each other halogen.

The formulae PS-IN-P, PS-IN-O and PS-IN-M are covering the same compounds, but are individualized for clarity in the reaction schemes for a compound of formula I-P, I-O or I-M.

A further embodiment of this invention relates to an intermediate compound of formula IN-P, IN-O or IN-M

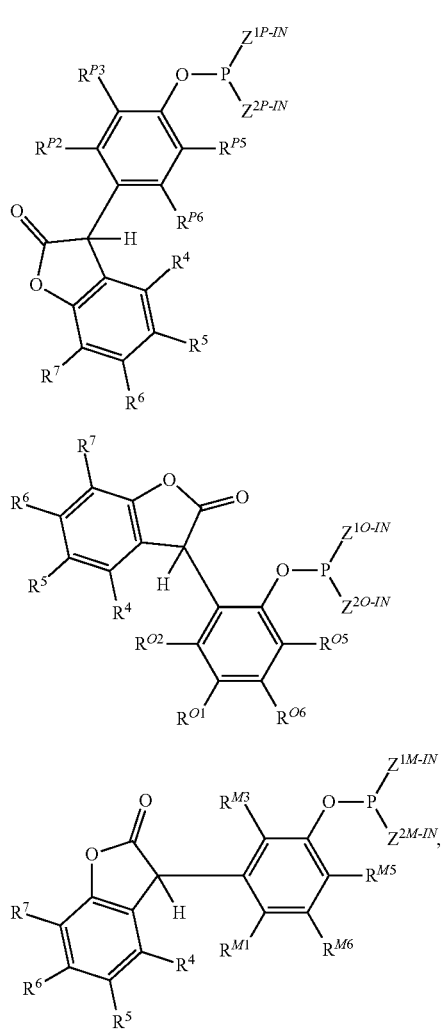

wherein
$Z^{1P-IN}$, $Z^{2P-IN}$, $Z^{1O-IN}$, $Z^{2O-IN}$, $Z^{1M-IN}$ and $Z^{2M-IN}$ are independently from each other halogen,
$R^4$, $R^5$, $R^6$ and $R^7$ are independently from each other hydrogen or $C_1$-$C_8$-alkyl,
$R^{P2}$, $R^{P3}$, $R^{P5}$ and $R^{P6}$ are independently from each other hydrogen or $C_1$-$C_8$-alkyl,
$R^{O1}$, $R^{O2}$, $R^{O5}$ and $R^{O6}$ are independently from each other hydrogen or $C_1$-$C_8$-alkyl, and
$R^{M1}$, $R^{M3}$, $R^{M5}$ and $R^{M6}$ are independently from each other hydrogen or $C_1$-$C_8$-alkyl.

The following examples illustrate further the invention without limiting it. Percentage values are percentage by weight if not stated differently.

SYNTHETIC EXAMPLES

The synthetic procedures are conducted under a nitrogen atmosphere.

If not otherwise stated, the starting materials are commercially available, for example from Aldrich Corp.

Example S-1: Synthesis of Compound (101)

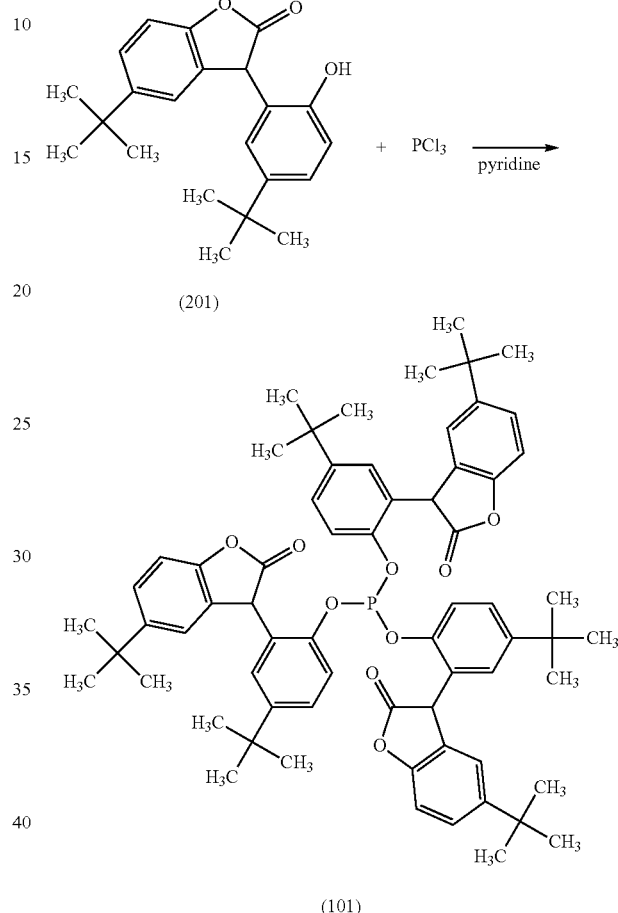

18.6 g (55 mmol) of compound (201) (obtainable according to EP 2500341 A, page 8, example 1) are heated to 65° C. in 85 ml of dry 1,2-dichloroethane. 5.19 g (65 mmol) dry pyridine are added. 2.5 g (18 mmol) phosphorous-trichloride, which are dissolved in 2 mL of dry 1,2-dichloroethane, are added over 20 minutes. The reaction mass is stirred for 2 hours at 65° C. After cooling to ambient temperature, 120 mL cyclohexane are added and the white precipitate formed is filtrated and washed with another 120 mL cyclohexane. The combined cyclohexane portions are concentrated to dryness and the white residue is dried at 70° C. under vacuum for 3 hours. 15.0 g (80% of theory) of compound (101) as a white amorphous solid are obtained.

$^{31}$P-NMR (toluene-$d_8$): 128 ppm $^1$H-NMR (toluene-$d_8$): 4.7 ppm (s, 3H, CH at lactone-ring)

MS (LC/MS, ACPI positive mode): [M+1]$^+$=1044

Example S-2: Synthesis of Compound (102)

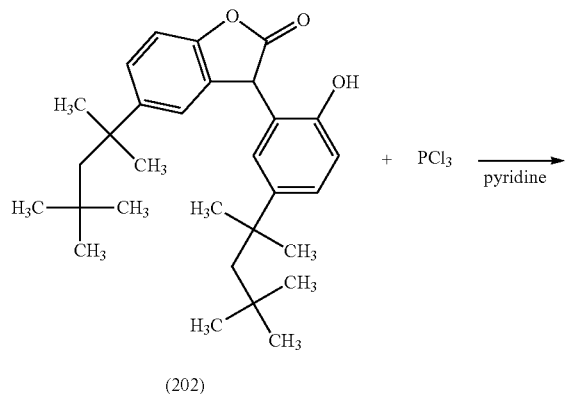

(202)

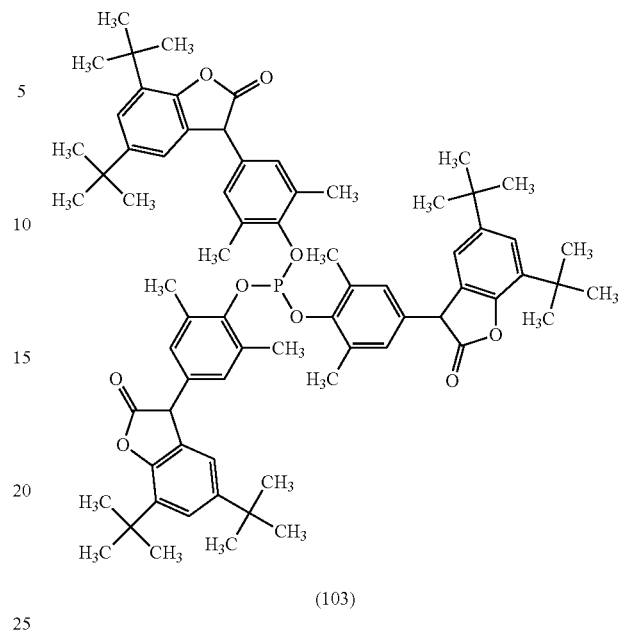

(103)

Compound (103) is prepared in analogy to example 1 from compound (203) (obtainable according to EP 0648765 A, page 30, compound 115) and obtained in a yield of 89% of theory as an amorphous solid.

$^{31}$P-NMR (toluene-d$_8$): 142 ppm $^1$H-NMR (toluene-d$_8$): 4.2 ppm (s, 3H, CH at lactone-ring)

MS (LC/MS, ACPI positive mode): [M+1]+=1128

Example S-4: Synthesis of Compound (104)

(102)

Compound (102) is prepared in analogy to example 1 from compound (202) (obtainable according to EP 2500341 A, page 8, example 1 by using the corresponding 4-tertoctyl-phenol) and obtained in a yield of 71% of theory as an amorphous solid.

$^{31}$P-NMR (toluene-d$_8$): 128 ppm
$^1$H-NMR (toluene-d$_8$): 4.7 ppm (s, 3H, CH at lactone-ring)
MS (LC/MS, ACPI positive mode): [M+1]$^+$=1381

Example S-3: Synthesis of Compound (103)

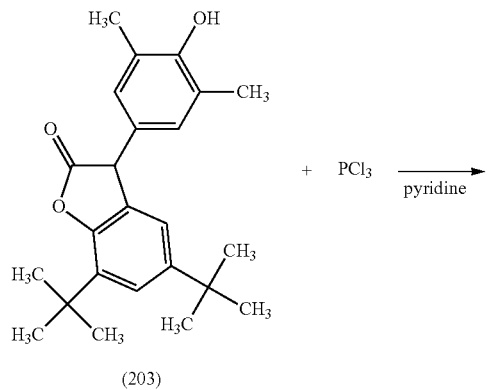

(203)

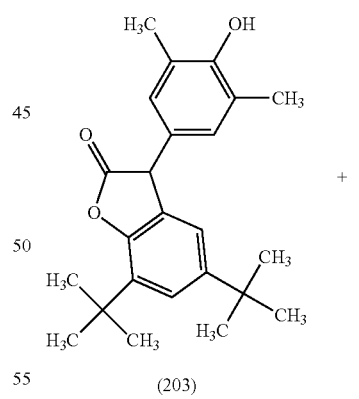

(203)

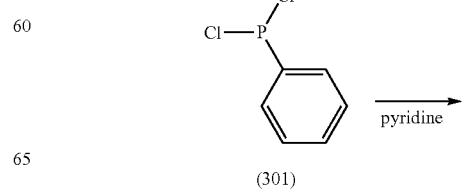

(301)

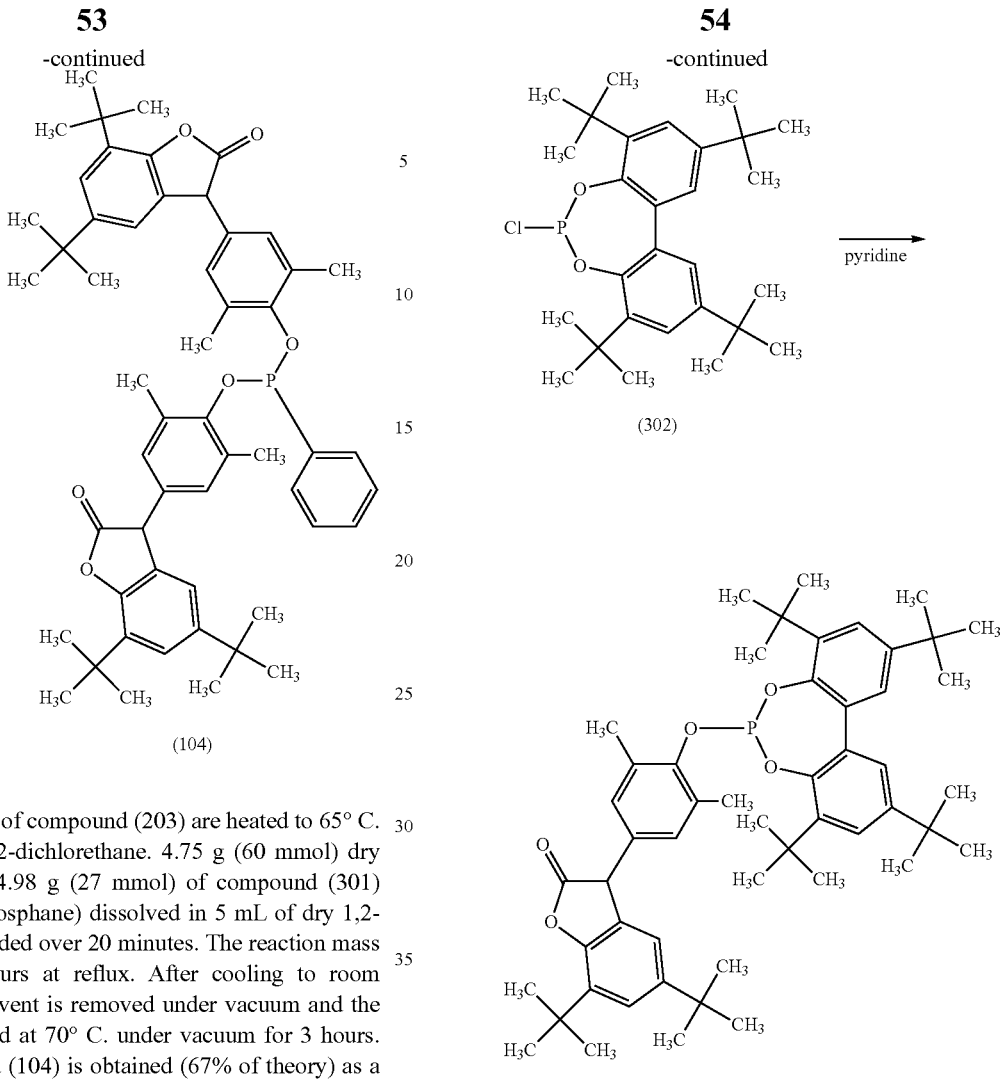

(104)

20.0 g (55 mmol) of compound (203) are heated to 65° C. in 85 mL of dry 1,2-dichlorethane. 4.75 g (60 mmol) dry pyridine is added. 4.98 g (27 mmol) of compound (301) (=dichlorophenylphosphane) dissolved in 5 mL of dry 1,2-dichloroethane is added over 20 minutes. The reaction mass is stirred for 4 hours at reflux. After cooling to room temperature, the solvent is removed under vacuum and the solid residue is dried at 70° C. under vacuum for 3 hours. 15.4 g of compound (104) is obtained (67% of theory) as a white solid.

$^{31}$P-NMR (toluene-ds): 169 ppm $^{1}$H-NMR (toluene-$d_8$): 4.2 ppm (s, 2H, CH at lactone ring)

MS (LC/MS, ACPI positive mode): [M+1]+=840

Example S-5: Synthesis of Compound (105)

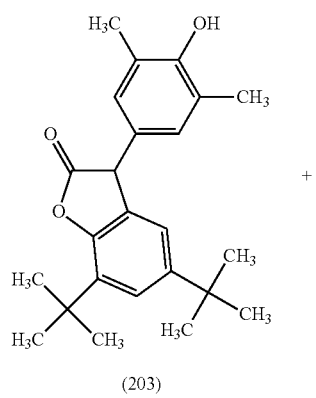

(203)

2.0 g (5 mmol) of compound (203) are dissolved in 10 mL of dry dichloroethane at 65° C. To the solution are subsequently added 0.52 g (7 mmol) of dry pyridine and within 20 minutes 2.59 g (5 mmol) of compound (302) (=2,4,8,10-tetra-t-butyl-6-chlorobenzo[d][1,3,2]benzodioxaphosphepine, obtainable according to U.S. Pat. No. 5,858,905, page 2, example 1). The reaction mass is stirred under reflux for 6 hours, cooled to room temperature and 10 mL of pentane are added. The suspension is filtrated, the residue is washed with 2 portions of 10 mL dichloroethane and the combined solvent fractions are evaporated to dryness under vacuum. The glassy solid residue is further dried at 70° C. in vacuum. 2.92 g of compound (105) are obtained (66% of theory) as a white glassy solid.

$^{31}$P-NMR (toluene-$d_8$): 141 ppm $^{1}$H-NMR (toluene-$d_8$): 4.2 ppm (s, 1H, CH at lactone ring)

MS (LC/MS, ACPI positive mode): [M+1]$^+$=806

Example S-6: Synthesis of Compound (106)
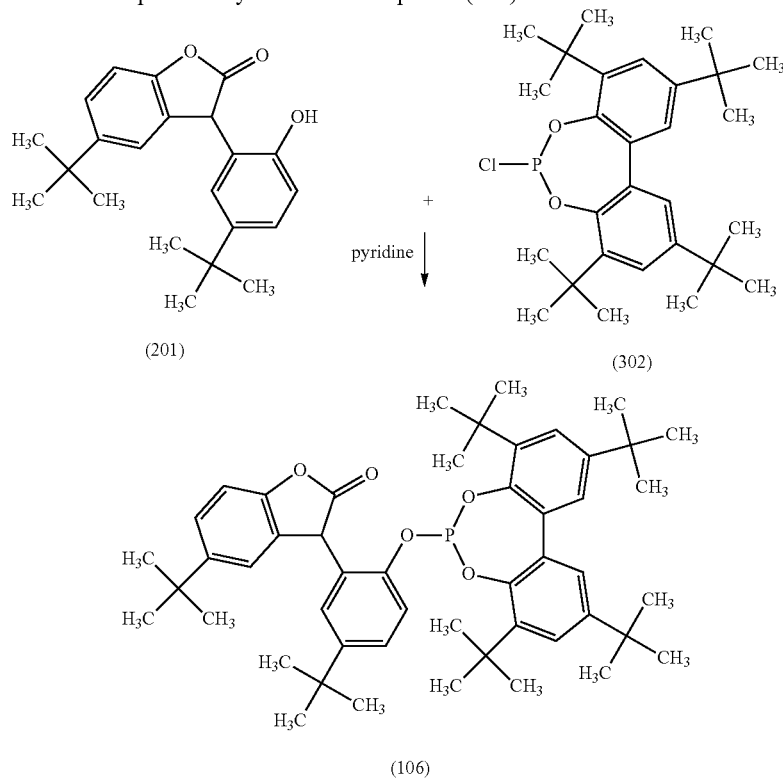
Compound (106) is prepared in analogy to example 5 from compound (201) and compound (302) and obtained in a yield of 82% of theory as a solid.
$^{31}$P-NMR (toluene-d$_8$): 143 ppm
$^1$H-NMR (toluene-d$_8$): 4.8 ppm (s, 1H, CH at lactone ring)
MS (LC/MS, ACPI positive mode): [M+1]$^+$=778
Example S-7: Synthesis of Compound (107)
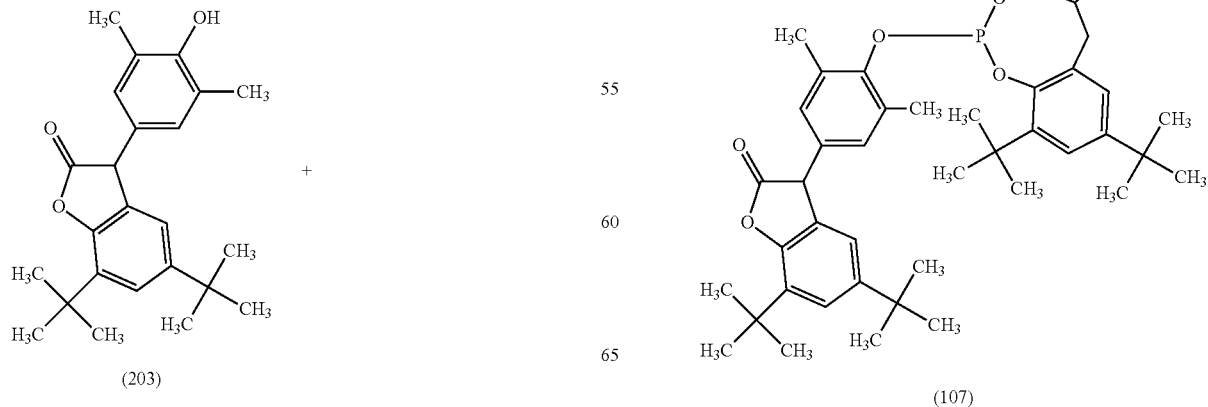

Compound (107) is prepared in analogy to example 5 from compound (203) and compound (303) (=1,3,7,9-tetra-tert-butyl-11-chloro-5H-benzo[d][1,3,2]benzodioxa-phosphocine, obtainable according to U.S. Pat. No. 5,858,905, page 2, example 1) and is obtained in a yield of 87% of theory as a solid.

$^{31}$P-NMR (toluene-d$_8$): 137 ppm
$^1$H-NMR (toluene-ds): 4.3 ppm (s, 1H, CH at lactone ring)
MS (LC/MS, ACPI positive mode): [M+1]$^+$=820

Example S-8: Synthesis of Compound (108)

tert-butyl-11-chloro-5-methyl-5H-benzo[d][1,3,2]benzodi-oxaphosphocine, obtainable according to U.S. Pat. No. 5,858,905, page 2, example 1) and is obtained in a yield of 90% of theory as a solid.

$^{31}$P-NMR (toluene-d$_8$): 138 ppm
$^1$H-NMR (toluene-d$_8$): 4.3 ppm (s, 1H, CH at lactone ring)
MS (LC/MS, ACPI positive mode): [M+1]$^+$=834

Example S-9: Synthesis of Compound (109)

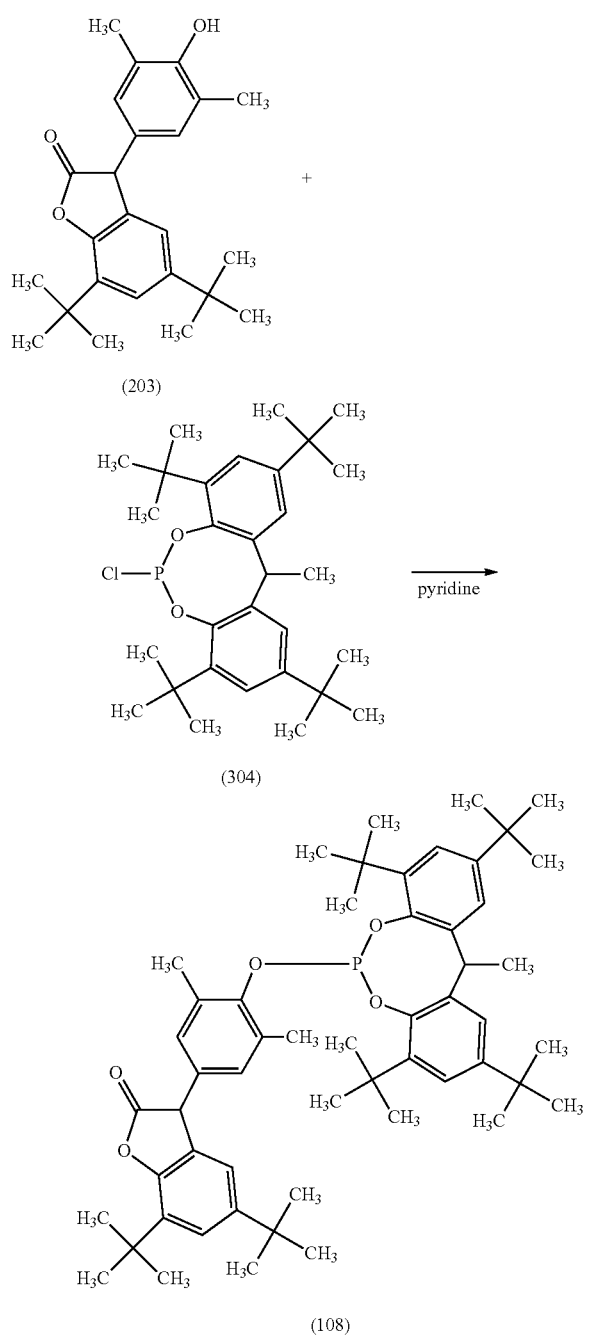

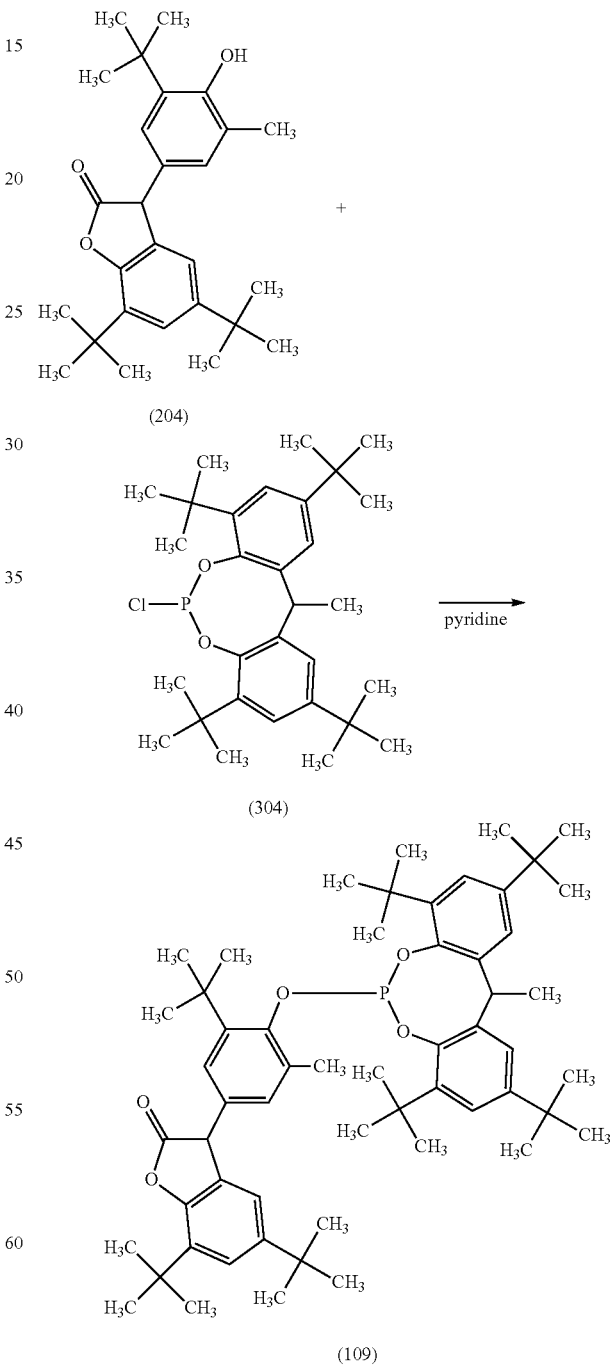

Compound (108) is prepared in analogy to example 5 from compound (203) and compound (304) (=1,3,7,9-tetra- Compound (109) is prepared in analogy to example 5 from compound (204) (obtainable according to EP 0648765

A, page 30, compound 115) and compound (304) and is obtained in a yield of 75% of theory as a solid.

$^{31}$P-NMR (toluene-d$_8$): 137 ppm
$^{1}$H-NMR (toluene-d$_8$): 4.9 ppm (s, 1H, CH at lactone ring)
MS (LC/MS, ACPI positive mode): [M+1]$^+$=876

APPLICATION EXAMPLES

The following known stabilizers are partly employed in addition to the inventive compounds:

AO-1 is Irganox 1010 (RTM BASF), which contains pentaerythritol tetrakis(3-(3,5-di-tert-butyl-4-hydroxyphenyl)propionate).

AO-2 is Irganox 1076 (RTM BASF), which contains octadecyl 3-(3,5-di-tert-butyl-4-hydroxyphenyl) propionate.

Phos-1 is Irgafos 168 (RTM BASF), which contains tris(2,4-di-tert-butylphenyl) phosphite.

CaSt is commercially available calcium stearate, which acts as acid scavenger.

ZnSt is commercially available zinc stearate, which acts as acid scavenger.

ZnO is commercially available zinc oxide, which acts as acid scavenger.

Example A-1: Stabilization of a Molding Grade Ziegler-Natta Polypropylene Homopolymer Polymer Processing Experimental A molding grade Ziegler-Natta polypropylene homopolymer (zn-PP-homopolymer) from a bulk/slurry phase polymerization process is evaluated. The processing conditions are described below. The various additives are blended according to table A-1-1 with the granular polymer, which is essentially free of any stabilization additives. The blending is carried out using a M 10 FU mixer from MTI.

The thoroughly blended formulations are then melt compounded in a single screw extruder (Teach-Line Extruder E20T SCD 15 from Dr. Collin; L/D=25, compression 3.08) at lower temperature of 200° C. under nitrogen, which is denoted in the table A-1-1 as the zero pass extrusion. This ensures good melt mixing with minimal damage to the polymer due to oxidative degradation.

The resultant zero pass extrudate is then extruded multiple times a single screw extruder, fitted with a Maddock mixing section, at higher temperature (280° C.), open to air. Extrusion at higher temperatures in combination with the presence of oxygen (air) enhances the rate of polymer degradation. Pelletized samples of zero, first, third and fifth pass extrudate are collected and stored in sealed plastic bags at room temperature in storage boxes in the dark.

Melt Flow Rates: The samples are tested for retention of molecular mass (weight). This is measured by melt flow rate retention (according to ASTM-1238) on a MD-P melt index tester from Goettfert at the test conditions of 230° C. and 2.16 kg. Melt flow rates are measured in grams of polymer that flow out of a defined orifice in 10 minutes and are stated as grams/10 minutes (decigrams per minute).

TABLE A-1-1

| composition No. | 1 $^{a)}$ | 2 $^{a)}$ | 3 $^{b)}$ | 4 $^{b)}$ | 5 $^{b)}$ |
|---|---|---|---|---|---|
| zn-PP-homopolymer | 99.879 | 99.825 | 99.8685 | 99.8685 | 99.8685 |
| CaSt | 0.050 | 0.050 | 0.050 | 0.050 | 0.050 |
| AO-1 | 0.050 | 0.050 | 0.050 | 0.050 | 0.050 |
| Phos-1 | 0.021 | 0.075 | 0.021 | 0.021 | 0.021 |

TABLE A-1-1-continued

| composition No. | 1 $^{a)}$ | 2 $^{a)}$ | 3 $^{b)}$ | 4 $^{b)}$ | 5 $^{b)}$ |
|---|---|---|---|---|---|
| compound (106) | — | — | 0.0105 | — | — |
| compound (105) | — | — | — | 0.0105 | — |
| compound (102) | — | — | — | — | 0.0105 |
| total additives content | 0.121 | 0.175 | 0.1315 | 0.1315 | 0.1315 |
| 280° C. melt processing | | | | | |
| melt flow rates | | | | | |
| zero pass | 9.6 | 9.3 | 9.1 | 9.0 | 9.0 |
| 1$^{st}$ pass | 16.6 | 13.2 | 14.3 | 12.3 | 10.9 |
| 3$^{rd}$ pass | 33.3 | 22.7 | 29.6 | 19.2 | 14.8 |
| 5$^{th}$ pass | 58.0 | 42.6 | 49.0 | 30.1 | 19.8 |

Footnotes:
$^{a)}$ reference;
$^{b)}$ inventive

The addition of 0.0105 parts of an inventive compound at formulation No. 3 to 5 improves the melt stability versus formulation No. 1. It allows also a disproportionate reduction of phosphite stabilizer content.

Examples A-2-1 to A-2-9

Polymer Processing Experimental

The various additives are blended with the stated applied granular polymer, which is essentially free of any stabilization additives, in a composition according to the respective tables A-2-1 to A-2-9. The blending is carried out using a Henschel, a Turbula or a Kitchen-Aid mixer.

The thoroughly blended formulations are melt compounded in a twin screw extruder at a lower temperature of 210° C. (410° F.) under nitrogen, which is denoted in the tables as the zero pass extrusion. This ensures good melt mixing with minimal damage to the polymer due to oxidative degradation.

The resultant zero pass extrudate is then extruded multiple times a single screw extruder, fitted with a Maddock mixing section, at a higher temperature of 260° C. (500° F.) or 280° C. (535° F.), open to air. Extrusion at higher temperatures in combination with the presence of oxygen (air) enhances the rate of polymer degradation. Pelletized samples of zero, first, third and fifth pass extrudate are collected and stored in sealed plastic bags at room temperature in storage boxes in the dark.

Melt Flow Rates: The samples are tested for retention of molecular mass (weight). This is measured by melt flow rate retention according to ASTM-1238 on a Tinius-Olsen Extrusion Plastometer. For polypropylene type polymer samples, the test conditions are 230° C. and 2.16 kg. For polyethylene type polymer samples, the test conditions are 190° C. and 2.16 kg or 21.6 kg. The melt flow ratio is calculated as the melt flow rate at 21.6 kg divided by the melt flow rate at 2.16 kg. Melt flow rates are measured in grams of polymer that flow out of a defined orifice in 10 minutes and are stated as grams/10 minutes (decigrams per minute).

Yellowness Index: The yellowness index of some samples is tested for color development observed during the multiple extrusion and is measured according to ASTM-1925 on compression molded plaques of 3.2 mm (125 mil). Color is measured on a DCI SF600 spectrophotometer with large area view, spectral component included, C illuminant and 2 degree observer. Color in these measurements is expressed as Yellowness Index.

Oven Aging: Some samples are tested for oxidative stability below the melting point of the polymer using oven aging to accelerate polymer degradation. This is done by putting compression molded plaques of 1 mm (40 mils) in a Blue M forced draft oven equipped with a rotating carousel in order to homogenize the exposure to an elevated temperature of 135° C. inside the oven. Failure is measured by days to embrittlement by bending the plaque every 3 to 4 days until the plaque snapped due to oxidative degradation. The time is stated in days.

Oxidative Induction Time: Some samples are tested for oxidative stability above the melting point of the polymer using oxidative induction time (OIT) as a means of measuring the activity of the stabilizer in the polymer melt at a high temperature of 190° C. in an oxidative environment (oxygen). The experiments are run on a differential scanning calorimeter (DSC). Scans are collected using a heating rate of 10° C./min under nitrogen from 50° C. to 190° C., then switching to oxygen and holding at isothermal conditions until catastrophic oxidation. Time to onset of catastrophic oxidation (observed as a strong exotherm) is stated in minutes.

Example A-2-1: Stabilization of a Molding Grade Ziegler-Natta Polypropylene Homopolymer A molding grade Ziegler-Natta polypropylene homopolymer (zn-PP-homopolymer) with a melt flow rate of 4 dg/min from a bulk/slurry phase polymerization process is evaluated.

TABLE A-2-1

| composition No. | 1 [a] | 2 [a] | 3 [a] | 4 [b] | 5 [b] |
|---|---|---|---|---|---|
| zn-PP-homopolymer | 99.890 | 99.840 | 99.790 | 99.8575 | 99.8575 |
| CaSt | 0.060 | 0.060 | 0.060 | 0.060 | 0.060 |
| AO-1 | 0.050 | 0.050 | 0.050 | 0.050 | 0.050 |
| Phos-1 | — | 0.050 | 0.100 | 0.022 | 0.022 |
| compound (103) | — | — | — | 0.0105 | — |
| compound (104) | — | — | — | — | 0.0105 |
| total additives content | 0.110 | 0.160 | 0.210 | 0.1425 | 0.1425 |
| 260° C. (500° F.) melt processing | | | | | |
| melt flow rates | | | | | |
| zero pass | 6.03 | 4.59 | 3.90 | 4.38 | 4.30 |
| 1$^{st}$ pass | 9.78 | 6.05 | 4.38 | 5.07 | 4.99 |
| 3$^{rd}$ pass | 13.85 | 7.20 | 5.41 | 6.26 | 5.89 |
| 5$^{th}$ pass | 17.27 | 9.91 | 6.32 | 6.90 | 7.11 |
| oven ageing at 135° C. | | | | | |
| zero pass | 52 | 58 | 62 | 58 | 62 |
| 280° C. (535° F.) melt processing | | | | | |
| melt flow rates | | | | | |
| zero pass | 6.03 | 4.59 | 3.90 | 4.38 | 4.30 |
| 1$^{st}$ pass | 12.03 | 7.04 | 5.19 | 5.77 | 5.59 |
| 3$^{rd}$ pass | 21.84 | 10.49 | 6.81 | 6.78 | 6.91 |
| 5$^{th}$ pass | 34.35 | 17.07 | 9.13 | 8.58 | 9.09 |

Footnotes:
[a] reference;
[b] inventive

The compositions comprised of a low concentration of an inventive compound (105 ppm), a phenolic antioxidant (500 ppm) and a traditional phosphite melt processing stabilizer (220 ppm) provide good performance as measured by retention of melt flow rates in comparison to a common binary blend of the phenolic antioxidant (500 ppm) and the traditional phosphite melt processing stabilizer (500 or 1000 ppm). The ternary blends comprising an inventive compound provide as good or better performance at lower concentrations (825 ppm) in comparison to the common binary blends at higher concentrations (1000 or 1500 ppm). There are no deleterious effects to the long term thermal stability provided by the phenolic antioxidant observed when measured by oven aging at 135° C.

Example A-2-2: Stabilization of a Molding Grade Ziegler-Natta Polypropylene Copolymer A molding grade Ziegler-Natta polypropylene copolymer (zn-PP-copolymer; ethylene as comonomer in around 2% by weight) with a melt flow rate of 3 dg/min from a bulk/slurry phase polymerization process is evaluated.

TABLE A-2-2

| composition No. | 1 [a] | 2 [a] | 3 [a] | 4 [b] | 5 [b] |
|---|---|---|---|---|---|
| zn-PP-copolymer | 99.890 | 99.840 | 99.790 | 99.8575 | 99.8575 |
| CaSt | 0.060 | 0.060 | 0.060 | 0.060 | 0.060 |
| AO-1 | 0.050 | 0.050 | 0.050 | 0.050 | 0.050 |
| Phos-1 | — | 0.050 | 0.100 | 0.022 | 0.022 |
| compound (103) | — | — | — | 0.0105 | — |
| compound (104) | — | — | — | — | 0.0105 |
| total additives content | 0.110 | 0.160 | 0.210 | 0.1425 | 0.1425 |
| 260° C. (500° F.) melt processing | | | | | |
| melt flow rates | | | | | |
| zero pass | 4.60 | 3.34 | 2.79 | 3.55 | 3.30 |
| 1$^{st}$ pass | 7.98 | 4.64 | 3.34 | 4.57 | 3.80 |
| 3$^{rd}$ pass | 11.47 | 5.72 | 3.99 | 6.06 | 4.82 |
| 5$^{th}$ pass | 16.03 | 7.49 | 4.89 | 6.98 | 5.10 |
| Yellowness index | | | | | |
| zero pass | 8.00 | 8.20 | 7.60 | 8.60 | 9.20 |
| 1$^{st}$ pass | 9.30 | 9.50 | 9.00 | 9.10 | 10.50 |
| 3$^{rd}$ pass | 10.80 | 11.40 | 11.10 | 10.10 | 11.90 |
| 5$^{th}$ pass | 12.40 | 13.30 | 13.00 | 11.20 | 12.10 |
| 280° C. (535° F.) melt processing | | | | | |
| melt flow rates | | | | | |
| zero pass | 4.60 | 3.34 | 2.79 | 3.55 | 3.30 |
| 1$^{st}$ pass | 10.50 | 5.11 | 3.68 | 4.79 | 4.64 |
| 3$^{rd}$ pass | 20.24 | 9.81 | 5.89 | 7.23 | 6.05 |
| 5$^{th}$ pass | 32.38 | 15.02 | 8.45 | 10.13 | 9.18 |

Footnotes:
[a] reference;
[b] inventive

The compositions comprised of a low concentration of an inventive compound (105 ppm), a phenolic antioxidant (500 ppm) and a traditional phosphite melt processing stabilizer (220 ppm) provide good performance as measured by retention of melt flow rates in comparison to a common binary blend of the phenolic antioxidant (500 ppm) and the traditional phosphite melt processing stabilizer (500 or 1000 ppm). The ternary blends comprising an inventive compound provide nearly as good or better performance at lower concentrations (825 ppm) in comparison to the common binary blends at higher concentrations (1000 or 1500 ppm).

Example A-2-3: Stabilization of a Film Grade Ziegler-Natta Linear Low Density Polyethylene Copolymer A film grade Ziegler-Natta polyethylene copolymer (zn-LLDPE-copolymer; butene as comonomer, density 0.92 g/cm$^3$) with a melt flow rate of 2 dg/min at 190° C. and 2.16 kg from a gas phase polymerization process is evaluated.

TABLE A-2-3

| composition No. | 1 [a] | 2 [a] | 3 [a] | 4 [b] | 5 [b] |
|---|---|---|---|---|---|
| zn-LLDPE-copolymer | 99.935 | 99.915 | 99.845 | 99.925 | 99.925 |
| ZnO | 0.015 | 0.015 | 0.015 | 0.015 | 0.015 |
| AO-2 | 0.020 | 0.020 | 0.020 | 0.020 | 0.020 |
| Phos-1 | 0.030 | 0.050 | 0.130 | 0.030 | 0.030 |
| compound (103) | — | — | — | 0.010 | — |
| compound (104) | — | — | — | — | 0.010 |
| total additives content | 0.065 | 0.085 | 0.155 | 0.075 | 0.075 |
| 260° C. (500° F.) melt processing | | | | | |
| melt flow rates (190° C./2.16 kg) | | | | | |
| zero pass | 2.17 | 2.12 | 2.15 | 2.11 | 2.12 |
| $1^{st}$ pass | 1.81 | 1.90 | 2.01 | 1.96 | 1.97 |
| $3^{rd}$ pass | 1.46 | 1.60 | 1.89 | 1.75 | 1.76 |
| $5^{th}$ pass | 1.24 | 1.36 | 1.64 | 1.56 | 1.57 |
| melt flow rates (190° C./21.6 kg) | | | | | |
| zero pass | 54.12 | 53.48 | 54.51 | 53.58 | 53.00 |
| $1^{st}$ pass | 51.85 | 52.43 | 51.55 | 52.48 | 52.39 |
| $3^{rd}$ pass | 49.34 | 50.27 | 50.63 | 50.84 | 51.37 |
| $5^{th}$ pass | 47.53 | 47.99 | 46.47 | 49.43 | 49.54 |
| melt flow ratio (190° C.; 21.6 kg/2.16 kg) | | | | | |
| zero pass | 24.93 | 25.27 | 25.37 | 25.41 | 25.00 |
| $1^{st}$ pass | 28.62 | 27.65 | 25.68 | 26.79 | 26.61 |
| $3^{rd}$ pass | 33.75 | 31.48 | 26.86 | 29.12 | 29.20 |
| $5^{th}$ pass | 38.23 | 35.31 | 28.30 | 31.76 | 31.64 |
| yellowness index | | | | | |
| zero pass | −0.80 | −0.80 | −1.20 | 6.60 | 6.00 |
| $1^{st}$ pass | 1.10 | 1.40 | 1.00 | 7.60 | 8.30 |
| $3^{rd}$ pass | 3.00 | 3.90 | 2.00 | 10.30 | 11.40 |
| $5^{th}$ pass | 4.70 | 6.00 | 5.00 | 11.70 | 13.00 |
| oxidative induction time (10 mil films/onset at 190° C.) | | | | | |
| zero pass | 26 | 39 | 74 | 43 | 48 |

Footnotes:
[a] reference;
[b] inventive

The composition comprised of a low concentration of an inventive compound (100 ppm), in combination with a phenolic antioxidant (200 ppm) and common phosphite melt processing stabilizer (300 ppm), provides good performance as measured by retention of melt flow rates in comparison to a traditional binary blend of the phenolic antioxidant (200 ppm) and the common phosphite melt processing stabilizer (500 or 1300 ppm). The ternary blends provide as good or better performance at lower concentrations (600 ppm) in comparison to the common binary blends at higher concentrations (700-1300 ppm). No deleterious effects to the oxidative stability provided by the phenolic antioxidant are observed as measured by oxidative induction time.

Example A-2-4: Stabilization of a Molding Grade Cr Based High Density Polyethylene A molding grade chromium catalyzed polyethylene (Cr-HDPE; density 0.955 g/cm³) with a melt flow rate of 0.3 dg/min at 190° C. and 2.16 kg from a gas phase polymerization process is evaluated.

TABLE A-2-4

| composition No. | 1 [a] | 2 [a] | 3 [a] | 4 [b] | 5 [b] |
|---|---|---|---|---|---|
| Cr-HDPE | 99.935 | 99.915 | 99.845 | 99.925 | 99.925 |
| AO-1 | 0.050 | 0.050 | 0.050 | 0.050 | 0.050 |
| Phos-1 | — | 0.050 | 0.100 | 0.022 | 0.022 |
| compound (103) | — | — | — | 0.011 | — |
| compound (104) | — | — | — | — | 0.011 |
| total additives content | 0.050 | 0.100 | 0.150 | 0.083 | 0.083 |

TABLE A-2-4-continued

| composition No. | 1[a] | 2[a] | 3[a] | 4[b] | 5[b] |
|---|---|---|---|---|---|
| 260° C. (500° F.) melt processing | | | | | |
| melt flow rates (190° C./2.16 kg) | | | | | |
| zero pass | 0.22 | 0.28 | 0.29 | 0.32 | 0.31 |
| 1st pass | 0.20 | 0.26 | 0.29 | 0.29 | 0.31 |
| 3rd pass | 0.18 | 0.25 | 0.25 | 0.25 | 0.29 |
| 5th pass | 0.13 | 0.17 | 0.21 | 0.22 | 0.28 |
| melt flow rates (190° C./21.6 kg) | | | | | |
| zero pass | 26.73 | 28.27 | 28.43 | 29.81 | 29.84 |
| 1st pass | 28.37 | 29.35 | 29.89 | 30.42 | 31.49 |
| 3rd pass | 28.74 | 28.39 | 29.59 | 30.36 | 32.15 |
| 5th pass | 26.77 | 27.82 | 29.06 | 30.67 | 32.85 |
| melt flow ratio (190° C.; 21.6 kg/2.16 kg) | | | | | |
| zero pass | 121.72 | 100.03 | 99.37 | 93.96 | 95.55 |
| 1st pass | 140.00 | 112.18 | 104.62 | 106.28 | 102.37 |
| 3rd pass | 162.47 | 134.80 | 120.51 | 121.67 | 109.35 |
| 5th pass | 200.50 | 165.00 | 138.98 | 140.14 | 119.25 |
| yellowness index | | | | | |
| zero pass | 7.70 | 4.10 | 3.50 | 4.50 | 9.50 |
| 1st pass | 8.70 | 5.80 | 5.50 | 5.60 | 10.50 |
| 3rd pass | 10.30 | 7.10 | 7.00 | 7.30 | 12.10 |
| 5th pass | 10.90 | 8.30 | 8.00 | 8.20 | 12.00 |
| oxidative induction time (10 mil films/onset at 190° C.) | | | | | |
| zero pass | 68 | 106 | 151 | 109 | 110 |

Footnotes:
[a] reference;
[b] inventive

The composition comprised of a low concentration of an inventive compound (110 ppm) in combination with a phenolic antioxidant (500 ppm) and a common phosphite melt processing stabilizer (220 ppm) provide good performance as measured by retention of melt flow rates in comparison to a common binary blend of the phenolic antioxidant (500 ppm) and the common phosphite melt processing stabilizer (500 or 1000 ppm). The ternary blends provide nearly as good or better performance at lower concentrations (830 ppm) in comparison to the common binary blends at higher concentrations (1000-1500 ppm). No deleterious effects to the oxidative stability provided by the phenolic antioxidant are observed as measured by oxidative induction time.

Example A-2-5: Stabilization of a Blown Film Grade Metallocene Based Catalyst Linear Low Density Polyethylene Copolymer A blown film grade metallocene based catalyst linear low density polyethylene copolymer (metallocene based catalyst LLDPE-copolymer; hexene as co-monomer) with a density of 0.918 g/cm$^3$ and a melt flow rate of 1.0 dg/min at 190° C./2.16 kg from a gas phase polymerization process is evaluated.

TABLE A-2-5

| | composition No. | | | | | |
|---|---|---|---|---|---|---|
| | 1[a] | 2[a] | 3[a] | 4[b] | 5[b] | 6[b] |
| metallocene based catalyst LLDPE-copolymer | 99.900 | 99.850 | 99.800 | 99.844 | 99.844 | 99.844 |
| ZnSt | 0.050 | 0.050 | 0.050 | 0.050 | 0.050 | 0.050 |
| AO-2 | 0.050 | 0.050 | 0.050 | 0.050 | 0.050 | 0.050 |
| Phos-1 | — | 0.050 | 0.100 | 0.045 | 0.045 | 0.045 |
| compound (105) | — | — | — | 0.011 | — | — |
| compound (107) | — | — | — | — | 0.011 | — |
| compound (108) | — | — | — | — | — | 0.011 |
| total additives content | 0.100 | 0.150 | 0.200 | 0.156 | 0.156 | 0.156 |
| 260° C. (500° F.) melt processing melt flow rates (190° C./2.16 kg) | | | | | | |
| zero pass | 0.66 | 0.82 | 0.91 | 0.90 | 0.90 | 0.90 |
| 1st pass | 0.52 | 0.67 | 0.84 | 0.83 | 0.82 | 0.80 |
| 3rd pass | 0.37 | 0.48 | 0.69 | 0.68 | 0.70 | 0.65 |
| 5th pass | 0.29 | 0.37 | 0.53 | 0.57 | 0.59 | 0.54 |
| melt flow rates (190° C./21.6 kg) | | | | | | |
| zero pass | 12.46 | 13.71 | 14.27 | 14.46 | 14.40 | 14.43 |
| 1st pass | 11.70 | 12.76 | 13.94 | 13.97 | 13.92 | 13.85 |
| 3rd pass | 10.79 | 11.61 | 13.06 | 13.13 | 13.28 | 13.03 |
| 5th pass | 10.12 | 10.87 | 12.10 | 12.67 | 12.75 | 12.49 |
| melt flow ratio (190° C.; 21.6 kg/2.16 kg) | | | | | | |
| zero pass | 18.88 | 16.77 | 15.72 | 15.98 | 16.02 | 16.08 |
| 1st pass | 22.44 | 19.02 | 16.59 | 16.86 | 16.94 | 17.35 |

TABLE A-2-5-continued

| | composition No. | | | | | |
|---|---|---|---|---|---|---|
| | 1[a] | 2[a] | 3[a] | 4[b] | 5[b] | 6[b] |
| $3^{rd}$ pass | 29.02 | 24.28 | 18.81 | 19.28 | 19.06 | 20.16 |
| $5^{th}$ pass | 34.47 | 29.06 | 22.90 | 22.37 | 21.61 | 23.04 |
| oxidative induction time (10 mil films/onset at 190° C.) | | | | | | |
| zero pass | 25 | 35 | 89 | 64 | 54 | 66 |

Footnotes:
[a] reference;
[b] inventive

The compositions comprised of a low concentration of an inventive compound (110 ppm), a phenolic antioxidant (500 ppm) and a traditional phosphite melt processing stabilizer (450 ppm) provide good performance as measured by retention of melt flow rates in comparison to a common binary blend of the phenolic antioxidant (500 ppm) and the traditional phosphite melt processing stabilizer (500 or 1000 ppm). The ternary blends comprising an inventive compound provide as good or better performance at comparable or lower concentrations (1060 ppm) in comparison to the common binary blends (1000 or 1500 ppm). There are no deleterious effects to the oxidative stability provided by the phenolic antioxidant as measured by oxidative induction time.

Example A-2-6: Stabilization of a Molding Grade Ziegler-Natta Polypropylene Copolymer A molding grade Ziegler-Natta polypropylene copolymer (zn-PP-copolymer-2.5; ethylene as co-monomer in around 2% by weight) with a melt flow rate of 2.5 dg/min from a bulk/slurry phase polymerization process is evaluated.

TABLE A-2-6

| | composition No. | | | | | |
|---|---|---|---|---|---|---|
| | 1[a] | 2[a] | 3[a] | 4[b] | 5[b] | 6[b] |
| zn-PP-copolymer-2.5 | 99.890 | 99.840 | 99.790 | 99.834 | 99.834 | 99.834 |
| CaSt | 0.060 | 0.060 | 0.060 | 0.060 | 0.060 | 0.060 |
| AO-1 | 0.050 | 0.050 | 0.050 | 0.050 | 0.050 | 0.050 |
| Phos-1 | — | 0.050 | 0.100 | 0.045 | 0.045 | 0.045 |
| compound (105) | — | — | — | 0.011 | — | — |
| compound (107) | — | — | — | — | 0.011 | — |
| compound (108) | — | — | — | — | — | 0.011 |
| total additives content | 0.110 | 0.160 | 0.210 | 0.166 | 0.166 | 0.166 |
| 260° C. (500° F.) melt processing melt flow rates (230° C./2.16 kg) | | | | | | |
| zero pass | 3.87 | 2.92 | 2.65 | 2.73 | 2.57 | 2.58 |
| $1^{st}$ pass | 6.36 | 4.19 | 2.99 | 3.13 | 3.04 | 2.97 |
| $3^{rd}$ pass | 8.47 | 5.41 | 3.37 | 3.31 | 3.48 | 3.52 |
| $5^{th}$ pass | 11.65 | 5.70 | 3.85 | 3.71 | 4.10 | 4.02 |
| yellowness index | | | | | | |
| zero pass | 8.50 | 7.90 | 6.60 | 6.30 | 6.60 | 7.40 |
| $1^{st}$ pass | 9.80 | 8.90 | 8.10 | 7.20 | 7.20 | 7.80 |
| $3^{rd}$ pass | 11.20 | 10.70 | 9.90 | 8.90 | 9.10 | 9.20 |
| $5^{th}$ pass | 12.50 | 11.80 | 11.30 | 9.70 | 10.10 | 9.70 |

TABLE A-2-6-continued

| | composition No. | | | | | |
|---|---|---|---|---|---|---|
| | 1[a] | 2[a] | 3[a] | 4[b] | 5[b] | 6[b] |
| oven ageing at 135° C. | | | | | | |
| zero pass | 60 | 69 | 72 | 77 | 72 | 77 |
| oven ageing at 150° C. | | | | | | |
| zero pass | 5 | 9 | 9 | 9 | 9 | 9 |
| oxidative induction time (10 mil films/onset at 190° C.) | | | | | | |
| zero pass | 20 | 25 | 34 | 81 | 32 | 31 |

Footnotes:
[a] reference;
[b] inventive

The compositions comprised of a low concentration of an inventive compound (110 ppm), a phenolic antioxidant (500 ppm) and a traditional phosphite melt processing stabilizer (450 ppm) provide good performance as measured by retention of melt flow rates in comparison to a common binary blend of the phenolic antioxidant (500 ppm) and the traditional phosphite melt processing stabilizer (500 or 1000 ppm). The ternary blends comprising an inventive compound provide as good or better performance at comparable or lower concentrations (1060 ppm) in comparison to the common binary blends (1000 or 1500 ppm). There are no deleterious effects to the long thermal stability provided by the phenolic antioxidant as measured by oven ageing.

Example A-2-7: Stabilization of a Molding Grade Ziegler-Natta Polypropylene Homopolymer A molding grade Ziegler-Natta polypropylene homopolymer (zn-PP-homopolymer) with a melt flow rate of 4 dg/min at 230° C./2.16 kg from a bulk/slurry phase polymerization process is evaluated.

TABLE A-2-7

| | composition No. | | | | | |
|---|---|---|---|---|---|---|
| | 1[a] | 2[a] | 3[a] | 4[b] | 5[b] | 6[b] |
| zn-PP-homopolymer | 99.890 | 99.840 | 99.790 | 99.840 | 99.840 | 99.840 |
| CaSt | 0.060 | 0.060 | 0.060 | 0.060 | 0.060 | 0.060 |
| AO-1 | 0.050 | 0.050 | 0.050 | 0.050 | 0.050 | 0.050 |
| Phos-1 | — | 0.050 | 0.100 | 0.0375 | 0.0375 | 0.0375 |
| compound (105) | — | — | — | 0.0125 | — | — |
| compound (107) | — | — | — | — | 0.0125 | — |
| compound (108) | — | — | — | — | — | 0.0125 |
| total additives content | 0.110 | 0.160 | 0.210 | 0.160 | 0.160 | 0.160 |
| 260° C. (500° F.) melt processing melt flow rates (230° C./2.16 kg) | | | | | | |
| zero pass | 18.15 | 13.79 | 12.77 | 13.90 | 13.49 | 13.74 |
| $1^{st}$ pass | 23.40 | 15.18 | 14.30 | 15.36 | 15.79 | 15.30 |
| $3^{rd}$ pass | 31.90 | 18.27 | 15.62 | 16.00 | 16.94 | 17.71 |
| $5^{th}$ pass | 42.49 | 21.74 | 17.88 | 17.28 | 18.81 | 19.77 |
| yellowness index | | | | | | |
| zero pass | 4.40 | 4.20 | 3.70 | 4.90 | 4.20 | 5.10 |
| $1^{st}$ pass | 5.10 | 5.40 | 4.90 | 6.30 | 5.00 | 5.60 |

TABLE A-2-7-continued

| | composition No. | | | | | |
|---|---|---|---|---|---|---|
| | 1[a] | 2[a] | 3[a] | 4[b] | 5[b] | 6[b] |
| 3$^{rd}$ pass | 5.70 | 6.10 | 5.90 | 7.50 | 5.50 | 6.00 |
| 5$^{th}$ pass | 6.30 | 7.90 | 7.30 | 8.60 | 6.40 | 7.20 |

Footnotes:
[a] reference;
[b] inventive

The compositions comprised of a low concentration of an inventive compound (125 ppm), a phenolic antioxidant (500 ppm) and a traditional phosphite melt processing stabilizer (375 ppm) provide good performance as measured by retention of melt flow rates in comparison to a common binary blend of the phenolic antioxidant (500 ppm) and the traditional phosphite melt processing stabilizer (500 or 1000 ppm). The ternary blends comprising an inventive compound provide as good or better performance at comparable or lower concentrations (1000 ppm) in comparison to the common binary blends (1000 or 1500 ppm).

Example A-2-8: Stabilization of a Film Grade Ziegler-Natta Linear Low Density Polyethylene Copolymer A cast film grade Ziegler-Natta linear low density polyethylene copolymer (zn-LLDPE-copolymer; butene as comonomer, density 0.92 g/cm$^3$) with a melt flow rate of 2 dg/min at 190° C./2.16 kg from a gas phase polymerization process is evaluated.

TABLE A-2-8

| | composition No. | | | | | | |
|---|---|---|---|---|---|---|---|
| | 1[a] | 2[a] | 3[a] | 4[b] | 5[b] | 6[b] | 7[b] |
| zn-LLDPE-copolymer | 99.925 | 99.885 | 99.845 | 99.915 | 99.915 | 99.915 | 99.915 |
| ZnO | 0.015 | 0.015 | 0.015 | 0.015 | 0.015 | 0.015 | 0.015 |
| AO-2 | 0.020 | 0.020 | 0.020 | 0.020 | 0.020 | 0.020 | 0.020 |
| Phos-1 | 0.040 | 0.080 | 0.120 | 0.040 | 0.040 | 0.040 | 0.040 |
| compound (105) | — | — | — | 0.010 | — | — | — |
| compound (107) | — | — | — | — | 0.010 | — | — |
| compound (108) | — | — | — | — | — | 0.010 | — |
| compound (109) | — | — | — | — | — | — | 0.010 |
| total additives content | 0.075 | 0.115 | 0.155 | 0.085 | 0.085 | 0.085 | 0.085 |
| 260° C. (500° F.) melt processing | | | | | | | |
| melt flow rates (190° C./2.16 kg) | | | | | | | |
| zero pass | 2.05 | 2.22 | 2.22 | 2.22 | 2.17 | 2.03 | 2.10 |
| 1$^{st}$ pass | 1.77 | 2.01 | 2.16 | 2.00 | 1.98 | 1.97 | 2.02 |
| 3$^{rd}$ pass | 1.39 | 1.54 | 2.00 | 1.81 | 1.72 | 1.74 | 1.75 |
| 5$^{th}$ pass | 0.99 | 1.32 | 1.73 | 1.60 | 1.51 | 1.56 | 1.48 |
| melt flow rates (190° C./21.6 kg) | | | | | | | |
| zero pass | 51.92 | 53.02 | 52.66 | 52.30 | 52.19 | 52.56 | 52.54 |
| 1$^{st}$ pass | 48.68 | 51.64 | 52.88 | 50.76 | 50.56 | 51.28 | 50.84 |
| 3$^{rd}$ pass | 45.13 | 48.28 | 51.15 | 49.24 | 48.79 | 48.87 | 48.63 |
| 5$^{th}$ pass | 43.10 | 46.75 | 48.93 | 47.49 | 46.61 | 47.54 | 46.18 |
| melt flow ratio (190° C.; 21.6 kg/2.16 kg) | | | | | | | |
| zero pass | 25.36 | 23.88 | 23.68 | 23.53 | 24.06 | 25.94 | 25.05 |
| 1$^{st}$ pass | 27.49 | 25.69 | 24.44 | 25.38 | 25.60 | 26.03 | 25.20 |
| 3$^{rd}$ pass | 32.56 | 31.37 | 25.61 | 27.22 | 28.32 | 28.07 | 27.73 |
| 5$^{th}$ pass | 43.49 | 35.31 | 28.35 | 29.65 | 30.78 | 30.45 | 31.14 |
| yellowness index | | | | | | | |
| zero pass | 3.20 | 0.80 | −0.10 | 2.40 | 0.80 | 0.60 | 1.70 |
| 1$^{st}$ pass | 3.80 | 3.00 | 1.20 | 3.20 | 1.60 | 1.20 | 1.90 |
| 3$^{rd}$ pass | 7.60 | 5.60 | 2.30 | 3.40 | 2.60 | 1.80 | 3.00 |
| 5$^{th}$ pass | 8.30 | 7.10 | 4.00 | 4.80 | 3.90 | 2.70 | 3.40 |
| oxidative induction time (10 mil films/onset at 190° C.) | | | | | | | |
| zero pass | 27 | 41 | 60 | 47 | 42 | 51 | 54 |

Footnotes:
[a] reference;
[b] inventive

The compositions comprised of a low concentration of an inventive compound (100 ppm), a phenolic antioxidant (200 ppm) and a traditional phosphite melt processing stabilizer (400 ppm) provide good performance as measured by retention of melt flow rates in comparison to a common binary blend of the phenolic antioxidant (200 ppm) and the traditional phosphite melt processing stabilizer (800 or 1200 ppm). The ternary blends comprising an inventive compound provide as good or better performance at lower concentrations (700 ppm) in comparison to the common binary blends (800 or 1200 ppm). There are no deleterious effects to the oxidative stability provided by the phenolic antioxidant as measured by oxidative induction time.

Example A-2-9: Stabilization of a Molding Grade Cr Based High Density Polyethylene A molding grade chromium catalyzed polyethylene (Cr-HDPE; density 0.955 g/cm$^3$) with a melt flow rate of 0.3 dg/min at 190° C./2.16 kg from a gas phase polymerization process is evaluated.

The compositions comprised of a low concentration of an inventive compound (110 ppm), a phenolic antioxidant (500 ppm) and a traditional phosphite melt processing stabilizer (330 ppm) provide good performance as measured by retention of melt flow rates in comparison to a common binary blend of the phenolic antioxidant (500 ppm) and the traditional phosphite melt processing stabilizer (500 or 1000 ppm). The ternary blends comprising an inventive compound provide as good or better performance at lower concentrations (940 ppm) in comparison to the common binary blends (1000 or 1500 ppm).

The invention claimed is:

1. A composition, comprising:

a) an organic material susceptible to oxidative, thermal or light-induced degradation, and b) a compound (101), (102), (103), (104), (105), (106), (107), (108) or (109):

TABLE A-2-9

| | composition No. | | | | | | |
|---|---|---|---|---|---|---|---|
| | 1[a] | 2[a] | 3[a] | 4[b] | 5[b] | 6[b] | 7[b] |
| Cr-HDPE | 99.950 | 99.900 | 99.850 | 99.906 | 99.906 | 99.906 | 99.906 |
| AO-1 | 0.050 | 0.050 | 0.050 | 0.050 | 0.050 | 0.050 | 0.050 |
| Phos-1 | — | 0.050 | 0.100 | 0.033 | 0.033 | 0.033 | 0.033 |
| compound (105) | — | — | — | 0.011 | — | — | — |
| compound (107) | — | — | — | — | 0.011 | — | — |
| compound (108) | — | — | — | — | — | 0.011 | — |
| compound (109) | — | — | — | — | — | — | 0.011 |
| total additives content | 0.050 | 0.100 | 0.150 | 0.094 | 0.094 | 0.094 | 0.094 |
| 260° C. (500° F.) melt processing melt flow rates (190° C./2.16 kg) | | | | | | | |
| zero pass | 0.30 | 0.32 | 0.32 | 0.29 | 0.30 | 0.31 | 0.31 |
| 1$^{st}$ pass | 0.25 | 0.30 | 0.32 | 0.29 | 0.29 | 0.29 | 0.30 |
| 3$^{rd}$ pass | 0.18 | 0.26 | 0.30 | 0.26 | 0.27 | 0.28 | 0.27 |
| 5$^{th}$ pass | 0.15 | 0.23 | 0.27 | 0.25 | 0.25 | 0.26 | 0.26 |
| melt flow rates (190° C./21.6 kg) | | | | | | | |
| zero pass | 28.00 | 28.56 | 28.70 | 26.56 | 28.11 | 27.70 | 27.93 |
| 1$^{st}$ pass | 28.13 | 29.35 | 30.07 | 28.50 | 30.00 | 28.16 | 29.65 |
| 3$^{rd}$ pass | 26.50 | 29.40 | 30.24 | 28.71 | 28.73 | 30.04 | 30.00 |
| 5$^{th}$ pass | 25.50 | 29.04 | 29.91 | 29.21 | 29.90 | 30.02 | 29.98 |
| melt flow ratio (190° C.; 21.6 kg/2.16 kg) | | | | | | | |
| zero pass | 93.33 | 89.25 | 89.69 | 91.59 | 93.70 | 89.35 | 90.10 |
| 1$^{st}$ pass | 112.52 | 97.83 | 93.97 | 98.28 | 103.45 | 97.10 | 98.83 |
| 3$^{rd}$ pass | 147.22 | 113.08 | 100.80 | 110.42 | 106.41 | 107.29 | 111.11 |
| 5$^{th}$ pass | 170.00 | 126.26 | 110.78 | 116.84 | 119.60 | 115.46 | 115.31 |

Footnotes:
[a] reference;
[b] inventive (101)
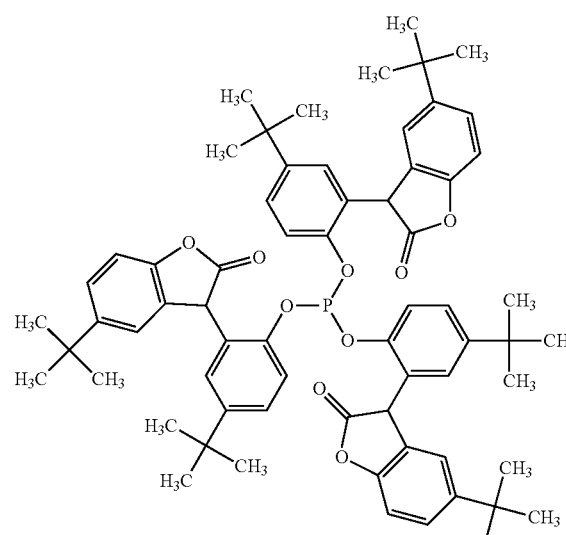
(103)
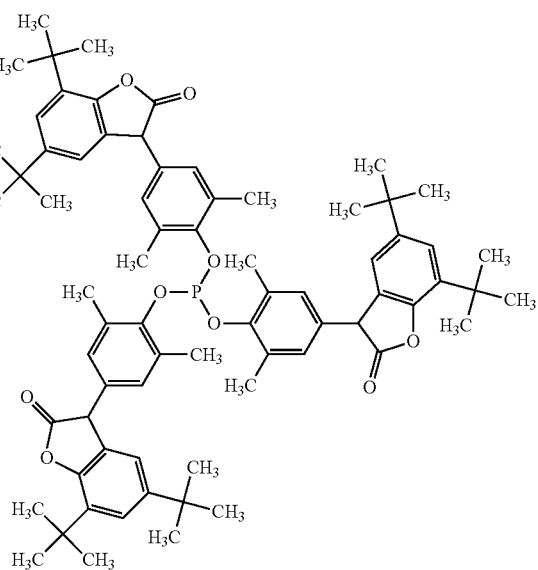
(102)
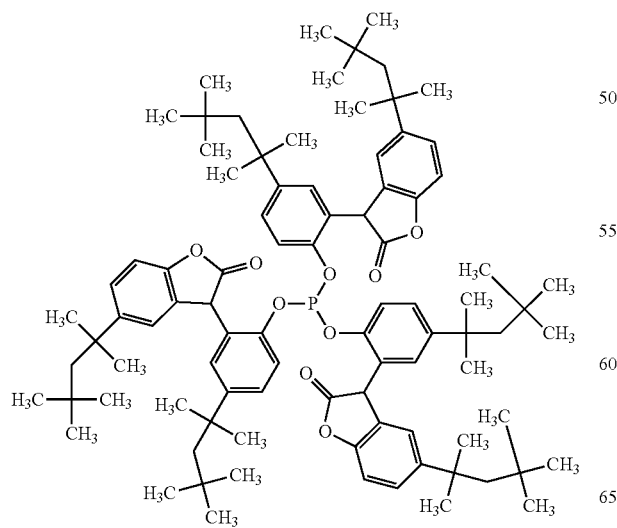
(104)
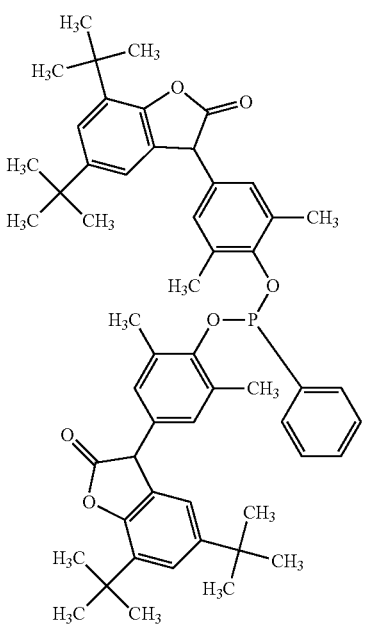

(105)
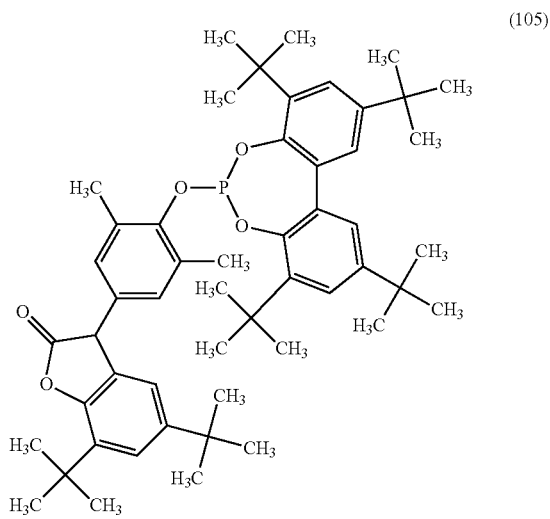

(106)
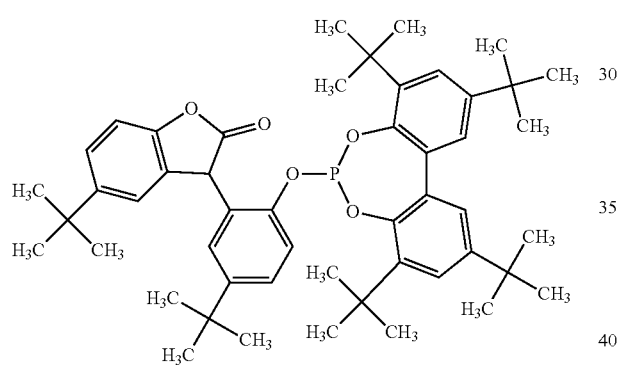

(107)
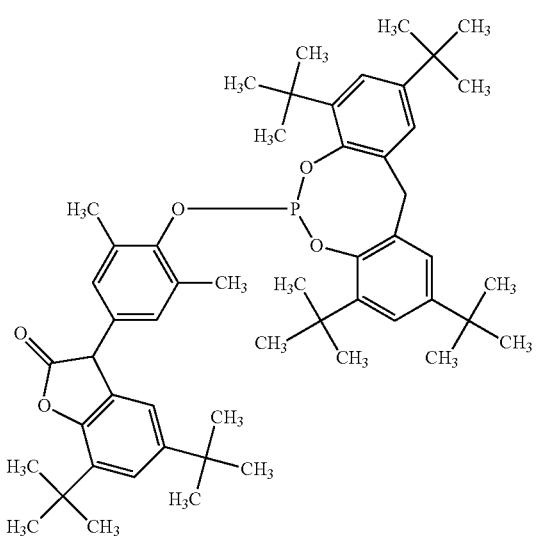

(108)
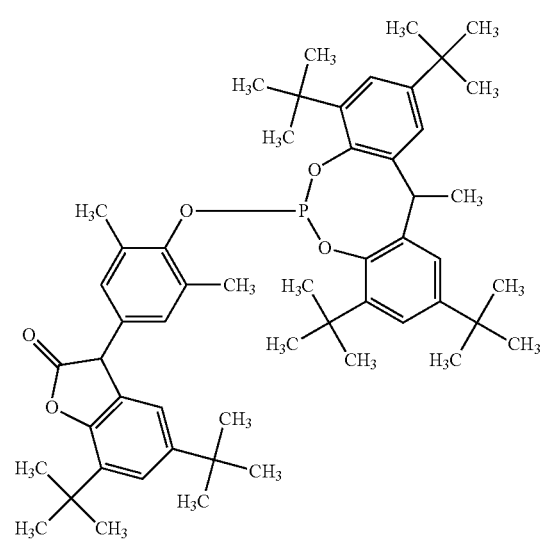

(109)
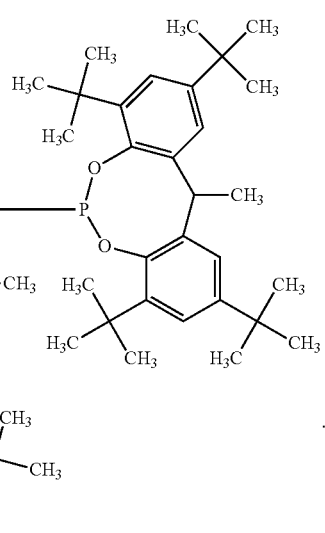

2. The composition according to claim 1, wherein the organic material is a polymer, an oligohydroxy compound, a wax, a fat or a mineral oil.

3. The composition according to claim 2, wherein the organic material is a polymer, which is a polyolefin or a copolymer thereof, a polystyrene or a copolymer thereof, a polyurethane or a copolymer thereof, or a polyether, and which is obtained by a method comprising:
polymerizing an epoxide, an oxetane or tetrahydrofuran, or a copolymer thereof, a polyester or a copolymer thereof, a polycarbonate or a copolymer thereof, a poly(vinyl chloride) or a copolymer thereof, a poly(vinylidene chloride) or a copolymer thereof, a polysulfone or a copolymer thereof, a polybutadiene or a copolymer thereof, a poly(vinyl acetate) or a copolymer thereof, a poly(vinyl alcohol) or a copolymer thereof, a poly(vinyl acetal) or a copolymer thereof, or a polyamide or a copolymer thereof.

4. The composition according to claim 1, wherein component b) is present in the composition in an amount of 0.0005% to 10% based on the weight of component a).

5. The composition according to claim 1, further comprising:
as a component c), a first further additive.

6. The composition according to claim 5, which comprises as component c) a phenolic antioxidant, which is tetrakis-[β-(3,5-di-tert-butyl-4-hydroxyphenyl)-propionyloxymethyl]methane or stearyl β-(3,5-di-tert-butyl-4-hydroxyphenyl)-propionate.

7. The composition according to claim 5, which comprises as component c) a phosphite, which is tris-(2,4-di-tert-butylphenyl) phosphite.

8. The composition according to claim 5, wherein the first further additive comprises at least one selected from the group consisting of a phosphite or phosphorite different to component b), an acid scavenger, a phenolic antioxidant, and an aminic antioxidant.

9. The composition according to claim 8, wherein the further additive comprises a phenolic antioxidant, which is an ester of P-(3,5-di-tert-butyl-4-hydroxyphenyl)propionic acid.

10. The composition according to claim 8, further comprising:
as a component d), a second further additive, which is a phosphite or phosphorite different to component b), an acid scavenger, a phenolic antioxidant or an aminic antioxidant,
with the proviso that component d) is a different substance than component c).

11. The composition according to claim 1, wherein component (h) is compound (101) as defined in claim 1.

12. The composition according to claim 1, wherein component (b) is compound (102) as defined in claim 1.

13. The composition according to claim 1, wherein component (h) is compound (103) as defined in claim 1.

14. The composition according to claim 1, wherein component (b) is compound (104) as defined in claim 1.

15. The composition according to claim 1, wherein component (b) is compound (105) as defined in claim 1.

16. The composition according to claim 1, wherein component (b) is compound (106) as defined in claim 1.

17. The composition according to claim 1, wherein component (b) is compound (107) as defined in claim 1.

18. The composition according to claim 1, wherein component (b) is compound (108) as defined in claim 1.

19. The composition according to claim 1, wherein component (b) is compound (109) as defined in claim 1.

20. A process for protecting an organic material susceptible to oxidative, thermal or light-induced degradation, the process comprising incorporating the organic material into, or applying the organic material onto, a compound (101), (102), (103), (104), (105), (106), (107), (108) or (109):

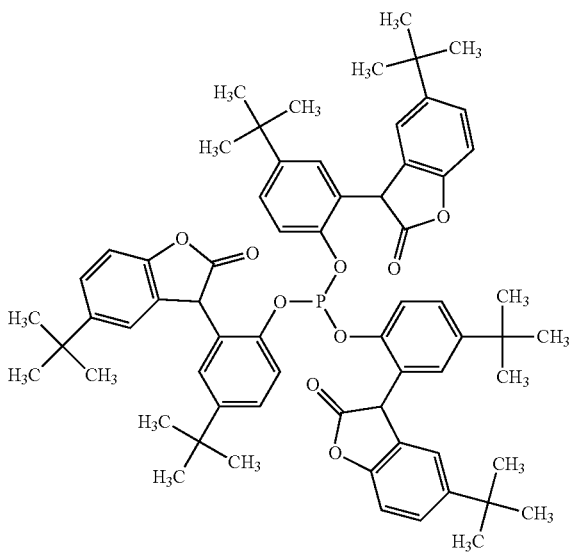

(101)

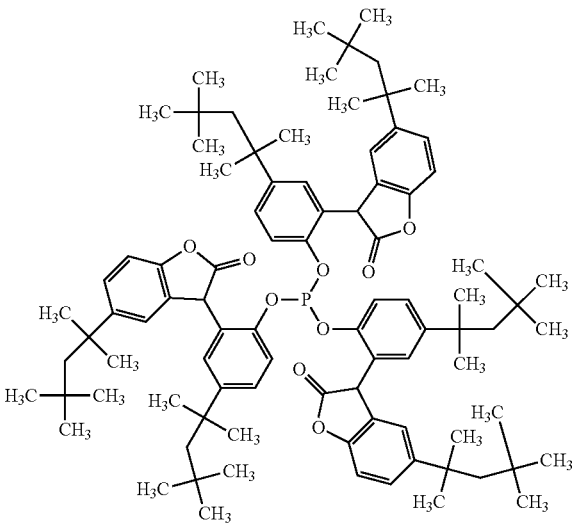

(102)

(103)
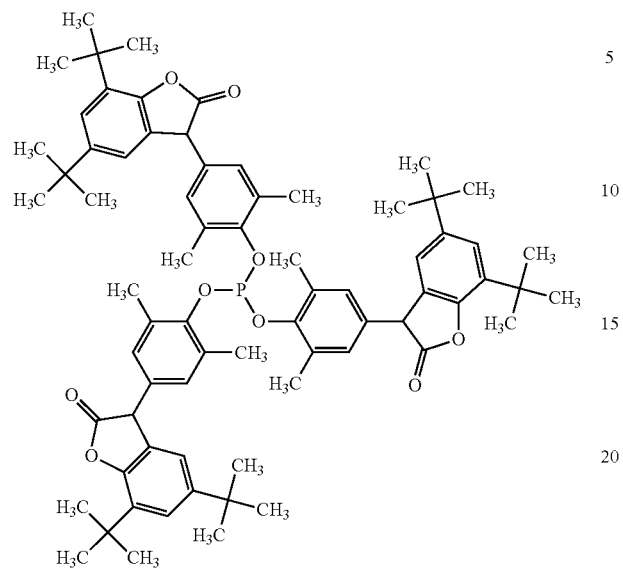
(105)
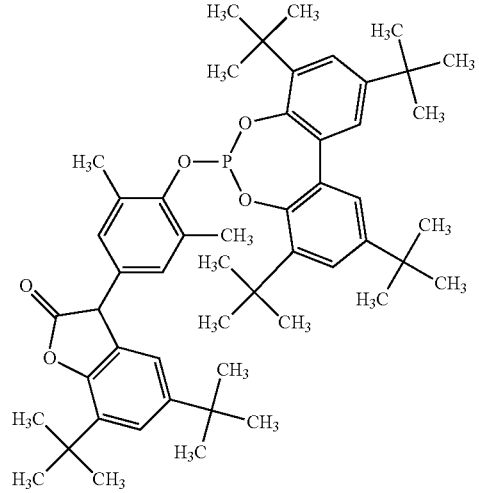
(106)
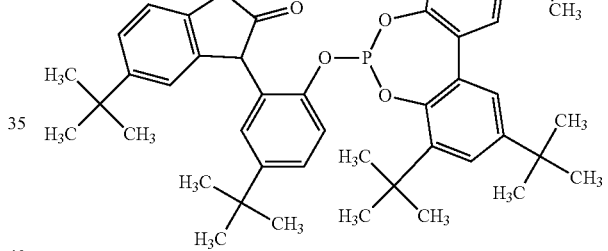
(104)
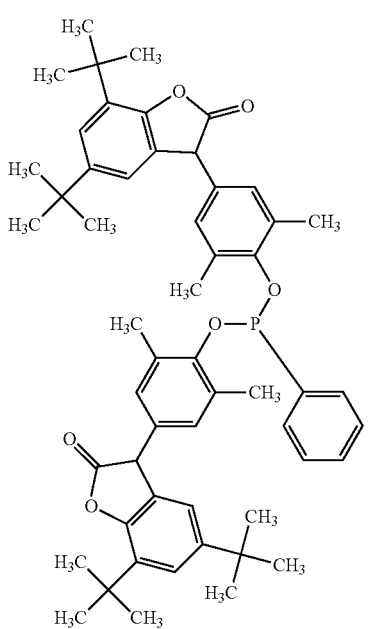
(107)
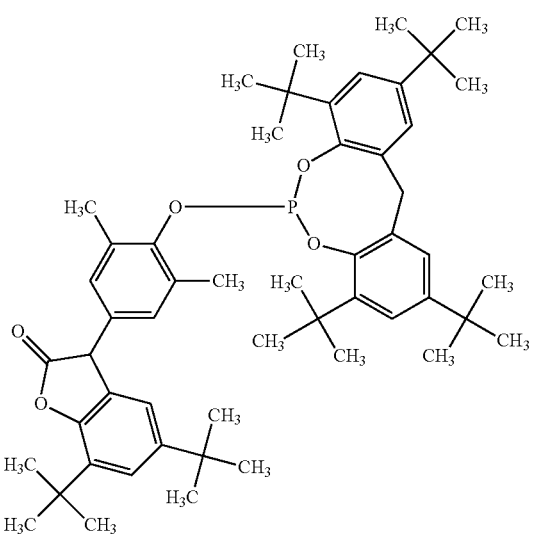

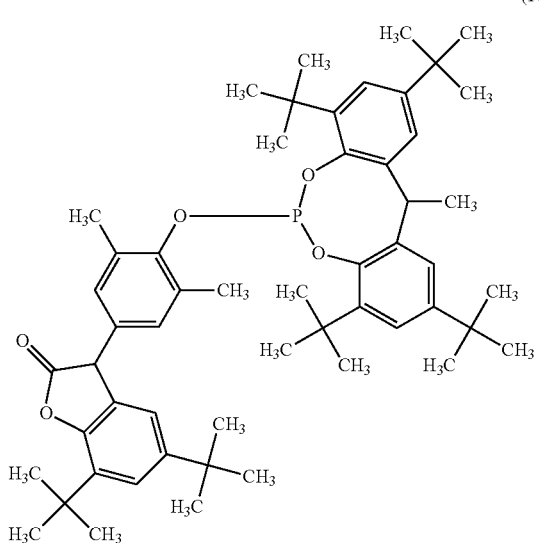
(108)

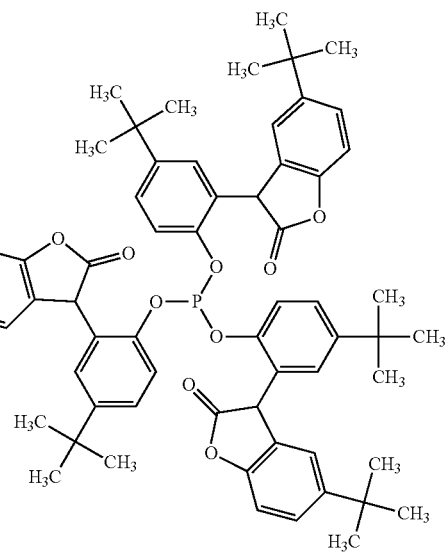
(101)

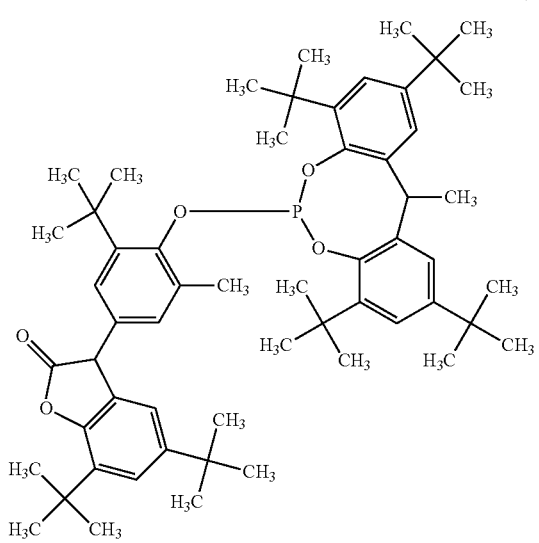
(109)

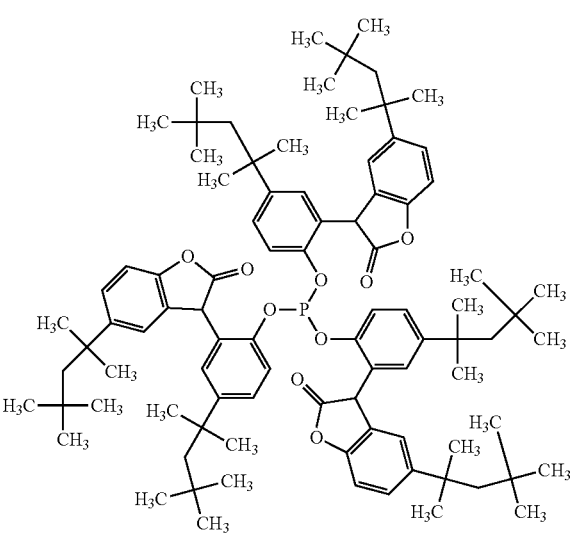
(102)

21. The process according to claim 20, wherein:

the organic material is a polymer;

the incorporating into the polymer is carried out at a temperature between 135° C. to 350° C.; and the polymer is a polyolefin or a copolymer thereof, a polystyrene or a copolymer thereof, a polyurethane or a copolymer thereof, or a polyether, which is obtained by a method comprising polymerizing an epoxide, an oxetane or tetrahydrofuran, or a copolymer thereof, a polyester or a copolymer thereof, a polycarbonate or a copolymer thereof, a poly(vinyl chloride) or a copolymer thereof, a poly(vinylidene chloride) or a copolymer thereof, a polysulfone or a copolymer thereof, a polybutadiene or a copolymer thereof, a poly(vinyl acetate) or a copolymer thereof, a poly(vinyl alcohol) or a copolymer thereof, a poly(vinyl acetal) or a copolymer thereof, or a polyamide or a copolymer thereof.

22. A compound (101), (102), (103), (104), (105), (106), (107), (108) or (109):

(103)
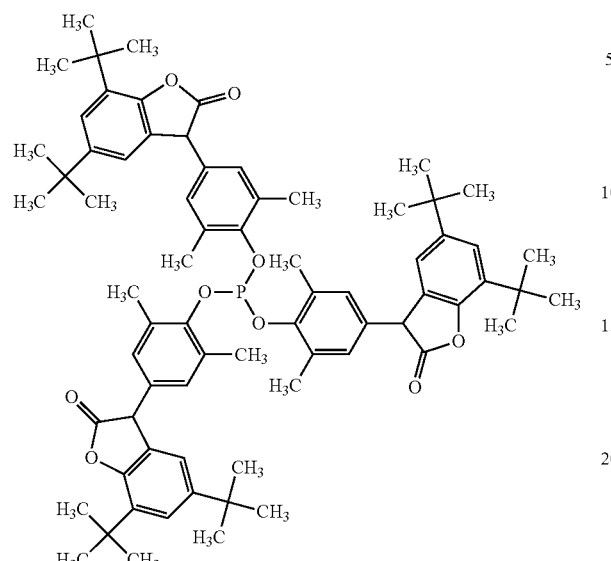
(104)
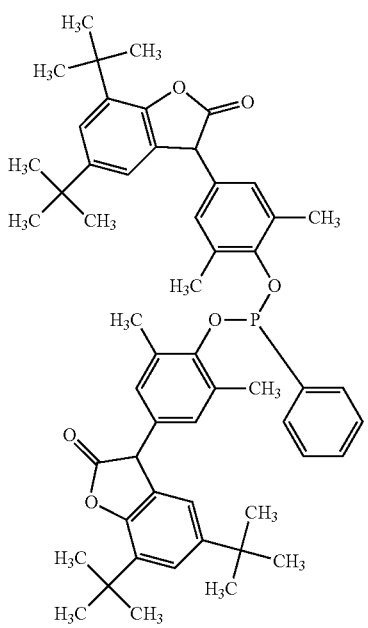
(105)
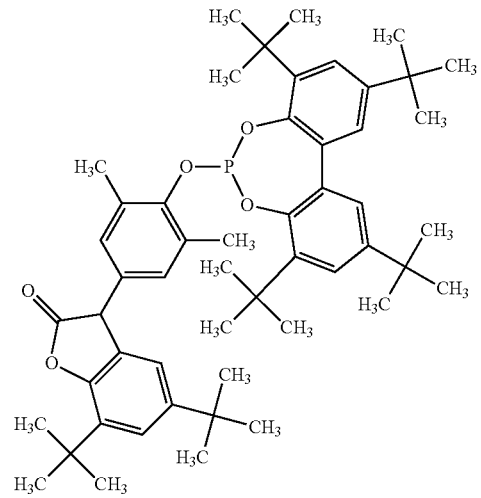
(106)
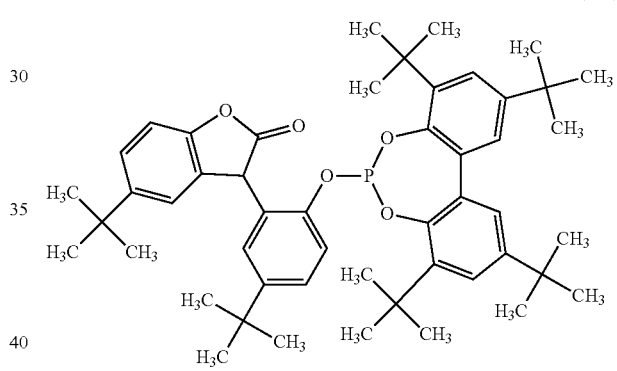
(107)
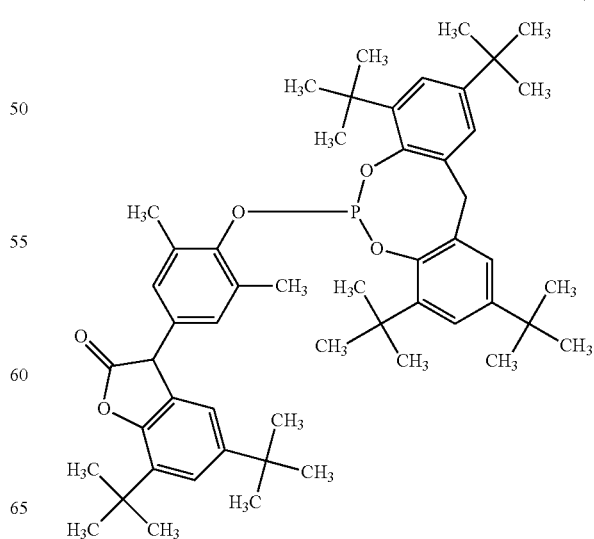

-continued

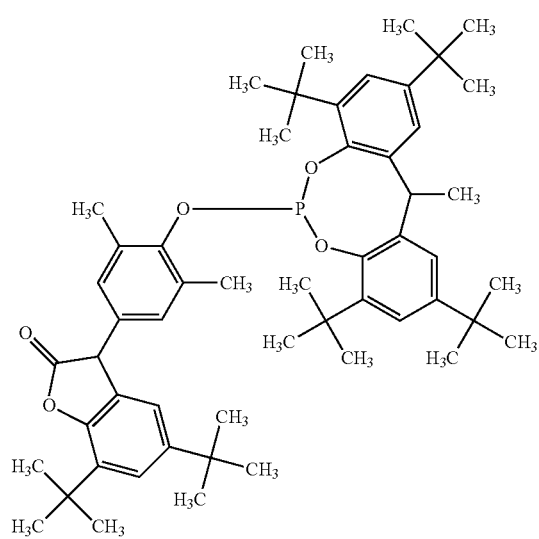
(108)

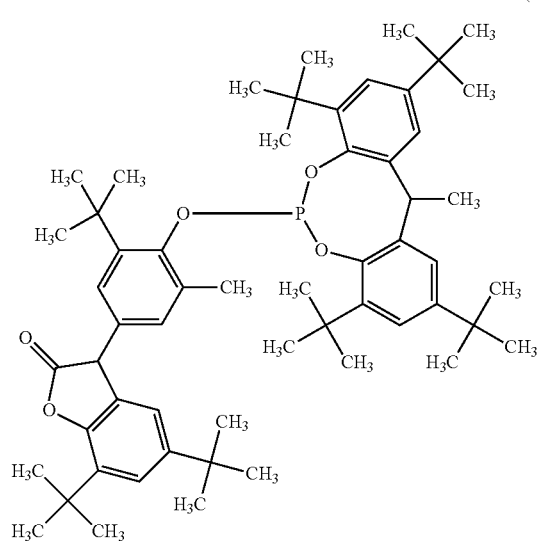
(109)

23. The compound according to claim 22, wherein the compound is compound (101).

24. The compound according to claim 22, wherein the compound is compound (102).

25. The compound according to claim 22, wherein the compound is compound (103).

26. The compound according to claim 22, wherein the compound is compound (104).

27. The compound according to claim 22, wherein the compound is compound (105).

28. The compound according to claim 22, wherein the compound is compound (106).

29. The compound according to claim 22, wherein the compound is compound (107).

30. The compound according to claim 22, wherein the compound is compound (108).

31. The compound according to claim 22, wherein the compound is compound (109).

32. An additive composition, comprising:
b) a compound (101), (102), (103), (104), (105), (106), (107), (108) or (109); and
c) a first further additive, which is a phosphite or phosphorite different to component b), an acid scavenger, a phenolic antioxidant or an aminic antioxidant:

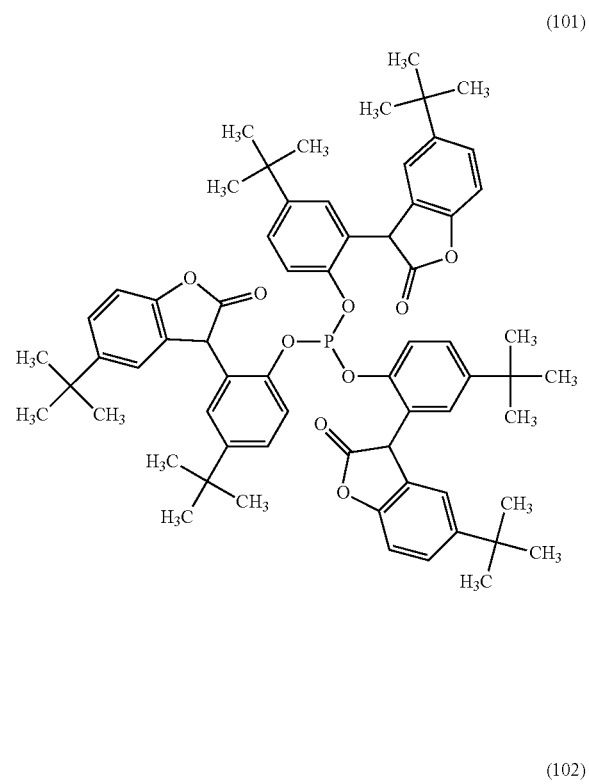
(101)

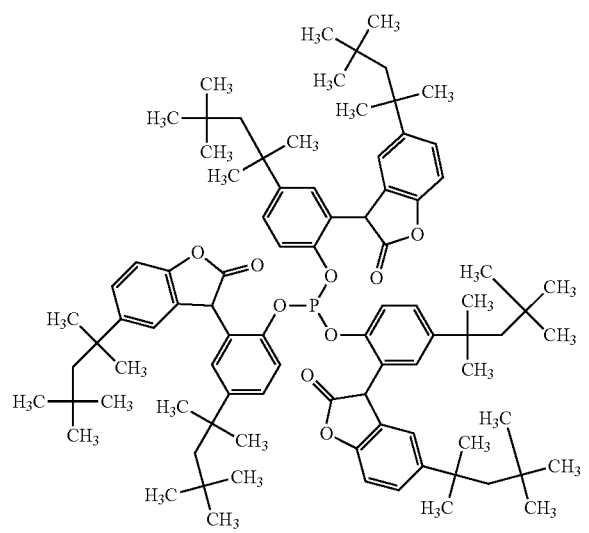
(102)

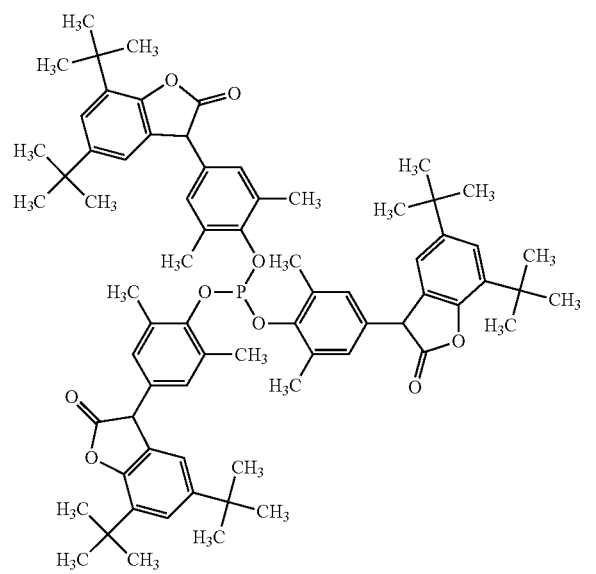
(103)
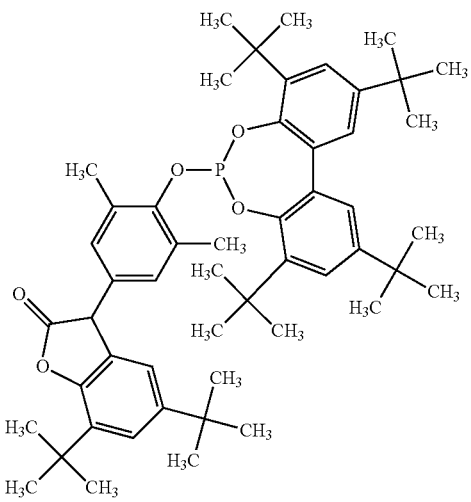
(105)
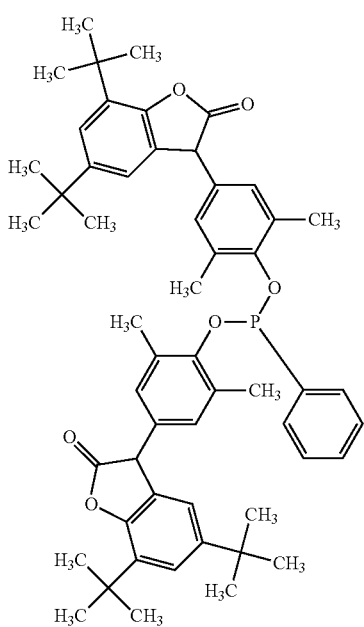
(104)
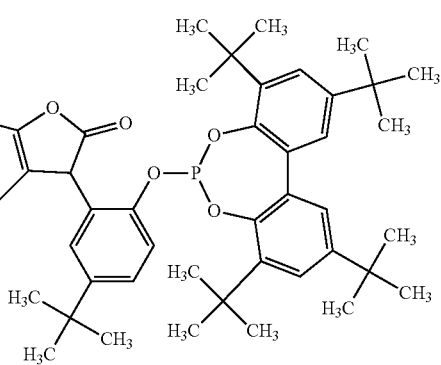
(106)

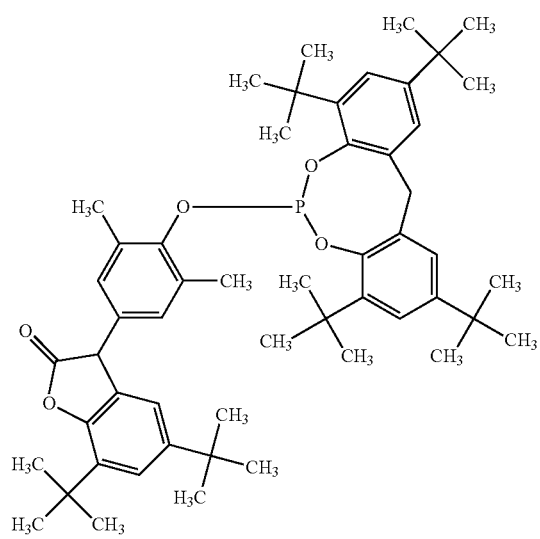
(107)

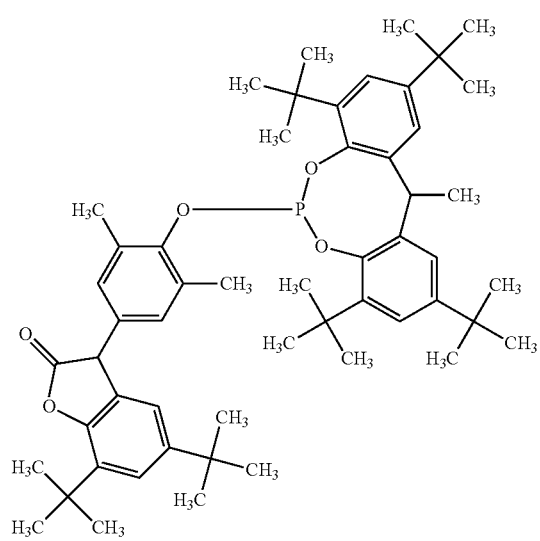
(108)

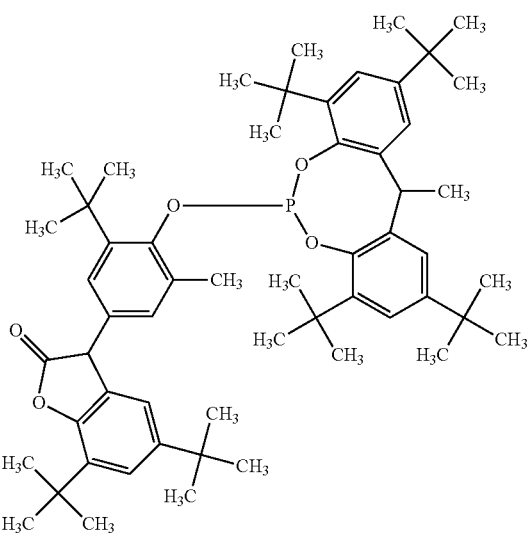
(109)

33. The additive composition according to claim 32, which comprises, as component c), a phenolic antioxidant, which is an ester of β-(3,5-di-tert-butyl-4-hydroxyphenyl) propionic acid.

34. The additive composition according to claim 32, further comprising:

as a component d), a second further additive, which is a phosphite or phosphonite different to component b), an acid scavenger, a phenolic antioxidant or an aminic antioxidant, with the proviso that component d) is a different substance than component c).

* * * * *

UNITED STATES PATENT AND TRADEMARK OFFICE
CERTIFICATE OF CORRECTION

PATENT NO. : 10,259,931 B2
APPLICATION NO. : 15/920877
DATED : April 16, 2019
INVENTOR(S) : Werner Hoelzl et al.

It is certified that error appears in the above-identified patent and that said Letters Patent is hereby corrected as shown below:

In the Specification

At Column 2, Lines 15-28 (approx.), delete "

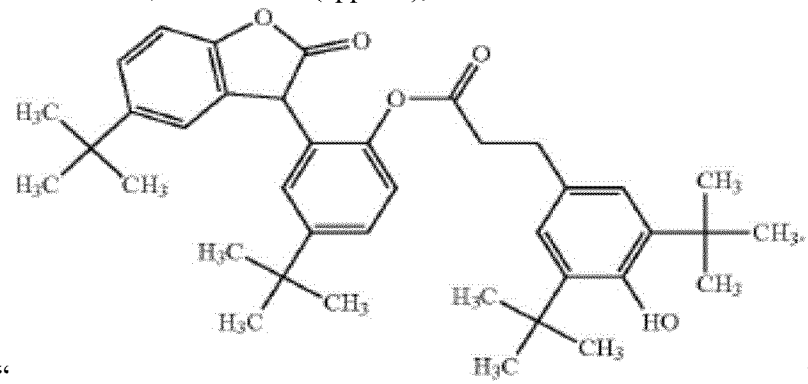

" and insert

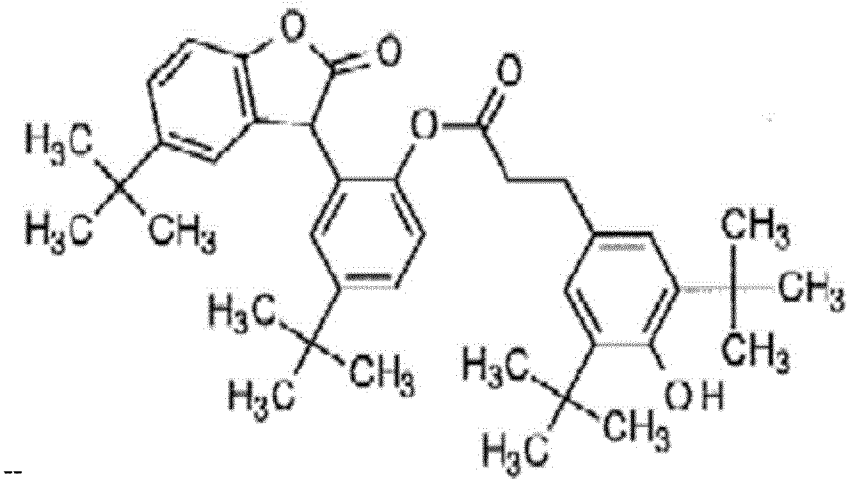

--, therefor.

At Column 5, Lines 57-58, delete "2-methylpentoxy," and insert -- 2-methyl-pentoxy, --, therefor.

Signed and Sealed this
Twenty-second Day of September, 2020

Andrei Iancu
*Director of the United States Patent and Trademark Office*

CERTIFICATE OF CORRECTION (continued)

U.S. Pat. No. 10,259,931 B2

At Column 7, Line 40, delete "IIa" and insert -- IIIa --, therefor.

At Column 8, Line 49, delete "under 6)," and insert -- under 6.), --, therefor.

At Column 11, Line 11, delete "terephtalate," and insert -- terephthalate, --, therefor.

At Column 11, Lines 12-13, delete "polybutylensuccinate" and insert -- polybutylene succinate --, therefor.

At Column 11, Line 13, delete "polybutylensuccinate" and insert -- polybutylene succinate --, therefor.

At Column 12, Line 31, delete "steriod" and insert -- steroid --, therefor.

At Column 12, Line 33, delete "jojo-baoil." and insert -- jojoba oil. --, therefor.

At Column 13, Line 43, delete "C-alkyl" and insert -- $C_1$-alkyl --, therefor.

At Column 16, Line 48, delete "III-M;" and insert -- II-M; --, therefor.

At Column 18, Line 43, delete "$C_1$-$C_5$-alkyl," and insert -- $C_1$-$C_8$-alkyl, --, therefor.

At Column 19, Line 14, delete "11-0" and insert -- II-O --, therefor.

At Column 20, Line 46, delete "$R^{o1}$" and insert -- $R^{1O}$ --, therefor.

At Column 21, Line 14, delete "III-M," and insert -- II-M, --, therefor.

At Column 21, Line 24, delete "III-P," and insert -- II-P, --, therefor.

At Column 21, Line 27, delete "RIM" and insert -- $R^{1M}$ --, therefor.

At Column 21, Line 40, delete "$R^6$" and insert -- $R^{O6}$ --, therefor.

At Column 23, Line 2, delete "methylcyclo-hexyl)" and insert -- methylcyclohexyl) --, therefor.

At Column 23, Line 58, delete "di methylbenzyl mercaptoacetate," and insert -- dimethylbenzylmercaptoacetate, --, therefor.

At Column 23, Line 63, begin the section "1.8" as a new paragraph.

At Column 27, Line 3, delete "tetra-methylpiperazinone)," and insert -- tetramethylpiperazinone), --, therefor.

At Column 28, Line 51 (approx.), delete "1-0" and insert -- I-O --, therefor.

At Column 30, Line 27, delete "Nhexadecyl" and insert -- N-hexadecyl --, therefor.

CERTIFICATE OF CORRECTION (continued)
U.S. Pat. No. 10,259,931 B2

At Column 33, Line 25, delete "1-0" and insert -- I-O --, therefor.

At Column 35, Line 39, delete "180° C. 15" and insert -- 180° C. --, therefor.

At Column 41, Lines 1-10 (approx.), delete " 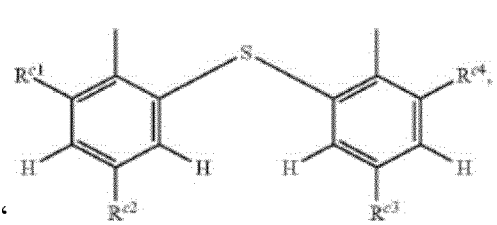 "

and insert -- 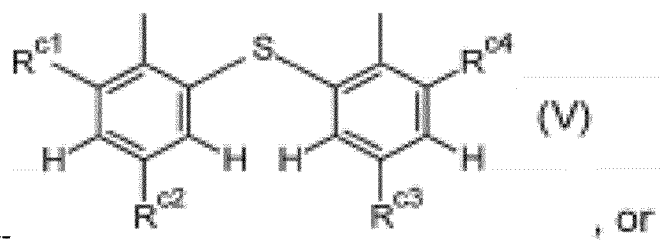 , or --, therefor.

At Column 44, Line 33 (approx.), delete "III-P," and insert -- II-P, --, therefor.

At Column 45, Lines 1-10 (approx.), delete " 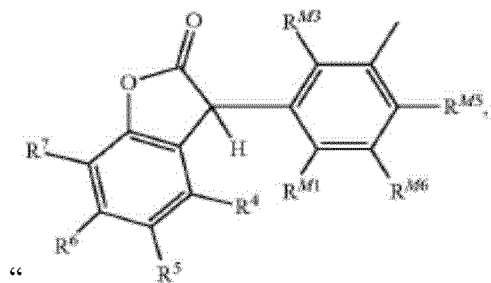 " and insert

-- 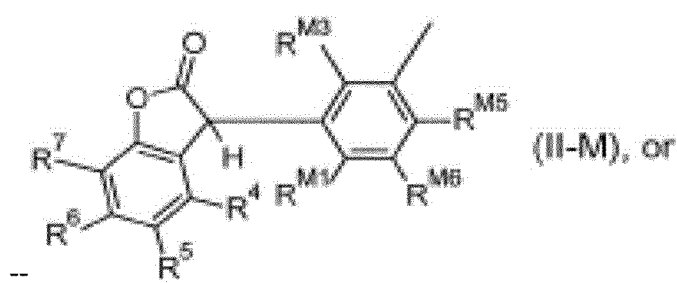 --, therefor.

At Column 46, Lines 53-63 (approx.), delete

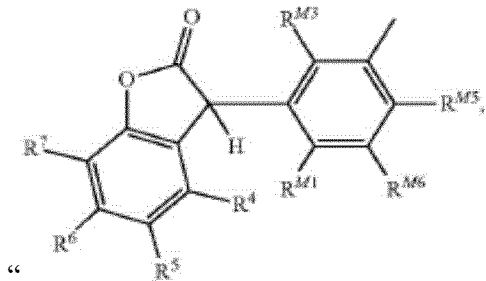

" and insert -- 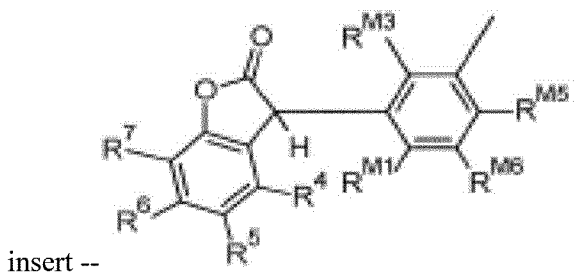 --, therefor.

At Column 48, Lines 30-40 (approx.), delete

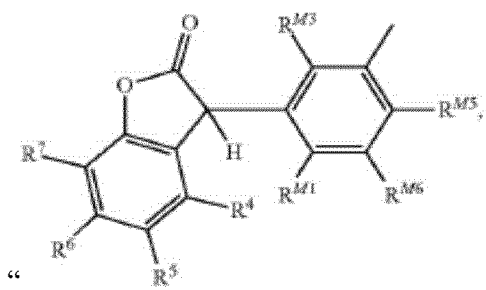

" and insert -- 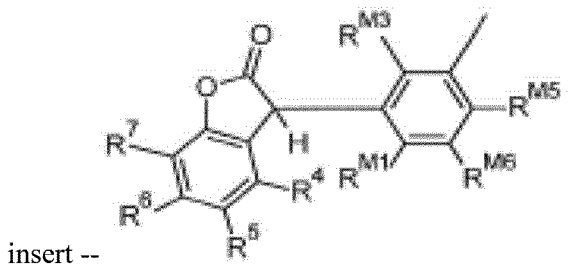 --, therefor.

At Column 53, Line 31 (approx.), delete "dichlorethane." and insert -- dichloroethane. --, therefor.

At Column 53, Line 41 (approx.), delete "(toluene-ds):" and insert -- (toluene-$d_8$): --, therefor.

At Column 53, Line 46 (approx.), delete "[M+1]+=840" and insert -- [M+1]$^+$=840 --, therefor.

At Column 55, Line 37 (approx.), delete "(toluene-ds):" and insert -- (toluene-$d_8$): --, therefor.

At Column 55, Line 39 (approx.), delete "(toluene-ds):" and insert -- (toluene-$d_8$): --, therefor.

CERTIFICATE OF CORRECTION (continued)
U.S. Pat. No. 10,259,931 B2

At Column 57, Lines 3-4, delete "benzodioxa-phosphocine," and insert -- benzodioxaphosphocine, --, therefor.

At Column 57, Line 8, delete "(toluene-ds):" and insert -- (toluene-$d_8$): --, therefor.

In the Claims

At Column 77, Line 21 (approx.), Claim 8, delete "phosphorite" and insert -- phosphonite --, therefor.

At Column 77, Line 27 (approx.), Claim 9, delete "P-(3,5" and insert -- β-(3,5 --, therefor.

At Column 77, Line 33 (approx.), Claim 10, delete "phosphorite" and insert -- phosphonite --, therefor.

At Column 77, Lines 40-41 (approx.), Claim 11, delete "component (h)" and insert -- component (b) --, therefor.

At Column 77, Lines 45-46, Claim 13, delete "component (h)" and insert -- component (b) --, therefor.

At Column 86, Lines 12-13 (approx.), Claim 32, delete "phosphorite" and insert -- phosphonite --, therefor.